US012698521B2

(12) United States Patent
Selles Vidal et al.

(10) Patent No.: US 12,698,521 B2
(45) Date of Patent: Aug. 4, 2026

(54) METHOD OF SELECTING A POLYPEPTIDE OF INTEREST

(71) Applicant: IMPERIAL COLLEGE INNOVATIONS LIMITED, London (GB)

(72) Inventors: Lara Selles Vidal, London (GB); John Heap, London (GB)

(73) Assignee: Imperial College Innovations Limited, London (GB)

( * ) Notice: Subject to any disclaimer, the term of this patent is extended or adjusted under 35 U.S.C. 154(b) by 1061 days.

(21) Appl. No.: 17/253,314

(22) PCT Filed: Jun. 19, 2019

(86) PCT No.: PCT/GB2019/051727
§ 371 (c)(1),
(2) Date: Dec. 17, 2020

(87) PCT Pub. No.: WO2019/243821
PCT Pub. Date: Dec. 26, 2019

(65) Prior Publication Data
US 2021/0277441 A1 Sep. 9, 2021

(30) Foreign Application Priority Data
Jun. 19, 2018 (GB) ..................................... 1810052

(51) Int. Cl.
*C12Q 1/32* (2006.01)
*C12N 9/02* (2006.01)
*C12N 9/04* (2006.01)
*C12N 9/06* (2006.01)

(52) U.S. Cl.
CPC ............. *C12Q 1/32* (2013.01); *C12N 9/0006* (2013.01); *C12N 9/0028* (2013.01); *C12N 9/0036* (2013.01); *C12Y 101/01001* (2013.01); *C12Y 101/01284* (2013.01)

(58) Field of Classification Search
None
See application file for complete search history.

(56) References Cited

U.S. PATENT DOCUMENTS

2012/0190089 A1 7/2012 Buelter et al.
2016/0348079 A1 12/2016 Kim et al.

FOREIGN PATENT DOCUMENTS

WO 2013152236 A1 10/2013
WO 2016172341 A2 10/2016
WO 2019243821 A1 12/2019

OTHER PUBLICATIONS

Gupta ("*Escherichia coli* Derivatives Lacking Both Alcohol Dehydrogenase and Phosphotransacetylase Grow Anaerobically by Lactate Fermentation", Journal of Bacteriology, vol. 171 No. 7, 1989, 3650-3655. (Year: 1989).*
Drejer ("Genetic Tools and Techniques for Recombinant Expression in Thermophilic Bacillaceae" Microorganisms, May 2018, 6, 42, 1-19). (Year: 2018).*
Branduardi ("Lactate production yield from engineered yeast is dependent from the host background, the lactate dehydrogenase source and the lactate export" Microbial Cell Factories, 2006, 5:4), 1-12) (Year: 2006).*
International Search Report and Written Opinion for PCT/GB2019/051727 dated Nov. 6, 2019, 20 pages.
GB Search report for GB 1810052.9 dated Mar. 12, 2019, 5 pages.

* cited by examiner

*Primary Examiner* — Robert J Yamasaki
*Assistant Examiner* — Charles Zoltan Constantine
(74) *Attorney, Agent, or Firm* — Linda B. Huber; Nixon Peabody LLP

(57) ABSTRACT

The invention relates to methods for identifying polypeptides and polynucleotides of interest, be they novel or variant polypeptides and polynucleotides, by expressing a plurality of polypeptides in an obligate or facultative anaerobe that is incapable of, or displays a reduction in, the oxidation of NADH and/or NADPH under anaerobic fermentation conditions and selecting an obligate or facultative anaerobe that grows or displays a growth advantage under said conditions. The invention is also concerned with novel enzymes per se, and their use in enzymatic production processes.

11 Claims, 36 Drawing Sheets

Specification includes a Sequence Listing.

a b c

Specific enzymatic activity of TADH from purified

Exogenous product (not membrane permeable)

Final product

Promiscuous NADH-dependent oxidoreductase

Figure 8 continued

Figure 12 a     AL mutant (Δ*adhE* Δ*ldhA*)

c     ALP mutant (Δ*adhE* Δ*ldhA* Δ*pntB*)

b     ALS mutant (Δ*adhE* Δ*ldhA* Δ*sthA*)

d     ALPS mutant (Δ*adhE* Δ*ldhA* Δ*pntB* Δ*sthA*)

Figure 20:
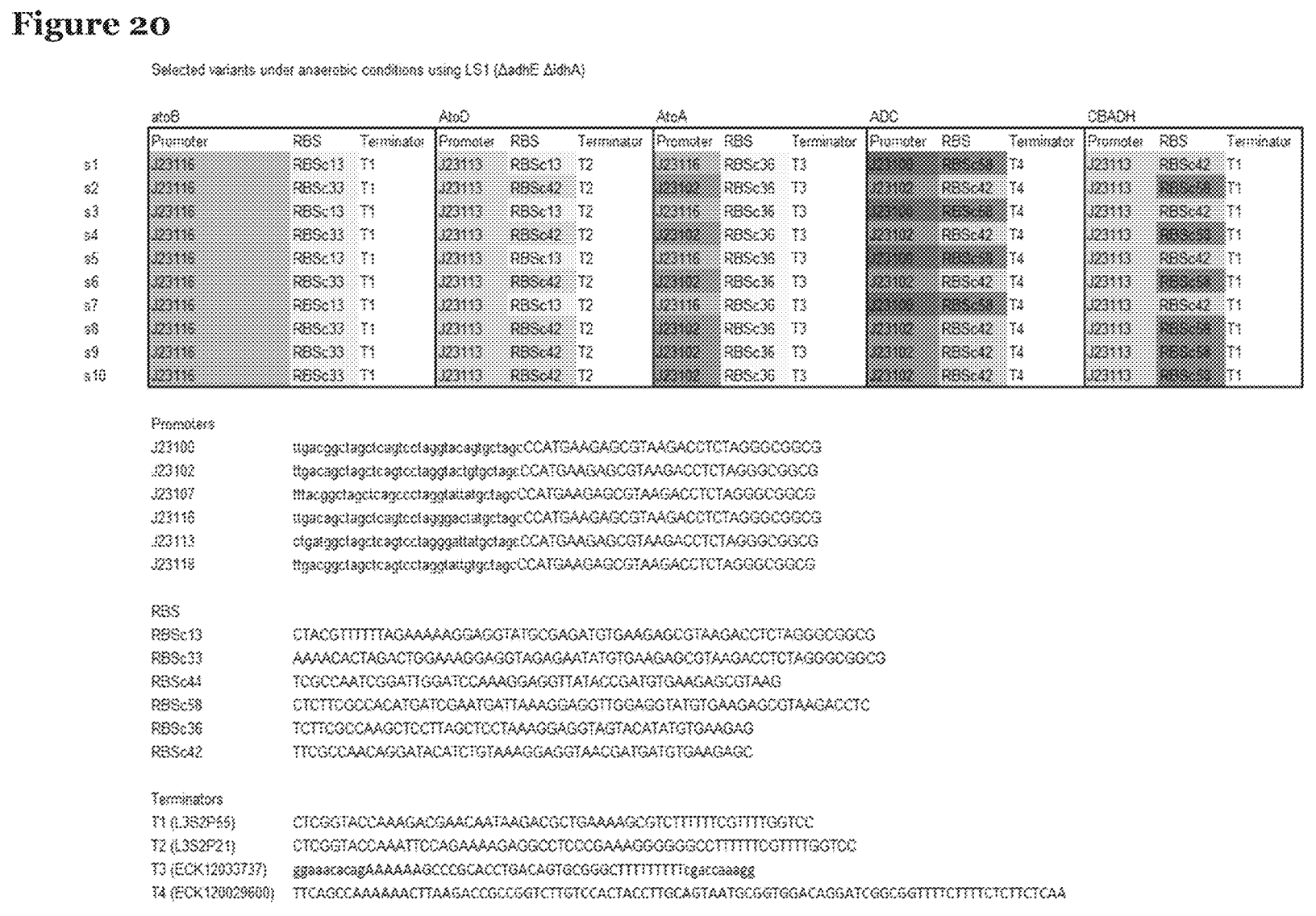

Selected variants under anaerobic conditions using LS1 (ΔadhE ΔldhA)

SEQUENCE LISTING

<160> NUMBER OF SEQ ID NOS: 105

<210> SEQ ID NO 1
<211> LENGTH: 351
<212> TYPE: PRT
<213> ORGANISM: Clostridium beijerinckii

<400> SEQUENCE: 1

```
Met Lys Gly Phe Ala Met Leu Gly Ile Asn Lys Leu Gly Trp Ile Glu
1               5                   10                  15

Lys Glu Arg Pro Val Ala Gly Ser Tyr Asp Ala Ile Val Arg Pro Leu
            20                  25                  30

Ala Val Ser Pro Cys Thr Ser Asp Ile His Thr Val Phe Glu Gly Ala
        35                  40                  45

Leu Gly Asp Arg Lys Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Gly Glu Tyr Phe His Val Asn Asp
            115                 120                 125
```

-continued

```
Ala Asp Met Asn Leu Ala Ile Leu Pro Lys Asp Met Pro Leu Glu Asn
    130             135             140

Ala Val Met Ile Thr Asp Met Met Thr Thr Gly Phe His Gly Ala Glu
145             150             155             160

Leu Ala Asp Ile Gln Met Gly Ser Ser Val Val Val Ile Gly Ile Gly
            165             170             175

Ala Val Gly Leu Met Gly Ile Ala Gly Ala Lys Leu Arg Gly Ala Gly
            180             185             190

Arg Ile Ile Gly Val Gly Ser Arg Pro Ile Cys Val Glu Ala Ala Lys
            195             200             205

Phe Tyr Gly Ala Thr Asp Ile Leu Asn Tyr Lys Asn Gly His Ile Val
    210             215             220

Asp Gln Val Met Lys Leu Thr Asn Gly Lys Gly Val Asp Arg Val Ile
225             230             235             240

Met Ala Gly Gly Gly Ser Glu Thr Leu Ser Gln Ala Val Ser Met Val
            245             250             255

Lys Pro Gly Gly Ile Ile Ser Asn Ile Asn Tyr His Gly Ser Gly Asp
            260             265             270

Ala Leu Leu Ile Pro Arg Val Glu Trp Gly Cys Gly Met Ala His Lys
    275             280             285

Thr Ile Lys Gly Gly Leu Cys Pro Gly Gly Arg Leu Arg Ala Glu Met
    290             295             300

Leu Arg Asp Met Val Val Tyr Asn Arg Val Asp Leu Ser Lys Leu Val
305             310             315             320

Thr His Val Tyr His Gly Phe Asp His Ile Glu Glu Ala Leu Leu Leu
            325             330             335

Met Lys Asp Lys Pro Lys Asp Leu Ile Lys Ala Val Val Ile Leu
    340             345             350
```

```
<210> SEQ ID NO 2
<211> LENGTH: 351
<212> TYPE: PRT
<213> ORGANISM: Artificial Sequence
<220> FEATURE:
<223> OTHER INFORMATION: amino acid variant of CBADH

<400> SEQUENCE: 2
```

```
Met Lys Gly Phe Ala Met Leu Gly Ile Asn Lys Leu Gly Trp Ile Glu
1               5               10              15

Lys Glu Arg Pro Val Ala Gly Ser Tyr Asp Ala Ile Val Arg Pro Leu
            20              25              30

Ala Val Ser Pro Cys Thr Ser Asp Ile His Thr Val Phe Glu Gly Ala
            35              40              45

Leu Gly Asp Arg Lys Asn Met Ile Leu Gly His Glu Ala Val Gly Glu
    50              55              60

Val Val Glu Val Gly Ser Glu Val Lys Asp Phe Lys Pro Gly Asp Arg
65              70              75              80

Val Ile Val Pro Cys Thr Thr Pro Asp Trp Arg Ser Leu Glu Val Gln
            85              90              95

Ala Gly Phe Gln Gln His Ser Asn Gly Met Leu Ala Gly Trp Lys Phe
            100             105             110

Ser Asn Phe Lys Asp Gly Val Phe Gly Glu Tyr Phe His Val Asn Asp
            115             120             125

Ala Asp Met Asn Leu Ala Ile Leu Pro Lys Asp Met Pro Leu Glu Asn
    130             135             140
```

-continued

```
Ala Val Met Ile Thr Asp Met Met Thr Thr Gly Phe His Gly Ala Glu
145                 150                 155                 160

Leu Ala Asp Ile Gln Met Gly Ser Ser Val Val Val Ile Gly Ile Gly
                165                 170                 175

Ala Val Gly Leu Met Gly Ile Ala Gly Ala Lys Leu Arg Gly Ala Gly
            180                 185                 190

Arg Ile Ile Gly Val Asp Tyr Arg Pro Ile Cys Val Glu Ala Ala Lys
        195                 200                 205

Phe Tyr Gly Ala Thr Asp Ile Leu Asn Pro Lys Asn Gly His Ile Val
    210                 215                 220

Asp Gln Val Met Lys Leu Thr Asn Gly Lys Gly Val Asp Arg Val Ile
225                 230                 235                 240

Met Ala Gly Gly Gly Ser Glu Thr Leu Ser Gln Ala Val Ser Met Val
                245                 250                 255

Lys Pro Gly Gly Ile Ile Ser Asn Ile Asn Tyr His Gly Ser Gly Asp
                260                 265                 270

Ala Leu Leu Ile Pro Arg Val Glu Trp Gly Cys Gly Met Ala His Lys
            275                 280                 285

Thr Ile Lys Gly Gly Leu Cys Pro Gly Gly Arg Leu Arg Ala Glu Met
        290                 295                 300

Leu Arg Asp Met Val Val Tyr Asn Arg Val Asp Leu Ser Lys Leu Val
305                 310                 315                 320

Thr His Val Tyr His Gly Phe Asp His Ile Glu Glu Ala Leu Leu Leu
                325                 330                 335

Met Lys Asp Lys Pro Lys Asp Leu Ile Lys Ala Val Val Ile Leu
                340                 345                 350
```

<210> SEQ ID NO 3
<211> LENGTH: 1056
<212> TYPE: DNA
<213> ORGANISM: Artificial Sequence
<220> FEATURE:
<223> OTHER INFORMATION: variant of CBADH

<400> SEQUENCE: 3

```
atgaaaggct ttgccatgct gggtattaac aaattaggat ggattgaaaa agaacgcccc      60
gtcgcgggtt cctatgatgc gattgtacga cccttagccg tttccccgtg cactagcgat     120
attcatacag tatttgaagg ggctctcggc gatcgaaaga atatgatttt aggccatgaa     180
gccgttggcg aagtcgttga agtgggctcc gaagtgaaag atttcaaacc gggtgaccgt     240
gtcatcgtgc cctgtactac cccagattgg cgctctctgg aggttcaagc tggttttcaa     300
caacatagta atggtatgtt ggccggctgg aagttttcca acttcaaaga tggagtattt     360
ggggagtatt ttcatgtgaa cgatgcggat atgaatttgg ccatcctgcc aaaagacatg     420
cccttggaga atgctgtaat gatcaccgat atgatgacca ccggatttca tggggccgag     480
ttggccgata tccagatggg tagttctgtc gttgtgattg gtatcggggc agttgggtta     540
atgggaattg ctggggccaa attacgcgga gcaggtcgga ttattggtgt cgactataga     600
cctatttgcg ttgaggccgc caagttctac ggcgcgaccg acattctgaa tccgaaaaat     660
ggccatattg tggaccaggt aatgaagcta accaatggga aaggcgtgga ccgtgtgatt     720
atggctggag gtgggagtga aacactgagc caagcagtga gcatggtgaa acctggggga     780
attatcagca atatcaacta tcacggctct ggtgacgctt tgttaattcc ccgcgtggaa     840
tggggatgtg gcatggcgca caagacgatc aaaggcggtt tgtgtcccgg aggccgttta     900
```

```
cgggccgaaa tgctacggga tatggtggtg tacaaccgtg tggatttgtc caagctggtg    960
actcacgttt atcacggttt tgaccatatt gaagaagcct tgctactcat gaaagataaa    1020
cctaaagatc tcattaaggc cgtagttatc ctctaa                              1056

<210> SEQ ID NO 4
<211> LENGTH: 41
<212> TYPE: DNA
<213> ORGANISM: Artificial Sequence
<220> FEATURE:
<223> OTHER INFORMATION: oligoLS19

<400> SEQUENCE: 4
ccgttcgcat gcaggaggta cgaacacatg gctgttacta a                         41

<210> SEQ ID NO 5
<211> LENGTH: 29
<212> TYPE: DNA
<213> ORGANISM: Artificial Sequence
<220> FEATURE:
<223> OTHER INFORMATION: oligoLS20

<400> SEQUENCE: 5
gctgaaggat ccttaagcgg attttttcg                                       29

<210> SEQ ID NO 6
<211> LENGTH: 66
<212> TYPE: DNA
<213> ORGANISM: Artificial Sequence
<220> FEATURE:
<223> OTHER INFORMATION: oligoLS21

<400> SEQUENCE: 6
ccgttcgcat gccaatctta atcaaatcag acagagagag tacaatatga aaaaagtcgc    60
acttgt                                                               66

<210> SEQ ID NO 7
<211> LENGTH: 39
<212> TYPE: DNA
<213> ORGANISM: Artificial Sequence
<220> FEATURE:
<223> OTHER INFORMATION: oligoLS22

<400> SEQUENCE: 7
ttcagcggat ccttagttaa acaccatccc gccgtcgat                            39

<210> SEQ ID NO 8
<211> LENGTH: 44
<212> TYPE: DNA
<213> ORGANISM: Artificial Sequence
<220> FEATURE:
<223> OTHER INFORMATION: oligoLS23

<400> SEQUENCE: 8
ccgttcgcat gcaggaggta cgaacacatg aaggcagcaa gatg                      44

<210> SEQ ID NO 9
<211> LENGTH: 40
<212> TYPE: DNA
<213> ORGANISM: Artificial Sequence
<220> FEATURE:
<223> OTHER INFORMATION: oligoLS24

<400> SEQUENCE: 9
gctgaaggat ccttagttag gtctaacaag gattttgact                           40
```

<210> SEQ ID NO 10
<211> LENGTH: 60
<212> TYPE: DNA
<213> ORGANISM: Artificial Sequence
<220> FEATURE:
<223> OTHER INFORMATION: oligoLS87

<400> SEQUENCE: 10
gttcgcatgc attcggatct atacagataa ggagaaagag atgaaaggct ttgccatgct          60

<210> SEQ ID NO 11
<211> LENGTH: 38
<212> TYPE: DNA
<213> ORGANISM: Artificial Sequence
<220> FEATURE:
<223> OTHER INFORMATION: oligoLS88

<400> SEQUENCE: 11
cttccatgga tcctcactat tagaggataa ctacggcc                                  38

<210> SEQ ID NO 12
<211> LENGTH: 54
<212> TYPE: DNA
<213> ORGANISM: Artificial Sequence
<220> FEATURE:
<223> OTHER INFORMATION: oligoLS112
<220> FEATURE:
<221> NAME/KEY: misc_feature
<222> LOCATION: (25)..(33)
<223> OTHER INFORMATION: n is a, c, g, or t

<400> SEQUENCE: 12
cttggcggcc tcaacgcaaa taggnnnnnn nnngacacca ataatccgac ctgc               54

<210> SEQ ID NO 13
<211> LENGTH: 51
<212> TYPE: DNA
<213> ORGANISM: Artificial Sequence
<220> FEATURE:
<223> OTHER INFORMATION: oligoLS113
<220> FEATURE:
<221> NAME/KEY: misc_feature
<222> LOCATION: (28)..(30)
<223> OTHER INFORMATION: n is a, c, g, or t

<400> SEQUENCE: 13
ttctacggcg cgaccgacat tctgaatnnn aaaaatggcc atattgtgga c                  51

<210> SEQ ID NO 14
<211> LENGTH: 56
<212> TYPE: DNA
<213> ORGANISM: Artificial Sequence
<220> FEATURE:
<223> OTHER INFORMATION: oligoLS162

<400> SEQUENCE: 14
gctgaaggat ccttagtggt ggtggtggtg gtggttaggt ctaacaagga ttttga            56

<210> SEQ ID NO 15
<211> LENGTH: 58
<212> TYPE: DNA
<213> ORGANISM: Artificial Sequence
<220> FEATURE:
<223> OTHER INFORMATION: oligoLS163

<400> SEQUENCE: 15

-continued

```
gctgaaggat ccttagtggt ggtggtggtg gtggaggata actacggcct taatgaga          58

<210> SEQ ID NO 16
<211> LENGTH: 30
<212> TYPE: DNA
<213> ORGANISM: Artificial Sequence
<220> FEATURE:
<223> OTHER INFORMATION: oligoLS168

<400> SEQUENCE: 16
ccgttcgcat gcaggaggta cgaacacatg                                         30

<210> SEQ ID NO 17
<211> LENGTH: 34
<212> TYPE: DNA
<213> ORGANISM: Artificial Sequence
<220> FEATURE:
<223> OTHER INFORMATION: oligoLS169

<400> SEQUENCE: 17
ttcagcggat ccttatccgc gaactacaag caat                                    34

<210> SEQ ID NO 18
<211> LENGTH: 56
<212> TYPE: DNA
<213> ORGANISM: Artificial Sequence
<220> FEATURE:
<223> OTHER INFORMATION: oligoLS170

<400> SEQUENCE: 18
gctgaaggat ccttagtggt ggtggtggtg gtgtccgcga actacaagca atacct           56

<210> SEQ ID NO 19
<211> LENGTH: 50
<212> TYPE: DNA
<213> ORGANISM: Artificial Sequence
<220> FEATURE:
<223> OTHER INFORMATION: oligoLS208

<400> SEQUENCE: 19
ttcagcggat ccaatgtatc tgcatgaagc acagacccac cagttactgg                  50

<210> SEQ ID NO 20
<211> LENGTH: 52
<212> TYPE: DNA
<213> ORGANISM: Artificial Sequence
<220> FEATURE:
<223> OTHER INFORMATION: oligoLS209

<400> SEQUENCE: 20
ttcagcaagc ttcattaaac cgctctcatc aaccatggtc agacccagtt cg               52

<210> SEQ ID NO 21
<211> LENGTH: 37
<212> TYPE: DNA
<213> ORGANISM: Artificial Sequence
<220> FEATURE:
<223> OTHER INFORMATION: oligoLS216

<400> SEQUENCE: 21
ttcagcggat ccgaaacgac cagagccgcc aggttca                                37

<210> SEQ ID NO 22
<211> LENGTH: 59
<212> TYPE: DNA
<213> ORGANISM: Artificial Sequence
```

<220> FEATURE:
<223> OTHER INFORMATION: oligoLS218

<400> SEQUENCE: 22
ttcagcaagc ttcaggaggg tgttcttaag cttcataaaa ataatccttc gccttgcgc          59

<210> SEQ ID NO 23
<211> LENGTH: 63
<212> TYPE: DNA
<213> ORGANISM: Artificial Sequence
<220> FEATURE:
<223> OTHER INFORMATION: oligoLS228

<400> SEQUENCE: 23
aaggggttgg tctcatgtgg ctcttcgatg ttaaaggatg aagtaattaa acaaattagc          60
acg                                                                        63

<210> SEQ ID NO 24
<211> LENGTH: 68
<212> TYPE: DNA
<213> ORGANISM: Artificial Sequence
<220> FEATURE:
<223> OTHER INFORMATION: olilgoLS229

<400> SEQUENCE: 24
aaggggttgg tctctggtct tacgctcttc attacttaag ataatcatat ataacttcag          60
ctctaggc                                                                   68

<210> SEQ ID NO 25
<211> LENGTH: 48
<212> TYPE: DNA
<213> ORGANISM: Artificial Sequence
<220> FEATURE:
<223> OTHER INFORMATION: oligoLS232

<400> SEQUENCE: 25
aaggggttgg tctcatgtgg ctcttcgatg aaaggctttg ccatgctg                       48

<210> SEQ ID NO 26
<211> LENGTH: 58
<212> TYPE: DNA
<213> ORGANISM: Artificial Sequence
<220> FEATURE:
<223> OTHER INFORMATION: oligoLS233

<400> SEQUENCE: 26
aaggggttgg tctctggtct tacgctcttc attagaggat aactacggcc ttaatgag           58

<210> SEQ ID NO 27
<211> LENGTH: 58
<212> TYPE: DNA
<213> ORGANISM: Artificial Sequence
<220> FEATURE:
<223> OTHER INFORMATION: oligoLS234

<400> SEQUENCE: 27
aaggggttgg tctcatgtgg ctcttcgatg aaaacaaaat tgatgacatt acaagacg           58

<210> SEQ ID NO 28
<211> LENGTH: 56
<212> TYPE: DNA
<213> ORGANISM: Artificial Sequence
<220> FEATURE:
<223> OTHER INFORMATION: oligoLS235

-continued

```
<400> SEQUENCE: 28
aaggggttgg tctctggtct tacgctcttc attataaatc accccgttgc gtattc        56

<210> SEQ ID NO 29
<211> LENGTH: 52
<212> TYPE: DNA
<213> ORGANISM: Artificial Sequence
<220> FEATURE:
<223> OTHER INFORMATION: oligoLS242

<400> SEQUENCE: 29
aaggggttgg tctcatgtgg ctcttcgatg gatgcgaaac aacgtattgc gc          52

<210> SEQ ID NO 30
<211> LENGTH: 61
<212> TYPE: DNA
<213> ORGANISM: Artificial Sequence
<220> FEATURE:
<223> OTHER INFORMATION: oligoLS243

<400> SEQUENCE: 30
aaggggttgg tctctggtct tacgctcttc attatttgct ctcctgtgaa acgatgatgt    60
g                                                                    61

<210> SEQ ID NO 31
<211> LENGTH: 33
<212> TYPE: DNA
<213> ORGANISM: Artificial Sequence
<220> FEATURE:
<223> OTHER INFORMATION: oligoLS244

<400> SEQUENCE: 31
ttcagcggat cctgtctgtt ttgcggtcgc cag                                 33

<210> SEQ ID NO 32
<211> LENGTH: 37
<212> TYPE: DNA
<213> ORGANISM: Artificial Sequence
<220> FEATURE:
<223> OTHER INFORMATION: oligoLS245

<400> SEQUENCE: 32
ttcagcaagc ttcaagcaga atcaagttct accgtgc                             37

<210> SEQ ID NO 33
<211> LENGTH: 829
<212> TYPE: DNA
<213> ORGANISM: Artificial Sequence
<220> FEATURE:
<223> OTHER INFORMATION: gBlockLS3

<400> SEQUENCE: 33
ccgttcgcat gccaatctta atcaaatcag acagagagag tacaatatga aaaaagtcgc    60
acttgttacc ggcgccggcc aggggattgg taaagctatc gcccttcgtc tggtgaagga   120
tggatttgcc gtggccattg ccgattataa cgacaccacc gccaaagcgg tcgcctccga   180
aatcaaccag gccggcggcc gcgccatggc ggtgaaagtg gatgtctccg accgcgatca   240
ggtgtttgcc gccgtcgaac aggcgcgcaa aacgctgggc ggcttcgacg tcatcgtcaa   300
caacgccggc gtggcgccgt ccacgccgat cgagtccatt accccggaga ttgtcgataa   360
agtctacaac atcaacgtta aaggggtgat ctggggcatt caggcggcgg tcgaggcctt   420
taagaaagag ggtcacggcg ggaaaatcat caacgcctgt tcccaggccg gccacgtcgg   480
```

-continued

```
caacccggag ctggcggtat atagctcgag taaattcgcc gtacgcggct taacccagac      540
cgccgctcgc gacctcgcgc cgctgggcat cacagtcaac ggctactgcc cggggattgt      600
caaaacgcca atgtgggccg aaattgaccg ccaggtgtcc gaagccgccg gtaaaccgct      660
gggttacggt accgccgagt cgccaaacg catcaccctc ggccgcctgt ccgagccgga      720
agatgtcgcc gcctgcgtct cctatcttgc cagcccggat tctgattata tgaccggtca      780
gtcattgctg atcgacggcg ggatggtgtt taactaagga tccgctgaa       829
```

<210> SEQ ID NO 34
<211> LENGTH: 291
<212> TYPE: PRT
<213> ORGANISM: Unknown
<220> FEATURE:
<223> OTHER INFORMATION: Myxococcus stipitatus imine reductase

<400> SEQUENCE: 34

```
Met Lys Pro Thr Leu Thr Val Ile Gly Ala Gly Arg Met Gly Ser Ala
1               5                   10                  15

Leu Ile Lys Ala Phe Leu Gln Ser Gly Tyr Thr Thr Thr Val Trp Asn
            20                  25                  30

Arg Thr Lys Ala Lys Ser Glu Pro Leu Ala Lys Leu Gly Ala His Leu
        35                  40                  45

Ala Asp Thr Val Arg Asp Ala Val Lys Arg Ser Asp Ile Ile Val Val
    50                  55                  60

Asn Val Leu Asp Tyr Asp Thr Ser Asp Gln Leu Leu Arg Gln Asp Glu
65                  70                  75                  80

Val Thr Arg Glu Leu Arg Gly Lys Leu Leu Val Gln Leu Thr Ser Gly
            85                  90                  95

Ser Pro Ala Leu Ala Arg Glu Gln Glu Thr Trp Ala Arg Gln His Gly
            100                 105                 110

Ile Asp Tyr Leu Asp Gly Ala Ile Met Ala Thr Pro Asp Phe Ile Gly
            115                 120                 125

Gln Ala Glu Cys Ala Leu Leu Tyr Ser Gly Ser Ala Ala Leu Phe Glu
        130                 135                 140

Lys His Arg Ala Val Leu Asn Val Leu Gly Gly Ala Thr Ser His Val
145                 150                 155                 160

Gly Glu Asp Val Gly His Ala Ser Ala Leu Asp Ser Ala Leu Leu Phe
            165                 170                 175

Gln Met Trp Gly Thr Leu Phe Gly Thr Leu Gln Ala Leu Ala Ile Ser
            180                 185                 190

Arg Ala Glu Gly Ile Pro Leu Glu Lys Thr Thr Ala Phe Ile Lys Leu
        195                 200                 205

Thr Glu Pro Val Thr Gln Gly Ala Val Ala Asp Val Leu Thr Arg Val
        210                 215                 220

Gln Gln Asn Arg Leu Thr Ala Asp Ala Gln Thr Leu Ala Ser Leu Glu
225                 230                 235                 240

Ala His Asn Val Ala Phe Gln His Leu Leu Ala Leu Cys Glu Glu Arg
            245                 250                 255

Asn Ile His Arg Gly Val Ala Asp Ala Met Tyr Ser Val Ile Arg Glu
            260                 265                 270

Ala Val Lys Ala Gly His Gly Lys Asp Asp Phe Ala Ile Leu Thr Arg
        275                 280                 285

Phe Leu Lys
        290
```

```
<210> SEQ ID NO 35
<211> LENGTH: 291
<212> TYPE: PRT
<213> ORGANISM: Artificial Sequence
<220> FEATURE:
<223> OTHER INFORMATION: variant of Myxococcus stipitatus imine
      reductase

<400> SEQUENCE: 35

Met Lys Pro Thr Leu Thr Val Ile Gly Ala Gly Arg Met Gly Ser Ala
1               5                   10                  15

Leu Ile Lys Ala Phe Leu Gln Ser Gly Tyr Thr Thr Thr Val Trp Glu
            20                  25                  30

Val Arg Lys Ala Arg Ser Glu Pro Leu Ala Lys Leu Gly Ala His Leu
        35                  40                  45

Ala Asp Thr Val Arg Asp Ala Val Lys Arg Ser Asp Ile Ile Val Val
        50                  55                  60

Asn Val Leu Asp Tyr Asp Thr Ser Asp Gln Leu Leu Arg Gln Asp Glu
65                  70                  75                  80

Val Thr Arg Glu Leu Arg Gly Lys Leu Leu Val Gln Leu Thr Ser Gly
                85                  90                  95

Ser Pro Ala Leu Ala Arg Glu Gln Glu Thr Trp Ala Arg Gln His Gly
            100                 105                 110

Ile Asp Tyr Leu Asp Gly Ala Ile Met Ala Thr Pro Asp Phe Ile Gly
            115                 120                 125

Gln Ala Glu Cys Ala Leu Leu Tyr Ser Gly Ser Ala Ala Leu Phe Glu
        130                 135                 140

Lys His Arg Ala Val Leu Asn Val Leu Gly Gly Ala Thr Ser His Val
145                 150                 155                 160

Gly Glu Asp Val Gly His Ala Ser Ala Leu Asp Ser Ala Leu Leu Phe
                165                 170                 175

Gln Met Trp Gly Thr Leu Phe Gly Thr Leu Gln Ala Leu Ala Ile Ser
            180                 185                 190

Arg Ala Glu Gly Ile Pro Leu Glu Lys Thr Thr Ala Phe Ile Lys Leu
            195                 200                 205

Thr Glu Pro Val Thr Gln Gly Ala Val Ala Asp Val Leu Thr Arg Val
        210                 215                 220

Gln Gln Asn Arg Leu Thr Ala Asp Ala Gln Thr Leu Ala Ser Leu Glu
225                 230                 235                 240

Ala His Asn Val Ala Phe Gln His Leu Leu Ala Leu Cys Glu Glu Arg
                245                 250                 255

Asn Ile His Arg Gly Val Ala Asp Ala Met Tyr Ser Val Ile Arg Glu
            260                 265                 270

Ala Val Lys Ala Gly His Gly Lys Asp Asp Phe Ala Ile Leu Thr Arg
        275                 280                 285

Phe Leu Lys
    290

<210> SEQ ID NO 36
<211> LENGTH: 876
<212> TYPE: DNA
<213> ORGANISM: Artificial Sequence
<220> FEATURE:
<223> OTHER INFORMATION: nucleotide sequence encoding variant of
      Myxococcus stipitatus imine reductase

<400> SEQUENCE: 36
```

```
atgaaaccga ccctgaccgt tattggcgct ggccgtatgg gctccgcact gattaaagca        60
ttcctgcaat ctggctacac gaccacggtg tgggaggtgc ggaaagcccg gagcgaaccg        120
ctggcaaaac tgggcgcaca tctggctgat acggtgcgtg acgccgttaa acgcagcgat        180
attatcgtgg ttaatgtgct ggattatgac acctctgatc agctgctgcg ccaagacgaa        240
gtgacgcgtg aactgcgcgg caaactgctg gttcagctga ccagcggttc tccggcactg        300
gctcgtgaac aggaaacgtg ggcgcgccaa catggcattg attatctgga cggtgcgatc        360
atggccaccc cggatttttat tggccaggca gaatgcgctc tgctgtacag tggttccgcg        420
gccctgttcg aaaaacaccg tgctgtcctg aatgtgctgg cggtgccac cagccatgtc        480 ggcgaagatg ttggtcatgc ctcagcactg gacagcgccc tgctgtttca gatgtggggc        540
accctgttcg gtacgctgca agcactggct atttctcgcg cagaaggcat cccgctggaa        600
aaaaccacgg cgtttatcaa actgaccgaa ccggtcaccc agggtgccgt tgcagatgtc        660
ctgacccgtg ttcagcaaaa tcgcctgacc gcagacgctc agacgctggc aagtctggaa        720
gctcataacg tggcgttcca cacctgctg gccctgtgtg aagaacgtaa tatccatcgc        780
ggtgttgcgg atgccatgta ctccgttatt cgtgaagcgg tcaaagccgg ccacggtaaa        840
gatgactttg caattctgac ccgcttcctg aaataa        876
```

<210> SEQ ID NO 37
<211> LENGTH: 217
<212> TYPE: PRT
<213> ORGANISM: Enterobacter cloacae

<400> SEQUENCE: 37

```
Met Asp Ile Ile Ser Val Ala Leu Lys Arg His Ser Thr Lys Ala Phe
1               5                   10                  15

Asp Ala Ser Lys Lys Leu Thr Ala Glu Glu Ala Glu Lys Ile Lys Thr
            20                  25                  30

Leu Leu Gln Tyr Ser Pro Ser Ser Thr Asn Ser Gln Pro Trp His Phe
        35                  40                  45

Ile Val Ala Ser Thr Glu Glu Gly Lys Ala Arg Val Ala Lys Ser Ala
    50                  55                  60

Ala Gly Thr Tyr Val Phe Asn Glu Arg Lys Met Leu Asp Ala Ser His
65                  70                  75                  80

Val Val Val Phe Cys Ala Lys Thr Ala Met Asp Asp Ala Trp Leu Glu
                85                  90                  95

Arg Val Val Asp Gln Glu Glu Ala Asp Gly Arg Phe Asn Thr Pro Glu
            100                 105                 110

Ala Lys Ala Ala Asn His Lys Gly Arg Thr Tyr Phe Ala Asp Met His
        115                 120                 125

Arg Val Asp Leu Lys Asp Asp Asp Gln Trp Met Ala Lys Gln Val Tyr
    130                 135                 140

Leu Asn Val Gly Asn Phe Leu Leu Gly Val Gly Ala Met Gly Leu Asp
145                 150                 155                 160

Ala Val Pro Ile Glu Gly Phe Asp Ala Ala Ile Leu Asp Glu Glu Phe
                165                 170                 175

Gly Leu Lys Glu Lys Gly Phe Thr Ser Leu Val Val Val Pro Val Gly
            180                 185                 190

His His Ser Val Glu Asp Phe Asn Ala Thr Leu Pro Lys Ser Arg Leu
        195                 200                 205

Pro Leu Ser Thr Ile Val Thr Glu Cys
```

```
      210                  215
```

<210> SEQ ID NO 38
<211> LENGTH: 217
<212> TYPE: PRT
<213> ORGANISM: Artificial Sequence
<220> FEATURE:
<223> OTHER INFORMATION: amino acid variant of Enterobacter cloacae
      nitroreductase

<400> SEQUENCE: 38

```
Met Asp Ile Ile Ser Val Ala Leu Lys Arg His Ser Thr Lys Ala Phe
1               5                   10                  15

Asp Ala Ser Lys Lys Leu Thr Ala Glu Glu Ala Glu Lys Ile Lys Thr
                20                  25                  30

Leu Leu Gln Tyr Ser Pro Ser Ala Ile Asn Ser Gln Pro Trp His Phe
            35                  40                  45

Ile Val Ala Ser Thr Glu Glu Gly Lys Ala Arg Val Ala Lys Ser Ala
        50                  55                  60

Ala Gly Thr Tyr Val Phe Asn Glu Arg Lys Met Leu Asp Ala Ser His
65                  70                  75                  80

Val Val Val Phe Cys Ala Lys Thr Ala Met Asp Asp Ala Trp Leu Glu
                85                  90                  95

Arg Val Val Asp Gln Glu Glu Ala Asp Gly Arg Phe Asn Thr Pro Glu
                100                 105                 110

Ala Lys Ala Ala Asn His Lys Gly Arg Thr Tyr Ala Ala Asp Met His
            115                 120                 125

Arg Val Asp Leu Lys Asp Asp Asp Gln Trp Met Ala Lys Gln Val Tyr
            130                 135                 140

Leu Asn Val Gly Asn Phe Leu Leu Gly Val Gly Ala Met Gly Leu Asp
145                 150                 155                 160

Ala Val Pro Ile Glu Gly Phe Asp Ala Ala Ile Leu Asp Glu Glu Phe
                165                 170                 175

Gly Leu Lys Glu Lys Gly Phe Thr Ser Leu Val Val Val Pro Val Gly
            180                 185                 190

His His Ser Val Glu Asp Phe Asn Ala Thr Leu Pro Lys Ser Arg Leu
            195                 200                 205

Pro Leu Ser Thr Ile Val Thr Glu Cys
    210                 215
```

<210> SEQ ID NO 39
<211> LENGTH: 654
<212> TYPE: DNA
<213> ORGANISM: Artificial Sequence
<220> FEATURE:
<223> OTHER INFORMATION: nucleotide sequence encoding variant of
      Enterobacter cloacae nitroreductase

<400> SEQUENCE: 39

```
atggatatca tttctgtcgc cctgaaacgc cactctacca aggcgttcga cgcaagcaaa        60
aaactgaccg cggaagaagc ggaaaaaatc aaaaccctgc tgcagtacag cccgtccgca       120
ataaactccc agccgtggca cttcattgta gccagcaccg aggaaggaaa agcgcgcgtg       180
gcgaagtccg ctgcgggcac ctatgtgttc aacgaacgca aaatgctgga tgcttcccac       240
gtggtggtgt tctgcgcgaa aaccgcgatg gatgacgcct ggctggagcg cgtcgtggat       300
caggaagagg ccgatggccg tttcaacacg ccggaagcca agccgcaaa ccataagggc        360 cgcacctacg cagccgacat gcaccgcgtg gatctgaaag atgacgacca gtggatggcg       420
```

```
aagcaggttt acctgaacgt cggcaacttc ctgctgggcg tgggcgcgat gggtctggac      480
gcggtaccaa ttgaaggttt cgacgccgct attctcgacg aagagtttgg cctgaaagag      540
aaaggcttca ccagcctggt ggtggtaccg gttgggcacc acagcgtgga agatttcaac      600
gccacgctgc cgaaatctcg cctgccgctg agcacgattg tgaccgagtg ctaa            654
```

```
<210> SEQ ID NO 40
<211> LENGTH: 217
<212> TYPE: PRT
<213> ORGANISM: Artificial Sequence
<220> FEATURE:
<223> OTHER INFORMATION: no acid variant of Enterobacter cloacae
      nitroreductase

<400> SEQUENCE: 40

Met Asp Ile Ile Ser Val Ala Leu Lys Arg His Ser Thr Lys Ala Phe
1               5                   10                  15

Asp Ala Ser Lys Lys Leu Thr Ala Glu Glu Ala Glu Lys Ile Lys Thr
            20                  25                  30

Leu Leu Gln Tyr Ser Pro Ser Ser Leu Asn Ser Gln Pro Trp His Phe
        35                  40                  45

Ile Val Ala Ser Thr Glu Glu Gly Lys Ala Arg Val Ala Lys Ser Ala
    50                  55                  60

Ala Gly Thr Leu Val Phe Asn Glu Arg Lys Met Leu Asp Ala Ser His
65                  70                  75                  80

Val Val Val Phe Cys Ala Lys Thr Ala Met Asp Asp Ala Trp Leu Glu
                85                  90                  95

Arg Val Val Asp Gln Glu Glu Ala Asp Gly Arg Phe Asn Thr Pro Glu
            100                 105                 110

Ala Lys Ala Ala Asn His Lys Gly Arg Thr Tyr Leu Ala Asp Met His
            115                 120                 125

Arg Val Asp Leu Lys Asp Asp Asp Gln Trp Met Ala Lys Gln Val Tyr
        130                 135                 140

Leu Asn Val Gly Asn Phe Leu Leu Gly Val Gly Ala Met Gly Leu Asp
145                 150                 155                 160

Ala Val Pro Ile Glu Gly Phe Asp Ala Ala Ile Leu Asp Glu Glu Phe
                165                 170                 175

Gly Leu Lys Glu Lys Gly Phe Thr Ser Leu Val Val Val Pro Val Gly
            180                 185                 190

His His Ser Val Glu Asp Phe Asn Ala Thr Leu Pro Lys Ser Arg Leu
            195                 200                 205

Pro Leu Ser Thr Ile Val Thr Glu Cys
    210                 215
```

```
<210> SEQ ID NO 41
<211> LENGTH: 654
<212> TYPE: DNA
<213> ORGANISM: Artificial Sequence
<220> FEATURE:
<223> OTHER INFORMATION: Sequence encoding variant of nitroreductase

<400> SEQUENCE: 41
atggatatca tttctgtcgc cctgaaacgc cactctacca aggcgttcga cgcaagcaaa       60
aaactgaccg cggaagaagc ggaaaaaatc aaaaccctgc tgcagtacag cccgtcctca      120
ctaaactccc agccgtggca cttcattgta gccagcaccg aggaaggaaa agcgcgcgtg      180
gcgaagtccg ctgcgggcac ccttgtgttc aacgaacgca aaatgctgga tgcttcccac      240
```

-continued

```
gtggtggtgt tctgcgcgaa aaccgcgatg gatgacgcct ggctggagcg cgtcgtggat        300
caggaagagg ccgatggccg tttcaacacg ccggaagcca aagccgcaaa ccataagggc        360
cgcacctacc tcgccgacat gcaccgcgtg gatctgaaag atgacgacca gtggatggcg        420
aagcaggttt acctgaacgt cggcaacttc ctgctgggcg tgggcgcgat gggtctggac        480
gcggtaccaa ttgaaggttt cgacgccgct attctcgacg aagagtttgg cctgaaagag        540
aaaggcttca ccagcctggt ggtggtaccg gttgggcacc acagcgtgga agatttcaac        600
gccacgctgc cgaaatctcg cctgccgctg agcacgattg tgaccgagtg ctaa        654
```

```
<210> SEQ ID NO 42
<211> LENGTH: 49
<212> TYPE: DNA
<213> ORGANISM: Artificial Sequence
<220> FEATURE:
<223> OTHER INFORMATION: oligoLS294

<400> SEQUENCE: 42
gcagccatat gatgaaaggc tttgccatgc tgggtattaa caaattagg        49
```

```
<210> SEQ ID NO 43
<211> LENGTH: 63
<212> TYPE: DNA
<213> ORGANISM: Artificial Sequence
<220> FEATURE:
<223> OTHER INFORMATION: oligoLS295

<400> SEQUENCE: 43
ttattgctca gcttagagga taactacggc cttaatgaga tctttaggtt tatctttcat        60
gag        63
```

```
<210> SEQ ID NO 44
<211> LENGTH: 23
<212> TYPE: DNA
<213> ORGANISM: Artificial Sequence
<220> FEATURE:
<223> OTHER INFORMATION: oligoLS344

<400> SEQUENCE: 44
acgataatat cgctgcgttt aac        23
```

```
<210> SEQ ID NO 45
<211> LENGTH: 22
<212> TYPE: DNA
<213> ORGANISM: Artificial Sequence
<220> FEATURE:
<223> OTHER INFORMATION: oligoLS345

<400> SEQUENCE: 45
ctggcaaaac tgggcgcaca tc        22
```

```
<210> SEQ ID NO 46
<211> LENGTH: 41
<212> TYPE: DNA
<213> ORGANISM: Artificial Sequence
<220> FEATURE:
<223> OTHER INFORMATION: oligoLS342

<400> SEQUENCE: 46
cggttcgcta cgggcttttt catattccca caccgtggtc g        41
```

```
<210> SEQ ID NO 47
```

```
<211> LENGTH: 49
<212> TYPE: DNA
<213> ORGANISM: Artificial Sequence
<220> FEATURE:
<223> OTHER INFORMATION: oligoLS343

<400> SEQUENCE: 47
ggttaatgtg attgattatg acacctctga tcaggttctg cgccaagac                49

<210> SEQ ID NO 48
<211> LENGTH: 23
<212> TYPE: DNA
<213> ORGANISM: Artificial Sequence
<220> FEATURE:
<223> OTHER INFORMATION: oligoLS344

<400> SEQUENCE: 48
acgataatat cgctgcgttt aac                                            23

<210> SEQ ID NO 49
<211> LENGTH: 22
<212> TYPE: DNA
<213> ORGANISM: Artificial Sequence
<220> FEATURE:
<223> OTHER INFORMATION: oligoLS345

<400> SEQUENCE: 49
ctggcaaaac tgggcgcaca tc                                             22

<210> SEQ ID NO 50
<211> LENGTH: 49
<212> TYPE: DNA
<213> ORGANISM: Artificial Sequence
<220> FEATURE:
<223> OTHER INFORMATION: oligoLS343

<400> SEQUENCE: 50
ggttaatgtg attgattatg acacctctga tcaggttctg cgccaagac                49

<210> SEQ ID NO 51
<211> LENGTH: 41
<212> TYPE: DNA
<213> ORGANISM: Artificial Sequence
<220> FEATURE:
<223> OTHER INFORMATION: oligoLS346

<400> SEQUENCE: 51
cggttcgctc gcggcttttt catattccca caccgtggtc g                        41

<210> SEQ ID NO 52
<211> LENGTH: 64
<212> TYPE: DNA
<213> ORGANISM: Artificial Sequence
<220> FEATURE:
<223> OTHER INFORMATION: oligoLS337
<220> FEATURE:
<221> NAME/KEY: misc_feature
<222> LOCATION: (26)..(34)
<223> OTHER INFORMATION: n is a, c, g, or t
<220> FEATURE:
<221> NAME/KEY: misc_feature
<222> LOCATION: (41)..(43)
<223> OTHER INFORMATION: n is a, c, g, or t

<400> SEQUENCE: 52
gctgagaaga ccgaccacgg tgtggnnnnn nnnnaaagcc nnnagcgaac cgctggcaaa      60
actg                                                                 64
```

```
<210> SEQ ID NO 53
<211> LENGTH: 68
<212> TYPE: DNA
<213> ORGANISM: Artificial Sequence
<220> FEATURE:
<223> OTHER INFORMATION: oligoLS338

<400> SEQUENCE: 53
gctgagaaga ccgtggtcgt gtagccagat tgcaggaatg ctttaatcag tgcggagccc      60
atacggcc                                                               68

<210> SEQ ID NO 54
<211> LENGTH: 63
<212> TYPE: DNA
<213> ORGANISM: Artificial Sequence
<220> FEATURE:
<223> OTHER INFORMATION: oligoLS358

<400> SEQUENCE: 54
tctctgaaga ctccttagtg gtggtggtgg tggtgtttca ggaagcgggt cagaattgca      60
aag                                                                    63

<210> SEQ ID NO 55
<211> LENGTH: 41
<212> TYPE: DNA
<213> ORGANISM: Artificial Sequence
<220> FEATURE:
<223> OTHER INFORMATION: oligoLS359

<400> SEQUENCE: 55
tctctgaaga caacatgaaa ccgaccctga ccgttattgg c                          41

<210> SEQ ID NO 56
<211> LENGTH: 63
<212> TYPE: DNA
<213> ORGANISM: Artificial Sequence
<220> FEATURE:
<223> OTHER INFORMATION: oligoLS358

<400> SEQUENCE: 56
tctctgaaga ctccttagtg gtggtggtgg tggtgtttca ggaagcgggt cagaattgca      60
aag                                                                    63

<210> SEQ ID NO 57
<211> LENGTH: 41
<212> TYPE: DNA
<213> ORGANISM: Artificial Sequence
<220> FEATURE:
<223> OTHER INFORMATION: oligoLS359

<400> SEQUENCE: 57
tctctgaaga caacatgaaa ccgaccctga ccgttattgg c                          41

<210> SEQ ID NO 58
<211> LENGTH: 63
<212> TYPE: DNA
<213> ORGANISM: Artificial Sequence
<220> FEATURE:
<223> OTHER INFORMATION: oligoLS358

<400> SEQUENCE: 58
tctctgaaga ctccttagtg gtggtggtgg tggtgtttca ggaagcgggt cagaattgca      60
``` aag                                                                                          63

<210> SEQ ID NO 59
<211> LENGTH: 41
<212> TYPE: DNA
<213> ORGANISM: Artificial Sequence
<220> FEATURE:
<223> OTHER INFORMATION: oligoLS359

<400> SEQUENCE: 59
tctctgaaga caacatgaaa ccgaccctga ccgttattgg c                        41

<210> SEQ ID NO 60
<211> LENGTH: 71
<212> TYPE: DNA
<213> ORGANISM: Artificial Sequence
<220> FEATURE:
<223> OTHER INFORMATION: oligoLS363
<220> FEATURE:
<221> NAME/KEY: misc_feature
<222> LOCATION: (50)..(55)
<223> OTHER INFORMATION: n is a, c, g, or t

<400> SEQUENCE: 60
tctctgaaga ctcggtgctg gctacaatga agtgccacgg ctgggagttn nnnnnggacg    60
ggctgtactg c                                                          71

<210> SEQ ID NO 61
<211> LENGTH: 45
<212> TYPE: DNA
<213> ORGANISM: Artificial Sequence
<220> FEATURE:
<223> OTHER INFORMATION: oligoLS366

<400> SEQUENCE: 61
ctctgaagac cagtggatgg cgaagcaggt ttacctgaac gtcgg                    45

<210> SEQ ID NO 62
<211> LENGTH: 75
<212> TYPE: DNA
<213> ORGANISM: Artificial Sequence
<220> FEATURE:
<223> OTHER INFORMATION: oligoLS364
<220> FEATURE:
<221> NAME/KEY: misc_feature
<222> LOCATION: (59)..(61)
<223> OTHER INFORMATION: n is a, c, g, or t

<400> SEQUENCE: 62
ctctgaagac agcaccgagg aaggaaaagc gcgcgtggcg aagtccgctg cgggcaccnn    60
ngtgttcaac gaacg                                                      75

<210> SEQ ID NO 63
<211> LENGTH: 70
<212> TYPE: DNA
<213> ORGANISM: Artificial Sequence
<220> FEATURE:
<223> OTHER INFORMATION: oligoLS365
<220> FEATURE:
<221> NAME/KEY: misc_feature
<222> LOCATION: (56)..(58)
<223> OTHER INFORMATION: n is a, c, g, or t

<400> SEQUENCE: 63
tctctgaaga catccactgg tcgtcatctt tcagatccac gcggtgcatg tcggcnnngt    60
aggtgcggcc                                                            70

-continued

```
<210> SEQ ID NO 64
<211> LENGTH: 58
<212> TYPE: DNA
<213> ORGANISM: Artificial Sequence
<220> FEATURE:
<223> OTHER INFORMATION: oligoLS230

<400> SEQUENCE: 64
aaggggttgg tctcatgtgc tcttcgatga aaaattgtgt catcgtcagt gcggtacg          58

<210> SEQ ID NO 65
<211> LENGTH: 65
<212> TYPE: DNA
<213> ORGANISM: Artificial Sequence
<220> FEATURE:
<223> OTHER INFORMATION: oligoLS231

<400> SEQUENCE: 65
aaggggttgg tctctggtct tacgctcttc attaattcaa ccgttcaatc accatcgcaa         60
ttccc                                                                     65

<210> SEQ ID NO 66
<211> LENGTH: 58
<212> TYPE: DNA
<213> ORGANISM: Artificial Sequence
<220> FEATURE:
<223> OTHER INFORMATION: oligoLS234

<400> SEQUENCE: 66
aaggggttgg tctcatgtgg ctcttcgatg aaaacaaaat tgatgacatt acaagacg          58

<210> SEQ ID NO 67
<211> LENGTH: 61
<212> TYPE: DNA
<213> ORGANISM: Artificial Sequence
<220> FEATURE:
<223> OTHER INFORMATION: oligoLS243

<400> SEQUENCE: 67
aaggggttgg tctctggtct tacgctcttc attatttgct ctcctgtgaa acgatgatgt         60
g                                                                         61

<210> SEQ ID NO 68
<211> LENGTH: 56
<212> TYPE: DNA
<213> ORGANISM: Artificial Sequence
<220> FEATURE:
<223> OTHER INFORMATION: oligoLS235

<400> SEQUENCE: 68
aaggggttgg tctctggtct tacgctcttc attataaatc accccgttgc gtattc            56

<210> SEQ ID NO 69
<211> LENGTH: 52
<212> TYPE: DNA
<213> ORGANISM: Artificial Sequence
<220> FEATURE:
<223> OTHER INFORMATION: oligoLS242

<400> SEQUENCE: 69
aaggggttgg tctcatgtgg ctcttcgatg gatgcgaaac aacgtattgc gc               52

<210> SEQ ID NO 70
```

```
<211> LENGTH: 63
<212> TYPE: DNA
<213> ORGANISM: Artificial Sequence
<220> FEATURE:
<223> OTHER INFORMATION: oligoLS228

<400> SEQUENCE: 70
aaggggttgg tctcatgtgg ctcttcgatg ttaaaggatg aagtaattaa acaaattagc        60
acg                                                                      63

<210> SEQ ID NO 71
<211> LENGTH: 68
<212> TYPE: DNA
<213> ORGANISM: Artificial Sequence
<220> FEATURE:
<223> OTHER INFORMATION: oligoLS229

<400> SEQUENCE: 71
aaggggttgg tctctggtct tacgctcttc attacttaag ataatcatat ataacttcag        60
ctctaggc                                                                 68

<210> SEQ ID NO 72
<211> LENGTH: 57
<212> TYPE: DNA
<213> ORGANISM: Artificial Sequence
<220> FEATURE:
<223> OTHER INFORMATION: oligoLS232

<400> SEQUENCE: 72
aaggggttgg tctcatgtgg ctcttcgatg aaaggctttg ccatgctggg tattaac           57

<210> SEQ ID NO 73
<211> LENGTH: 67
<212> TYPE: DNA
<213> ORGANISM: Artificial Sequence
<220> FEATURE:
<223> OTHER INFORMATION: oligoLS233

<400> SEQUENCE: 73
aaggggttgg tctctggtct tacgctcttc attagaggat aactacggcc ttaatgagat        60
ctttagg                                                                  67

<210> SEQ ID NO 74
<211> LENGTH: 33
<212> TYPE: DNA
<213> ORGANISM: Artificial Sequence
<220> FEATURE:
<223> OTHER INFORMATION: oligoLS244

<400> SEQUENCE: 74
ttcagcggat cctgtctgtt ttgcggtcgc cag                                     33

<210> SEQ ID NO 75
<211> LENGTH: 46
<212> TYPE: DNA
<213> ORGANISM: Artificial Sequence
<220> FEATURE:
<223> OTHER INFORMATION: oligoLS247

<400> SEQUENCE: 75
cactggagaa agtcttatgt aatcttgccg ctcccctgca ttccag                       46

<210> SEQ ID NO 76
<211> LENGTH: 37
```

```
<212> TYPE: DNA
<213> ORGANISM: Artificial Sequence
<220> FEATURE:
<223> OTHER INFORMATION: oligoLS245

<400> SEQUENCE: 76
ttcagcaagc ttcaagcaga atcaagttct accgtgc                                    37

<210> SEQ ID NO 77
<211> LENGTH: 48
<212> TYPE: DNA
<213> ORGANISM: Artificial Sequence
<220> FEATURE:
<223> OTHER INFORMATION: oligoLS246

<400> SEQUENCE: 77
caggggagcg gcaagattac ataagacttt ctccagtgat gttgaatc                        48

<210> SEQ ID NO 78
<211> LENGTH: 50
<212> TYPE: DNA
<213> ORGANISM: Artificial Sequence
<220> FEATURE:
<223> OTHER INFORMATION: oligoLS208

<400> SEQUENCE: 78
ttcagcggat ccaatgtatc tgcatgaagc acagacccac cagttactgg                      50

<210> SEQ ID NO 79
<211> LENGTH: 57
<212> TYPE: DNA
<213> ORGANISM: Artificial Sequence
<220> FEATURE:
<223> OTHER INFORMATION: oligoLS210

<400> SEQUENCE: 79
aacaggtaag ccctaccatg taaaacttta tcgaaatggc catccattct tgcgcgg             57

<210> SEQ ID NO 80
<211> LENGTH: 52
<212> TYPE: DNA
<213> ORGANISM: Artificial Sequence
<220> FEATURE:
<223> OTHER INFORMATION: oligoLS209

<400> SEQUENCE: 80
ttcagcaagc ttcattaaac cgctctcatc aaccatggtc agacccagtt cg                   52

<210> SEQ ID NO 81
<211> LENGTH: 65
<212> TYPE: DNA
<213> ORGANISM: Artificial Sequence
<220> FEATURE:
<223> OTHER INFORMATION: oligoLS211

<400> SEQUENCE: 81
gccatttcga taaagtttta catggtaggg cttacctgtt cttatacata aaagcaacag          60
aatgg                                                                       65

<210> SEQ ID NO 82
<211> LENGTH: 37
<212> TYPE: DNA
<213> ORGANISM: Artificial Sequence
<220> FEATURE:
<223> OTHER INFORMATION: oligLS216
```

-continued

```
<400> SEQUENCE: 82
ttcagcggat ccgaaacgac cagagccgcc aggttca                              37

<210> SEQ ID NO 83
<211> LENGTH: 75
<212> TYPE: DNA
<213> ORGANISM: Artificial Sequence
<220> FEATURE:
<223> OTHER INFORMATION: oligLS217

<400> SEQUENCE: 83
ccgatggaag ggaatatcat gtaaggggta acatatgtct ggaggattag ttacagctgc     60
atacattgtt gccgc                                                      75

<210> SEQ ID NO 84
<211> LENGTH: 62
<212> TYPE: DNA
<213> ORGANISM: Artificial Sequence
<220> FEATURE:
<223> OTHER INFORMATION: oligoLS218

<400> SEQUENCE: 84
ttcagcaagc ttcaggaggg tgttcttaag cttcataaaa ataatccttc gccttgcgca     60
aa                                                                    62

<210> SEQ ID NO 85
<211> LENGTH: 53
<212> TYPE: DNA
<213> ORGANISM: Artificial Sequence
<220> FEATURE:
<223> OTHER INFORMATION: oligoLS219

<400> SEQUENCE: 85
ccagacatat gttacccctt acatgatatt cccttccatc ggtttattg atg            53

<210> SEQ ID NO 86
<211> LENGTH: 915
<212> TYPE: DNA
<213> ORGANISM: Artificial Sequence
<220> FEATURE:
<223> OTHER INFORMATION: gBlockLS10

<400> SEQUENCE: 86
ccgttcgcat gcaggaggta cgaacacatg aaaccgaccc tgaccgttat tggcgctggc     60
cgtatgggct ccgcactgat taaagcattc ctgcaatctg ctacacgac cacggtgtgg     120 aaccgtacca aagccaaaag cgaaccgctg gcaaaactgg gcgcacatct ggctgatacg     180
gtgcgtgacg ccgttaaacg cagcgatatt atcgtggtta atgtgctgga ttatgacacc     240
tctgatcagc tgctgcgcca agacgaagtg acgcgtgaac tgcgcggcaa actgctggtt     300
cagctgacca gcggttctcc ggcactggct cgtgaacagg aaacgtgggc gcgccaacat     360
ggcattgatt atctggacgg tgcgatcatg gccaccccgg attttattgg ccaggcagaa     420
tgcgctctgc tgtacagtgg ttccgcggcc ctgttcgaaa acaccgtgc tgtcctgaat      480 gtgctgggcg gtgccaccag ccatgtcggc gaagatgttg tcatgccctc agcactggac     540
agcgccctgc tgtttcagat gtggggcacc ctgttcggta cgctgcaagc actggctatt     600
tctcgcgcag aaggcatccc gctggaaaaa accacggcgt ttatcaaact gaccgaaccg     660
gtcacccagg tgccgttgc agatgtcctg acccgtgttc agcaaaatcg cctgaccgca      720
gacgctcaga cgctggcaag tctggaagct cataacgtgg cgttccaaca cctgctggcc     780
```
ctgtgtgaag aacgtaatat ccatcgcggt gttgcggatg ccatgtactc cgttattcgt      840
gaagcggtca aagccggcca cggtaaagat gactttgcaa ttctgacccg cttcctgaaa      900
taaggatcct tcagc                                                       915

<210> SEQ ID NO 87
<211> LENGTH: 682
<212> TYPE: DNA
<213> ORGANISM: Artificial Sequence
<220> FEATURE:
<223> OTHER INFORMATION: gBlockLS12

<400> SEQUENCE: 87
catctgaaga caacatggat atcatttctg tcgccctgaa acgccactct accaaggcgt       60
tcgacgcaag caaaaaactg accgcggaag aagcggaaaa aatcaaaacc ctgctgcagt      120
acagcccgtc cagcaccaac tcccagccgt ggcacttcat tgtagccagc accgaggaag      180
gaaaagcgcg cgtggcgaag tccgctgcgg gcacctatgt gttcaacgaa cgcaaaatgc      240
tggatgcttc ccacgtggtg gtgttctgcg cgaaaaccgc gatggatgac gcctggctgg      300
agcgcgtcgt ggatcaggaa gaggccgatg gccgtttcaa cacgccggaa gccaaagccg      360
caaaccataa gggccgcacc tacttcgccg acatgcaccg cgtggatctg aaagatgacg      420
accagtggat ggcgaagcag gtttacctga acgtcggcaa cttcctgctg ggcgtgggcg      480
cgatgggtct ggacgcggta ccaattgaag gtttcgacgc cgctattctc gacgaagagt      540
ttggcctgaa agagaaaggc ttcaccagcc tggtggtggt accggttggg caccacagcg      600
tggaagattt caacgccacg ctgccgaaat ctcgcctgcc gctgagcacg attgtgaccg      660
agtgctaagg agtcttcaga ga                                              682

<210> SEQ ID NO 88
<211> LENGTH: 4994
<212> TYPE: DNA
<213> ORGANISM: Artificial Sequence
<220> FEATURE:
<223> OTHER INFORMATION: variant isopropanol metabolic pathway encoding
      sequence

<400> SEQUENCE: 88
ttgacagcta gctcagtcct agggactatg ctagcccact acgtttttta gaaaaaggag       60
gtatgcgaga tgaaaaattg tgtcatcgtc agtgcggtac gtactgctat cggtagtttt      120
aacggttcac tcgcttccac cagcgccatc gacctggggg cgacagtaat aaagccgcc       180 attgaacgtg caaaaatcga ttcacaacac gttgatgaag tgattatggg taacgtgtta      240
caagccgggc tggggcaaaa tccggcgcgt caggcactgt aaaaagcgg ctggcagaa       300 acggtgtgcg gattcacggt caataaagta tgtggttcgg gtcttaaaag tgtggcgctt      360
gccgcccagg ccattcaggc aggtcaggcg cagagcattg tggcgggggg tatggaaaat      420
atgagtttag ccccctactt actcgatgca aaagcacgct ctggttatcg tcttggagac      480
ggacaggttt atgacgtaat cctgcgcgat ggcctgatgt gcgccaccca tggttatcat      540
atggggatta ccgccgaaaa cgtggctaaa gagtacggaa ttacccgtga atgcaggat       600 gaactggcgc tacattcaca gcgtaaagcg gcagccgcaa ttgagtccgg tgcttttaca      660
gccgaaatcg tcccggtaaa tgttgtcact cgaaagaaaa ccttcgtgtt cagtcaagac      720
gaattcccga aagcgaattc aacggctgaa gcgttaggtg cattgcgccc ggccttcgat      780
aaagcaggaa cagtcaccgc tgggaacgcg tctggtatta cgacggtgc tgccgctctg      840

```
gtgattatgg aagaatctgc ggcgctggca gcaggcctta cccccctggc tcgcattaaa      900
agttatgcca gcggtggcgt gccccccgca ttgatgggta tggggccagt acctgccacg      960
caaaaagcgt tacaactggc ggggctgcaa ctggcggata ttgatctcat tgaggctaat     1020
gaagcatttg ctgcacagtt ccttgccgtt gggaaaaacc tgggctttga ttctgagaaa     1080
gtgaatgtca acggcggggc catcgcgctc gggcatccta tcggtgccag tggtgctcgt     1140
attctggtca cactattaca tgccatgcag gcacgcgata aaacgctggg gctggcaaca     1200
ctgtgcattg gcggcggtca gggaattgcg atggtgattg aacggttgaa ttaactcggt     1260
accaaagacg aacaataaga cgctgaaaag cgtctttttt cgttttggtc cggaaatgca     1320
gctgatggct agctcagtcc tagggattat gctagcccac tacgtttttt agaaaaagga     1380
ggtatgcgag atgaaaacaa aattgatgac attacaagac gccaccggct tctttcgtga     1440
cggcatgacc atcatggtgg gcggatttat ggggattggc actccatccc gcctggttga     1500
agcattactg gaatctggtg ttcgcgacct gacattgata gccaatgata ccgcgtttgt     1560
tgataccggc atcggtccgc tcatcgtcaa tggtcgagtc cgcaaagtga ttgcttcaca     1620
tatcggcacc aacccggaaa caggtcggcg catgatatct ggtgagatgg acgtcgttct     1680
ggtgccgcaa ggtacgctaa tcgagcaaat tcgctgtggt ggagctggac ttggtggttt     1740
tctcacccca acgggtgtcg gcaccgtcgt agaggaaggc aaacagacac tgacactcga     1800
cggtaaaacc tggctgctcg aacgcccact gcgcgccgac ctggcgctaa ttcgcgctca     1860
tcgttgcgac acacttggca acctgaccta tcaacttagc gcccgcaact ttaaccccct     1920
gatagccctt gcggctgata tcacgctggt agagccagat gaactggtcg aaaccggcga     1980
gctgcaacct gaccatattg tcacccctgg tgccgttatc gaccacatca tcgtttcaca     2040
ggagagcaaa taactcggta ccaaattcca gaaaagaggc ctcccgaaag ggggccttt     2100 tttcgttttg gtccggaagg tcagttgaca gctagctcag tcctagggac tatgctagcc     2160
caagctcctt agctcctaaa ggaggtagta catatggatg cgaaacaacg tattgcgcgc     2220
cgtgtggcgc aagagcttcg tgatggtgac atcgttaact agggatcgg tttacccaca     2280 atggtcgcca attatttacc ggagggtatt catatcactc tgcaatcgga aaacggcttc     2340
ctcggtttag gcccggtcac gacagcgcat ccagatctgg tgaacgctgg cgggcaaccg     2400
tgcggtgttt tacccggtgc agccatgttt gatagcgcca tgtcatttgc gctaatccgt     2460
ggcggtcata ttgatgcctg cgtgctcggc ggtttgcaag tagacgaaga agcaaacctc     2520
gcgaactggg tagtgcctgg gaaaatggtg cccggtatgg gtggcgcgat ggatctggtg     2580
accgggtcgc gcaaagtgat catcgccatg gaacattgcg ccaaagatgg ttcagcaaaa     2640
attttgcgcc gctgcaccat gccactcact gcgcaacatg cggtgcatat gctggttact     2700
gaactggctg tctttcgttt tattgacggc aaaatgtggc tcaccgaaat tgccgacggg     2760
tgtgatttag ccaccgtgcg tgccaaaaca gaagctcggt ttgaagtcgc cgccgatctg     2820
aatacgcaac ggggtgattt aggaaacaca gaaaaaagcc cgcacctgac agtgcgggct     2880 tttttttttcg accaaagggg agcttcagtt gacggctagc tcagtcctag gtacagtgct     2940
agcccacatg atcgaatgat taaaggaggt tggaggtatg ttaaaggatg aagtaattaa     3000
acaaattagc acgccattaa cttcgcctgc atttcctaga ggaccctata aatttcataa     3060
tcgtgagtat tttaacattg tatatcgtac agatatggat gcacttcgta aagttgtgcc     3120 agagcctttta gaaattgatg agcccttagt caggtttgaa attatggcaa tgcatgatac     3180
```

-continued

```
gagtggactt ggttgttata cagaaagcgg acaggctatt cccgtaagct ttaatggagt      3240
taagggagat tatcttcata tgatgtattt agataatgag cctgcaattg cagtaggaag      3300
ggaattaagt gcatatccta aaaagctcgg gtatccaaag cttttttgtgg attcagatac     3360 tttagtagga actttagact atggaaaact tagagttgcg acagctacaa tggggtacaa      3420
acataaagcc ttagatgcta atgaagcaaa ggatcaaatt tgtcgcccta attatatgtt      3480
gaaaataata cccaattatg atggaagccc tagaatatgt gagcttataa atgcgaaaat      3540
cacagatgtt accgtacatg aagcttggac aggaccaact cgactgcagt tatttgatca      3600
cgctatggcg ccacttaatg atttgccagt aaaagagatt gtttctagct ctcacattct      3660
tgcagatata atattgccta gagctgaagt tatatatgat tatcttaagt aattcagcca      3720
aaaaacttaa gaccgccggt cttgtccact accttgcagt aatgcggtgg acaggatcgg      3780 cggtttttctt ttctcttctc aaggacgctc agctgatggc tagctcagtc ctagggatta     3840
tgctagccca acaggataca tctgtaaagg aggtaacgat gatgaaaggc tttgccatgc      3900
tgggtattaa caaattagga tggattgaaa aagaacgccc cgtcgcgggt tcctatgatg      3960
cgattgtacg acccttagcc gtttccccgt gcactagcga tattcataca gtatttgaag      4020
gggctctcgg cgatcgaaag aatatgattt taggccatga agccgttggc gaagtcgttg      4080
aagtgggctc cgaagtgaaa gatttcaaac cgggtgaccg tgtcatcgtg ccctgtacta      4140
ccccagattg gcgctctctg gaggttcaag ctggttttca acaacatagt aatggtatgt      4200
tggccggctg gaagttttcc aacttcaaag atggagtatt tggggagtat tttcatgtga      4260
acgatgcgga tatgaatttg gccatcctgc caaaagacat gccccttggag aatgctgtaa     4320 tgatcaccga tatgatgacc accggatttc atggggccga gttggccgat atccagatgg      4380
gtagttctgt cgttgtgatt ggtatcgggg cagttgggtt aatgggaatt gctggggcca      4440
aattacgcgg agcaggtcgg attattggtg tcggcagtcg gcctatttgc gttgaggccg      4500
ccaagttcta cggcgcgacc gacattctga attacaaaaa tggccatatt gtggaccagg      4560
taatgaagct aaccaatggg aaaggcgtgg accgtgtgat tatggctgga ggtgggagtg      4620
aaacactgag ccaagcagtg agcatggtga aacctggggg aattatcagc aatatcaact      4680
atcacggctc tggtgacgct ttgttaattc cccgcgtgga atggggatgt ggcatggcgc      4740
acaagacgat caaaggcggt ttgtgtcccg gaggccgttt acgggccgaa atgctacggg      4800
atatggtggt gtacaaccgt gtggatttgt ccaagctggt gactcacgtt tatcacggtt      4860
ttgaccatat tgaagaagcc ttgctactca tgaaagataa acctaaagat ctcattaagg      4920
ccgtagttat cctctaactc ggtaccaaag acgaacaata agacgctgaa aagcgtcttt      4980
tttcgttttg gtcc                                                         4994
```

```
<210> SEQ ID NO 89
<211> LENGTH: 4994
<212> TYPE: DNA
<213> ORGANISM: Artificial Sequence
<220> FEATURE:
<223> OTHER INFORMATION: variant isopropanol metabolic pathway encoding
      sequence

<400> SEQUENCE: 89
ttgacagcta gctcagtcct agggactatg ctagcccaaa aacactagac tggaaaggag       60
gtagagaata tgaaaaattg tgtcatcgtc agtgcggtac gtactgctat cggtagtttt      120
aacggttcac tcgcttccac cagcgccatc gacctggggg cgacagtaat taaagccgcc      180
```

-continued

```
attgaacgtg caaaaatcga ttcacaacac gttgatgaag tgattatggg taacgtgtta    240
caagccgggc tggggcaaaa tccggcgcgt caggcactgt taaaaagcgg gctggcagaa    300
acggtgtgcg gattcacggt caataaagta tgtggttcgg gtcttaaaag tgtggcgctt    360
gccgcccagg ccattcaggc aggtcaggcg cagagcattg tggcggggg tatggaaaat    420 atgagtttag cccctactt actcgatgca aaagcacgct ctggttatcg tcttggagac    480
ggacaggttt atgacgtaat cctgcgcgat ggcctgatgt gcgccaccca tggttatcat    540
atggggatta ccgccgaaaa cgtggctaaa gagtacggaa ttacccgtga aatgcaggat    600
gaactggcgc tacattcaca gcgtaaagcg gcagccgcaa ttgagtccgg tgcttttaca    660
gccgaaatcg tcccggtaaa tgttgtcact cgaaagaaaa ccttcgtgtt cagtcaagac    720
gaattcccga aagcgaattc aacggctgaa gcgttaggtg cattgcgccc ggccttcgat    780
aaagcaggaa cagtcaccgc tgggaacgcg tctggtatta cgacggtgc tgccgctctg    840 gtgattatgg aagaatctgc ggcgctggca gcaggcctta cccccctggc tcgcattaaa    900
agttatgcca gcggtggcgt gccccccgca ttgatgggta tggggccagt acctgccacg    960
caaaaagcgt tacaactggc ggggctgcaa ctggcggata ttgatctcat tgaggctaat   1020
gaagcatttg ctgcacagtt ccttgccgtt gggaaaaacc tgggctttga ttctgagaaa   1080
gtgaatgtca acggcggggc catcgcgctc gggcatccta tcggtgccag tggtgctcgt   1140
attctggtca cactattaca tgccatgcag gcacgcgata aaacgctggg gctggcaaca   1200
ctgtgcattg gcggcggtca gggaattgcg atggtgattg aacggttgaa ttaactcggt   1260
accaaagacg aacaataaga cgctgaaaag cgtctttttt cgttttggtc cggaaatgca   1320
gctgatggct agctcagtcc tagggattat gctagcccaa caggatacat ctgtaaagga   1380
ggtaacgatg atgaaaacaa aattgatgac attacaagac gccaccggct tctttcgtga   1440
cggcatgacc atcatggtgg gcggatttat ggggattggc actccatccc gcctggttga   1500
agcattactg gaatcggtg ttcgcgacct gacattgata gccaatgata ccgcgtttgt   1560
tgataccggc atcggtccgc tcatcgtcaa tggtcgagtc cgcaaagtga ttgcttcaca   1620
tatcggcacc aacccggaaa caggtcggcg catgatatct ggtgagatgg acgtcgttct   1680
ggtgccgcaa ggtacgctaa tcgagcaaat tcgctgtggt ggagctggac ttggtggttt   1740
tctcacccca acgggtgtcg gcaccgtcgt agaggaaggc aaacagacac tgacactcga   1800
cggtaaaacc tggctgctcg aacgcccact gcgcgccgac ctggcgctaa ttcgcgctca   1860
tcgttgcgac acacttggca acctgaccta tcaacttagc gcccgcaact ttaacccect   1920 gatagccctt gcggctgata tcacgctggt agagccagat gaactggtcg aaaccggcga   1980
gctgcaacct gaccatattg tcacccctgg tgccgttatc gaccacatca tcgtttcaca   2040
ggagagcaaa taactcggta ccaaattcca gaaaagaggc ctcccgaaag gggggccttt   2100
tttcgttttg gtccggaagg tcagttgaca gctagctcag tcctaggtac tgtgctagcc   2160
caagctcctt agctcctaaa ggaggtagta catatggatg cgaaacaacg tattgcgcgc   2220
cgtgtggcgc aagagcttcg tgatggtgac atcgttaact tagggatcgg tttacccaca   2280
atggtcgcca attatttacc ggagggtatt catatcactc tgcaatcgga aaacggcttc   2340
ctcggtttag gcccggtcac gacagcgcat ccagatctgg tgaacgctgg cggcaaccg   2400 tgcggtgttt tacccggtgc agccatgttt gatagcgcca tgtcatttgc gctaatccgt   2460
ggcggtcata ttgatgcctg cgtgctcggc ggtttgcaag tagacgaaga agcaaacctc   2520
gcgaactggg tagtgcctgg gaaaatggtg cccggtatgg gtggcgcgat ggatctggtg   2580
```

```
accgggtcgc gcaaagtgat catcgccatg gaacattgcg ccaaagatgg ttcagcaaaa    2640
attttgcgcc gctgcaccat gccactcact gcgcaacatg cggtgcatat gctggttact    2700
gaactggctg tctttcgttt tattgacggc aaaatgtggc tcaccgaaat tgccgacggg    2760
tgtgatttag ccaccgtgcg tgccaaaaca gaagctcggt ttgaagtcgc cgccgatctg    2820
aatacgcaac ggggtgattt ataaggaaac acagaaaaaa gcccgcacct gacagtgcgg    2880
gctttttttt tcgaccaaag gggagcttca gttgacagct agctcagtcc taggtactgt    2940
gctagcccaa caggatacat ctgtaaagga ggtaacgatg atgttaaagg atgaagtaat    3000
taaacaaatt agcacgccat taacttcgcc tgcatttcct agaggaccct ataaatttca    3060
taatcgtgag tattttaaca ttgtatatcg tacagatatg gatgcacttc gtaaagttgt    3120
gccagagcct ttagaaattg atgagccctt agtcaggttt gaaattatgg caatgcatga    3180
tacgagtgga cttggttgtt atacagaaag cggacaggct attcccgtaa gctttaatgg    3240
agttaaggga gattatcttc atatgatgta tttagataat gagcctgcaa ttgcagtagg    3300
aagggaatta agtgcatatc ctaaaaagct cgggtatcca aagctttttg tggattcaga    3360
tactttagta ggaactttag actatggaaa acttagagtt gcgacagcta caatggggta    3420
caaacataaa gccttagatg ctaatgaagc aaaggatcaa atttgtcgcc ctaattatat    3480
gttgaaaata atacccaatt atgatggaag ccctagaata tgtgagctta taaatgcgaa    3540
aatcacagat gttaccgtac atgaagcttg dacaggacca actcgactgc agttatttga    3600
tcacgctatg gcgccactta atgatttgcc agtaaaagag attgtttcta gctctcacat    3660
tcttgcagat ataatattgc ctagagctga agttatatat gattatctta agttcagcca    3720
aaaaacttaa daccgccggt cttgtccact accttgcagt aatgcggtgg acaggatcgg    3780
cggttttctt ttctcttctc aaggacgctc agctgatggc tagctcagtc ctagggatta    3840
tgctagccca catgatcgaa tgattaaagg aggttggagg tatgaaaggc tttgccatgc    3900
tgggtattaa caaattagga tggattgaaa aagaacgccc cgtcgcgggt tcctatgatg    3960
cgattgtacg acccttagcc gtttcccccgt gcactagcga tattcataca gtatttgaag    4020
gggctctcgg cgatcgaaag aatatgattt taggccatga agccgttggc gaagtcgttg    4080
aagtgggctc cgaagtgaaa gatttcaaac cgggtgaccg tgtcatcgtg ccctgtacta    4140
ccccagattg gcgctctctg gaggttcaag ctggttttca acaacatagt aatggtatgt    4200
tggccggctg gaagttttcc aacttcaaag atggagtatt tggggagtat tttcatgtga    4260
acgatgcgga tatgaatttg gccatcctgc caaaagacat gccccttggag aatgctgtaa    4320 tgatcaccga tatgatgacc accggatttc atggggccga gttggccgat atccagatgg    4380
gtagttctgt cgttgtgatt ggtatcgggg cagttgggtt aatgggaatt gctgggccca    4440
aattacgcgg agcaggtcgg attattggtg tcggcagtcg gcctatttgc gttgaggccg    4500
ccaagttcta cggcgcgacc gacattctga attacaaaaa tggccatatt gtggaccagg    4560
taatgaagct aaccaatggg aaaggcgtgg accgtgtgat tatggctgga ggtgggagtg    4620
aaacactgag ccaagcagtg agcatggtga aacctggggg aattatcagc aatatcaact    4680
atcacggctc tggtgacgct ttgttaattc cccgcgtgga atggggatgt ggcatggcgc    4740
acaagacgat caaaggcggt ttgtgtcccg gaggccgttt acgggccgaa atgctacggg    4800
atatggtggt gtacaaccgt gtggatttgt ccaagctggt gactcacgtt tatcacggtt    4860
ttgaccatat tgaagaagcc ttgctactca tgaaagataa acctaaagat ctcattaagg    4920
```

-continued

```
ccgtagttat cctctaactc ggtaccaaag acgaacaata agacgctgaa aagcgtcttt    4980
tttcgttttg gtcc                                                      4994

<210> SEQ ID NO 90
<211> LENGTH: 66
<212> TYPE: DNA
<213> ORGANISM: Artificial Sequence
<220> FEATURE:
<223> OTHER INFORMATION: J23100

<400> SEQUENCE: 90
ttgacggcta gctcagtcct aggtacagtg ctagcccatg aagagcgtaa gacctctagg    60
gcggcg                                                               66

<210> SEQ ID NO 91
<211> LENGTH: 66
<212> TYPE: DNA
<213> ORGANISM: Artificial Sequence
<220> FEATURE:
<223> OTHER INFORMATION: J23102

<400> SEQUENCE: 91
ttgacagcta gctcagtcct aggtactgtg ctagcccatg aagagcgtaa gacctctagg    60
gcggcg                                                               66

<210> SEQ ID NO 92
<211> LENGTH: 66
<212> TYPE: DNA
<213> ORGANISM: Artificial Sequence
<220> FEATURE:
<223> OTHER INFORMATION: J23107

<400> SEQUENCE: 92
tttacggcta gctcagccct aggtattatg ctagcccatg aagagcgtaa gacctctagg    60
gcggcg                                                               66

<210> SEQ ID NO 93
<211> LENGTH: 66
<212> TYPE: DNA
<213> ORGANISM: Artificial Sequence
<220> FEATURE:
<223> OTHER INFORMATION: J23116

<400> SEQUENCE: 93
ttgacagcta gctcagtcct agggactatg ctagcccatg aagagcgtaa gacctctagg    60
gcggcg                                                               66

<210> SEQ ID NO 94
<211> LENGTH: 66
<212> TYPE: DNA
<213> ORGANISM: Artificial Sequence
<220> FEATURE:
<223> OTHER INFORMATION: J23113

<400> SEQUENCE: 94
ctgatggcta gctcagtcct agggattatg ctagcccatg aagagcgtaa gacctctagg    60
gcggcg                                                               66

<210> SEQ ID NO 95
<211> LENGTH: 66
<212> TYPE: DNA
<213> ORGANISM: Artificial Sequence
```

<220> FEATURE:
<223> OTHER INFORMATION: J23118

<400> SEQUENCE: 95
ttgacggcta gctcagtcct aggtattgtg ctagcccatg aagagcgtaa gacctctagg      60
gcggcg                                                                 66

<210> SEQ ID NO 96
<211> LENGTH: 62
<212> TYPE: DNA
<213> ORGANISM: Artificial Sequence
<220> FEATURE:
<223> OTHER INFORMATION: RBSc13

<400> SEQUENCE: 96
ctacgttttt tagaaaaagg aggtatgcga gatgtgaaga gcgtaagacc tctagggcgg      60
cg                                                                     62

<210> SEQ ID NO 97
<211> LENGTH: 62
<212> TYPE: DNA
<213> ORGANISM: Artificial Sequence
<220> FEATURE:
<223> OTHER INFORMATION: RBSc33

<400> SEQUENCE: 97
aaaacactag actggaaagg aggtagagaa tatgtgaaga gcgtaagacc tctagggcgg      60
cg                                                                     62

<210> SEQ ID NO 98
<211> LENGTH: 52
<212> TYPE: DNA
<213> ORGANISM: Artificial Sequence
<220> FEATURE:
<223> OTHER INFORMATION: RBSc44

<400> SEQUENCE: 98
tcgccaatcg gattggatcc aaaggaggtt ataccgatgt gaagagcgta ag             52

<210> SEQ ID NO 99
<211> LENGTH: 62
<212> TYPE: DNA
<213> ORGANISM: Artificial Sequence
<220> FEATURE:
<223> OTHER INFORMATION: RBSc58

<400> SEQUENCE: 99
ctcttcgcca catgatcgaa tgattaaagg aggttggagg tatgtgaaga gcgtaagacc      60
tc                                                                     62

<210> SEQ ID NO 100
<211> LENGTH: 50
<212> TYPE: DNA
<213> ORGANISM: Artificial Sequence
<220> FEATURE:
<223> OTHER INFORMATION: RBSc36

<400> SEQUENCE: 100
tcttcgccaa gctccttagc tcctaaagga ggtagtacat atgtgaagag                 50

<210> SEQ ID NO 101
<211> LENGTH: 49
<212> TYPE: DNA

```
<213> ORGANISM: Artificial Sequence
<220> FEATURE:
<223> OTHER INFORMATION: RBSc42

<400> SEQUENCE: 101
ttcgccaaca ggatacatct gtaaaggagg taacgatgat gtgaagagc              49

<210> SEQ ID NO 102
<211> LENGTH: 57
<212> TYPE: DNA
<213> ORGANISM: Artificial Sequence
<220> FEATURE:
<223> OTHER INFORMATION: T1 (L3S2P55)

<400> SEQUENCE: 102
ctcggtacca aagacgaaca ataagacgct gaaaagcgtc tttttcgtt ttggtcc       57

<210> SEQ ID NO 103
<211> LENGTH: 61
<212> TYPE: DNA
<213> ORGANISM: Artificial Sequence
<220> FEATURE:
<223> OTHER INFORMATION: T2 (L3S2P21)

<400> SEQUENCE: 103
ctcggtacca aattccagaa aagaggcctc ccgaaagggg ggcctttttt cgttttggtc   60
c                                                                  61

<210> SEQ ID NO 104
<211> LENGTH: 57
<212> TYPE: DNA
<213> ORGANISM: Artificial Sequence
<220> FEATURE:
<223> OTHER INFORMATION: T3 (ECK12033737)

<400> SEQUENCE: 104
ggaaacacag aaaaaagccc gcacctgaca gtgcgggctt ttttttcga ccaaagg       57

<210> SEQ ID NO 105
<211> LENGTH: 90
<212> TYPE: DNA
<213> ORGANISM: Artificial Sequence
<220> FEATURE:
<223> OTHER INFORMATION: T4 (ECK120029600)

<400> SEQUENCE: 105
ttcagccaaa aaacttaaga ccgccggtct tgtccactac cttgcagtaa tgcggtggac   60
aggatcggcg gttttctttt ctcttctcaa                                    90
```

METHOD OF SELECTING A POLYPEPTIDE OF INTEREST

CROSS-REFERENCE TO RELATED APPLICATIONS

This application is a National Phase of International Application No. PCT/GB2019/051727, filed Jun. 19, 2019, which designated the U.S. and that International Application was published under PCT Article 21(2) in English. This application also includes a claim of priority under 35 U.S.C. § 119(a) and § 365(b) to British patent application No. GB 1810052.9, filed Jun. 19, 2018, the contents of which are herein incorporated by reference in their entirety.

The present invention relates to polypeptides per se, and in particular, to the design and production of de novo (i.e. novel) polypeptides and of polypeptides which are variants (i.e. mutants) of existing polypeptides. The invention is particularly, although not exclusively, concerned with methods for identifying polypeptides of interest, be they novel or variant polypeptides, such as enzymes, and their encoding nucleotide sequences. The invention is especially concerned with improved methods of selecting or identifying proteins and polypeptides exhibiting desired properties. The invention is also concerned with novel enzymes per se, and their use in methods of production of compounds, such as isopropanol. The invention also extends to producing variant metabolic pathways, components thereof, such as enzymes, their encoding DNA sequences, and their regulatory elements, such as promoters and ribosome binding sites etc.

Enzymes are biocatalysts which present several advantages over non-biological catalysts, such as high specificity, stereoselectivity and catalysing reactions in mild conditions (e.g. temperature and pressure). These biocatalysts are of great interest for industry, as they can greatly reduce the cost of steps in the synthesis of many compounds and increase the yield and efficiency of the process (Johannes, Simurdiak & Zhao, 2006). However, for many catalytic steps, known enzymes catalyse the reaction poorly, or not at all, even though the type of reaction may be known to be catalysed by enzymes, so in principle, it is possible that a suitable enzyme could exist, or could be developed. Novel enzymes have even been developed for reactivities not previously known among reported enzymes.

With modern molecular biology methods including chemical synthesis of DNA, and with knowledge of the genetic triplet code, it is straightforward to obtain a novel DNA sequence that encodes a desired polypeptide sequence, comprising a series of amino acid residues. However, there are effectively infinite possible polypeptide sequences. It is not possible to determine which polypeptide sequence would result in an enzyme with specific desired catalytic properties by purely theoretical methods, so novel enzymes are developed experimentally. In nature, mutations which are beneficial for individuals to adapt to the environment are iteratively selected through natural selection. It is possible to mimic this process in the laboratory to try to evolve organisms or molecules so that they obtain enhanced properties or novel functions not found in nature, which can then be used to develop a wide range of applications of human interest (such as chemical biosynthesis, bioremediation, improving industrial processes by reducing the formation of products, etc.) (Turner, 2009; Johannes, Simurdiak & Zhao, 2006). This process, known as directed evolution, has become one of the most powerful tools for protein engineering, and it has proven to be particularly useful to improve specific features of enzymes, such as enhancing their kinetic properties, changing substrate specificity etc.

The first step to carry out directed evolution is the generation of a library of variants of the coding sequence of interest. As the rate of spontaneous mutations is usually insufficient to achieve the desired gene variant in a reasonable amount of time (for example, the mutation rate of wild type *Escherichia coli* is $1 \times 10^{-3}$ mutations per genome per generation (Lee et al, 2010)), different techniques to enhance genetic diversification through increasing the mutation rate have been developed. These include targeting modifications to particular positions in the DNA sequence, or increasing the mutation rate across the whole DNA sequence in an un-targeted way, or combinations of both. After generating a library of variants, high throughput screening and selection methods are employed to carry out a rapid exploration of the library to identify and isolate the enzymes of interest.

Although current molecular biology techniques allow the generation of vast libraries, the analysis of the libraries to detect the desired variants is often a laborious and time-consuming step. There are two main types of approaches to identify variants with the desired properties, screening and selection. Screening approaches consist of evaluating every enzyme variant separately for a certain property, such as enzymatic activity. In contrast, selection methods are based on applying an artificial selective pressure, i.e. conditions under which variants can be isolated on the basis of the desired property, typically by conferring a survival advantage on cells containing them. Crucially, this means that large numbers of variants can be evaluated together in mixtures, without the need to separate each beforehand, as is the case with screening mentioned above. For this reason, selection methods allow evaluation of variants at extremely high throughput, orders of magnitude greater than screening. However, selection methods usually work only for one specific enzyme activity, and cannot be broadly applied to different types of enzymes. Therefore, the main limitation to apply directed evolution in most cases is not the generation of the desired variants, but their identification.

There is therefore a need to provide improved selection methods for identifying polypeptides in general, and enzymes in particular, which exhibit desired properties.

Hence, according to a first aspect of the invention, there is provided a method of identifying a variant polypeptide of interest, or its encoding polynucleotide, the method comprising:

i) generating a plurality of variant polypeptides;

ii) expressing the plurality of variant polypeptides in an obligate or facultative anaerobe that is incapable of, or displays a reduction in, the oxidation of NADH and/or NADPH under anaerobic fermentation conditions;

iii) culturing, in growth media, the obligate or facultative anaerobe under anaerobic fermentation conditions in the presence of a substrate, wherein the polypeptide of interest enables the obligate or facultative anaerobe to oxidise, or to increase oxidation of, NADH and/or NADPH in the presence of the substrate;

iv) selecting an obligate or facultative anaerobe that grows or displays a growth advantage in the growth media; and v) identifying the variant polypeptide of interest expressed, or its encoding polynucleotide, in the obligate or facultative anaerobe of step (iv).

As described in the Examples, the novel selection methods of the invention are widely applicable in identifying polypeptides (preferably, enzymes), making use of enzymes that oxidise NADPH and/or NADH, and in particular to a broad class of enzymes, known as NAD(P)H-dependent oxidoreductases. For example, in one embodiment, the method comprises linking the growth of *Escherichia coli* with the functionality of the enzyme variants. In order to do this, the inventors generated an *Escherichia coli* strain in which lactate dehydrogenase (ldhA) and alcohol dehydrogenase (adhE) genes were knocked out (i.e. functionally deleted), making the strain unable to carry out anaerobic fermentation (sensu stricto, i.e. in the absence of an external electron acceptor) of glucose, because of its inability to regenerate NAD$^+$ (or NADP$^+$) to proceed with the oxidation of sugars in the growth media under anaerobic fermentative conditions. While the inventor's experiments involved anaerobic fermentation of glucose, the skilled person would understand that anaerobic fermentation may be performed using organic molecules other than glucose. This metabolic impairment can be complemented by introducing an exogenous reductase activity able to transfer electrons from NADH (or NADPH) to a specific electron acceptor. As the growth medium is supplemented with a substrate that is oxidised in relation to a more reduced product that is formed by reduction of the substrate, only cells transformed with a suitable oxidoreductase variant that can reduce the supplied substrate are able to grow under oxygen-limited or substantially oxygen-free conditions, i.e. anaerobic fermentation conditions (see FIG. 1). Thus, by transforming cells with a library of variants of an NAD(P)H-dependent oxidoreductase and supplementing the media with the oxidized version of the substrate towards which the desired variant should have activity, the variant enzyme will be selected and can then be easily identified and characterized.

Advantageously, the selection method of the invention is applicable to a broad class of polypeptides or enzymes, preferably NAD(P)H-dependent oxidoreductases, based on metabolic complementation with exogenous enzymes of bacterial cells with impaired anaerobic growth. The inventors demonstrate in the Examples how the selection method can be used to select a desired variant with altered cofactor specificity.

The inventors have validated the selection method of the invention by showing that anaerobic fermentative growth recovery is possible with several different combinations of enzymes and oxidized substrates, which may be exogenously added to the growth media, or may be endogenously produced by the anaerobe itself. Then, they have demonstrated the effectiveness of the method by using it to select a number of variant polypeptides, including the first ever reported variant of *Clostridium beijerinckii* alcohol dehydrogenase (CBADH) with reversed cofactor specificity, which employs NADH instead of NADPH, as well as a variant of *Myxococcus stipitatus* imine reductase, which employs NADH instead of NADPH, and variant of *Enterobacter cloacae* nitroreductases with altered substrate specificities. Finally, the inventors have integrated the newly generated CBADH variant into an isopropanol production pathway as an example of optimization of a metabolic process by tailoring the properties of the involved enzymes through directed evolution.

Preferably, step (i) of the method of the first aspect comprises the generation of a library (i.e. the plurality) of variants. The skilled person will appreciate that the variant polypeptide can refer to a polypeptide that has been in some way modified from a wild-type polypeptide. For example, the variant polypeptide may comprise at least one amino acid substitution, deletion or insertion compared to its wild-type counterpart. The plurality of variants in step (i) may be generated by targeting modifications to particular positions in the polypeptide's wild-type sequence, or by increasing the mutation rate across the whole wild-type sequence in an un-targeted way, or combinations of both. Variant polypeptide can also refer to a novel, synthetically designed, but non-naturally occurring polypeptide. The skilled person would understand "synthetically designed" to refer to a sequence that is not a variant of a wild-type polypeptide. The skilled person would understand that "synthetically designed" polypeptide can also include "hybrid polypeptides" comprising both synthetically designed and wild-type domains.

The skilled person would understand that, due to the degeneracy of the genetic code, alternative nucleotide sequences may encode the same protein. Accordingly, the methods described herein may be used to distinguish between these different polynucleotide sequences, as these alternative sequences may lead to differential expression of the variant polypeptide of interest as a result of codon usage, mRNA structure, addition, removal or modification of binding sites for protein or nucleic acid factors, or other functional features.

Thus, in one embodiment, the method may be used to select a variant polypeptide of interest comprising a polynucleotide sequence optimised for expression of the variant polypeptide of interest, wherein a variant polypeptide encoded by the optimised polynucleotide sequence, and expressed by an obligate or facultative anaerobe according to the invention, will result in an obligate or facultative anaerobe that grows or displays a growth advantage in the growth media in step (iv).

The plurality of variant polypeptides may be expressed according to step (ii) by a number of molecular biology techniques. For example, the variant polypeptides may be introduced into the obligate or facultative anaerobe by introducing into the obligate or facultative anaerobe one or more copies of a polynucleotide encoding the variant polypeptide. Preferably, the polynucleotide is introduced into the cell using a vector. The vector can be any molecule that may be used as a vehicle to transfer genetic material into a cell. Examples of vectors include plasmids, viral vectors, cosmids, and artificial chromosomes. Examples of molecular biology techniques used to transfer nucleotide sequences into a microorganism include, without limitation, transfection, electroporation, conjugation, transduction, and transformation. These methods are routine and known in the art. Insertion of a vector into a target cell is usually called transformation for bacterial cells, however, insertion of a viral vector is often called transduction. The terms transformation, transfection, and transduction, for the purpose of the present invention, are used interchangeably herein.

The obligate or facultative anaerobe may be a bacterium, archaeon, alga, yeast or fungus. The obligate or facultative anaerobe may be naturally-occurring, obtained through cultivation, obtained by genetic modification, or obtained by random mutagenesis. Random mutagenesis may be induced by a chemical mutagen or radiation. A suitable yeast may include *Saccharomyces* spp., preferably *S. cerevisiae*. A suitable fungus may include *Aspergillus* spp., preferably *A. fumigatus*. Preferably, however, the obligate or facultative anaerobe is a bacterium. A suitable bacterium may include *Geobacillus* spp., and most preferably, the bacterium is *Escherichia coli*.

The obligate or facultative anaerobe may be rendered incapable of, or display a reduction in, the oxidation of NADH and/or NADPH by having at least one gene, or product thereof, associated with a metabolic pathway involved in NAD$^+$ and/or NADP$^+$ generation which is non-functional and/or inhibited. Preferably, the at least one gene has been deleted, disrupted or mutated.

In one preferred embodiment, the at least one gene, or product thereof, encodes an enzyme that contributes to a fermentative pathway involved in the regeneration of $NAD^+$ and/or $NADP^+$.

In one preferred embodiment, the at least one gene, or product thereof, may encode an enzyme associated with lactic fermentation, ethanolic fermentation, butanol fermentation, isopropanol fermentation, 2,3-butanediol fermentation, butyraldehyde fermentation, 1,2-propanediol fermentation, 1,3-propanediol fermentation, propionic fermentation and/or acrylic fermentation. The skilled person would be aware of other suitable fermentation pathways.

In one preferred embodiment, the at least one gene, or product thereof, may encode pyruvate formate lyase, phosphate acetyltransferase, acetate kinase, malate dehydrogenase, fumarase, fumarate reductase, pyruvate decarboxylase, succinate dehydrogenase, succinyl-CoA synthetase, methyl-malonyl-CoA mutase, methylmalonyl-CoA epimerase, propionyl-CoA carboxylase, propionyl-CoA:Succinate CoA transferase, butanediol dehydrogenase, hydroxybutyrate dehydrogenase, acetyl-CoA acetyltransferase, enoyl-CoA hydratase, crotonyl-CoA reductase, acetolactate synthase, acetolactate decarboxylase, lactoyl-CoA dehydratase, acry-lyl-CoA reductase, aldehyde dehydrogenase (such as acet-aldehyde dehydrogenase, butyraldehyde dehydrogenase or propionaldehyde dehydrogenase), aldolase, 1,3-propanediol dehydrogenase, 1,2-propanediol dehydrogenase, lactalde-hyde dehydrogenase, ethanol dehydrogenase, primary alcohol dehydrogenase, bifunctional alcohol-aldehyde dehydrogenase and/or secondary alcohol dehydrogenase.

The skilled person would understand that the at least one gene, or product thereof, may encode an enzyme that does not directly produce oxidised NAD+ and/or NADP+, but is nonetheless an important component of pathways that produce oxidised NAD and/or NADP+.

In one embodiment, inactivation of malate dehydrogenase, fumarase, and/or fumarate reductase results in cells that are unable to perform respiration in the presence of oxygen. In another preferred embodiment, the at least one gene, or product thereof encodes lactate dehydrogenase and/or alcohol dehydrogenase. In another preferred embodiment, the at least one gene, or product thereof may encode lactate dehydrogenase and alcohol dehydrogenase. In another preferred embodiment, the at least one gene, or product thereof, may encode pyruvate formate lyase, phosphate acetyltransferase, acetate kinase, malate dehydrogenase, fumarase, fumarate reductase, pyruvate decarboxylase, succinate dehydrogenase, succinyl-CoA synthetase, methyl-malonyl-CoA mutase, methylmalonyl-CoA epimerase, propionyl-CoA carboxylase, propionyl-CoA:Succinate CoA transferase, butanediol dehydrogenase, hydroxybutyrate dehydrogenase, acetyl-CoA acetyltransferase, enoyl-CoA hydratase, crotonyl-CoA reductase, acetolactate synthase, acetolactate decarboxylase, lactoyl-CoA dehydratase, acry-lyl-CoA reductase, aldehyde dehydrogenase (such as acet-aldehyde dehydrogenase, butyraldehyde dehydrogenase or propionaldehyde dehydrogenase), aldolase, 1,3-propanediol dehydrogenase, 1,2-propanediol dehydrogenase, lactalde-hyde dehydrogenase, secondary alcohol dehydrogenase, alcohol dehydrogenase and/or lactate dehydrogenase. In an embodiment in which the obligate or facultative anaerobe is *Escherichia coli*, lactate dehydrogenase (i.e. *Escherichia coli* ldhA) and/or alcohol dehydrogenase (i.e. *Escherichia*

*coli* adhE), or a product thereof, associated with the NAD+ and/or NADP+ metabolic pathway, is non-functional and/or inhibited.

In another preferred embodiment, the at least one gene, or product thereof, may encode lactate dehydrogenase, alcohol dehydrogenase, soluble transhydrogenase and/or transmem-brane transhydrogenase. In an embodiment in which the obligate or facultative anaerobe is *Escherichia coli*, lactate dehydrogenase (i.e. *Escherichia coli* ldhA), alcohol dehy-drogenase (i.e. *Escherichia coli* adhE), soluble transhydro-genase (i.e. *Escherichia coli* sthA) and/or transmembrane transhydrogenase (i.e. *Escherichia coli* pntA and/or pntB) or a product thereof, associated with the NAD+ and/or NADP+ metabolic pathway, is non-functional and/or inhibited.

Preferably, when the at least one gene, or product thereof, encodes lactate dehydrogenase, alcohol dehydrogenase, soluble transhydrogenase and transmembrane transhydroge-nase, the variant polypeptide of interest enables the obligate or facultative anaerobe to oxidise, or to increase oxidation of NADH. Thus, in an embodiment in which the obligate or facultative anaerobe is *Escherichia coli*, lactate dehydroge-nase (i.e. *Escherichia coli* ldhA), alcohol dehydrogenase (i.e. *Escherichia coli* adhE), soluble transhydrogenase (i.e. *Escherichia coli* sthA) and transmembrane transhydroge-nase (i.e. *Escherichia coli* pntA and/or pntB), or a product thereof, associated with the NAD+ metabolic pathway, is non-functional and/or inhibited.

The substrate of step (iii) will vary depending on the variant polypeptide of interest. Preferably, the substrate is exogenously added into the growth media. Preferably, the substrate is endogenously produced by the anaerobe. The skilled person would understand that the term "endog-enously produced" may relate to a substrate that is naturally produced by the anaerobe or one that the anaerobe produces as a result of a genetic modification.

The skilled person would appreciate that a variant poly-peptide that is not a variant polypeptide of interest would not enable the obligate or facultative anaerobe to oxidise, or to increase oxidation of, NADH and/or NADPH in the pres-ence of the substrate.

In one embodiment, when the variant polypeptide of interest is a thermostable alcohol dehydrogenase from a *Thermus* sp., the substrate of step (iii) may be cyclo-hexanone. In another embodiment, when the variant poly-peptide of interest may be *Clostridium begjerinckii* alcohol dehydrogenase, the substrate of step (iii) is acetone.

In another embodiment, when the variant polypeptide of interest is *Enterobacter cloacae* nitroreductase, the substrate of step (iii) may be 4-nitrobenzoic acid, 2-nitrobenoic acid or 4-nitrobenzylic alcohol (also known as 4-nitrophenol). In another embodiment, when the variant polypeptide of inter-est is *Myxococcus stipitatus* imine reductase, the substrate of step (iii) may be 2-methylpyrroline.

Step (iii) of the method of the first aspect involves culturing the obligate or facultative anaerobe under anaero-bic fermentation conditions. Anaerobic fermentation condi-tions may include oxygen-limited or substantially oxygen-free conditions, as well as an absence of an external terminal electron acceptor suitable for performing anaerobic respira-tion, such as nitrate, fumarate or DMSO. Preferably, step (iii) of the method is performed under substantially oxygen-free conditions. The skilled person would understand that oxygen-free or substantially oxygen-free conditions can mean 0% (v/v) oxygen. Hence, the oxygen-free or substan-tially oxygen-free conditions in the absence of an external terminal electron acceptor suitable for performing anaerobic respiration equate to anaerobic fermentation conditions.

"Oxygen-limited conditions" can refer to oxygen concentrations of less than 21% (v/v), preferably less than 15% (v/v), more preferably less than 10% (v/v), even more preferably less than 5% (v/v), even more preferably less than 2% (v/v) and most preferably less than 1% (v/v).

"Oxygen-limited conditions" can refer to conditions in which oxygen situation is less than 90% saturation, less than 80% saturation, less than 70% saturation, less than 60% saturation. less than 50% saturation, less than 40% saturation, less than 30% saturation, less than 21% saturation, less than 15% saturation, less than 10% saturation, less than 5% saturation, less than 2% saturation or less than 1% saturation.

Thus, oxygen situation may be less than 21%, preferably less than 15%, more preferably less than 10%, even more preferably less than 5%, even more preferably less than 2% and most preferably less than 1%.

The skilled person would understand that the % saturation may prefer to a percentage of the maximum possible amount of oxygen that can dissolve in a solution at a given temperature.

Step (iii) may comprise culturing the obligate or facultative anaerobe under anaerobic fermentation conditions in the presence a growth substrate which the anaerobe requires for growth. In one preferred embodiment, the growth substrate may be glucose. In another embodiment, the growth substrate may be another organic molecule, such as sorbitol, gluconate, glucuronate, glycerol, fructose, lactose, citrate, rhamnose or fucose. The skilled person would be aware of organic molecules that are suitable for use as a growth substrate.

Preferably, an obligate or facultative anaerobe that does not express the variant polypeptide of interest will not grow, or grow at a reduced rate, for example increased doubling time, when compared to an obligate or facultative anaerobe expressing the variant polypeptide of interest, when culturing under the conditions of step (iii) to enable the selection step (iv). Preferably, the obligate or facultative anaerobe that expresses the variant polypeptide of interest grows or displays a growth advantage in the growth media, preferably compared to the corresponding wild-type or a variant polypeptide which is not the polypeptide of interest. For example, it may have a neutral effect or a deleterious mutation compared to the wild-type polypeptide. The doubling time of the obligate or facultative anaerobe that expresses the variant polypeptide of interest may be at least 1%, 2%, 5%, or 10% that of the doubling time of the corresponding wild-type or a variant polypeptide which is not the polypeptide of interest.

The skilled person would appreciate that the selection of step (iv) may relate to selection of cells or clones of the obligate or facultative anaerobe.

The variant polypeptide of interest, or its encoding polynucleotide, may be identified in step (v) by extraction of the protein and/or DNA from the obligate or facultative anaerobe and subsequent determination of the variant polypeptide sequence, or polynucleotide sequence encoding the variant polypeptide sequence, by analytical methods known to those skilled in the art.

Advantageously, the methods of the invention enable the identification or selection of variant polypeptides exhibiting altered properties compared to their wild-type counterparts. Advantageously, the methods of the invention also enable the identification or selection of synthetically produced and novel (variant) polypeptides exhibiting desired properties. Where the variant polypeptide is an enzyme, these properties may relate to altered specificity selected from a group consisting of: stereospecificity, thermostability, chemostability, pressure stability, substrate specificity, catalytic efficiency, oxidative stability, regiospecificity, cofactor preference/specificity and binding affinity for substrate and/or cofactor.

Preferably, the polypeptide of interest is an enzyme. Preferably, the enzyme is an enzyme that acts to oxidise NADH and/or NADPH, and more preferably the enzyme is an oxidoreductase, and even more preferably the enzyme is an NADH- and/or NADPH-dependent oxidoreductase. Most preferably, the enzyme is an NADH-dependent oxidoreductase. In one embodiment, the variant polypeptide of interest is an NADPH-dependent oxidoreductase with altered co-factor specificity, such that it oxidises NADH to NAD+ instead of, or in addition to, NADPH to NADP+.

In an embodiment of the invention, the variant polypeptide of interest that acts to oxidise NADH and/or NADPH is an L-amino acid dehydrogenase and the substrate is keto acid, wherein the L-amino acid dehydrogenase catalyses the reaction: 2-oxo acid+$NH_3$+NADH+H+ ⇌ L-amino acid+ H2O+NAD+. Thus, the present invention enables the identification of variant L-amino dehydrogenases that synthesize unnatural amino acids from the corresponding keto acid.

In an embodiment of the invention, the variant polypeptide of interest that acts to oxidise NADH and/or NADPH is an imine reductase and the substrate is imine or ketone and an amine. In particular, the variant polypeptide of interest is an imine reductase that is modified such that it oxidises NADH instead of NADPH.

In an embodiment of the invention, the variant polypeptide of interest that acts to oxidise NADH and/or NADPH is a carboxylic acid reductase and the substrate is carboxylic acid. In particular, the variant polypeptide of interest is a carboxylic acid reductase that is modified such that it oxidises NADH instead of NADPH.

In an embodiment of the invention, the variant polypeptide of interest that acts to oxidise NADH and/or NADPH is a nitroreductase, and the substrate is an organic nitro compound, preferably nitrobenzene or a derivative or analogue thereof.

In another embodiment of the invention, the substrate is an ester derivative of an oxidoreductase substrate, such that the ester derivative of an oxidoreductase substrate cannot be directly reduced by an oxidoreductase. In this embodiment, the variant polypeptide of interest is a lipase that acts to hydrolyse the ester derivative of an oxidoreductase substrate, such that the substrate can be subsequently reduced by an oxidoreductase. The oxidoreductase may be endogenously expressed in the obligate or facultative anaerobe. Accordingly, the obligate or facultative anaerobe may be transformed with a library of variants of the lipase. Alternatively, oxidoreductase may be exogenously expressed such that the obligate or facultative anaerobe is transformed with a library of variant lipases and an oxidoreductase— either a functional variant, or a library of variants.

In a preferred embodiment, the obligate or facultative anaerobe is *Escherichia coli* comprising mutation in, or deletion of, genes adhE and ldhA, the substrate is acetone and the polypeptide of interest is an NADPH-dependent oxidoreductase with altered co-factor specificity such that it oxidises NADH to NAD+, preferably the polypeptide of interest is *Clostridium begjerinckii* alcohol dehydrogenase (CBADH) with altered co-factor specificity such that it oxidises NADH to NAD+.

In one embodiment, the obligate or facultative anaerobe is *Escherichia coli* comprising mutation in adhE, ldhA and sthA, the substrate is acetone and the polypeptide of interest is an NADPH-dependent oxidoreductase with altered cofactor specificity such that it oxidises NADH to NAD+, preferably the polypeptide of interest is *Clostridium beijerinckii* alcohol dehydrogenase (CBADH) with altered cofactor specificity such that it oxidises NADH to NAD+.

In one embodiment, the obligate or facultative anaerobe is *Escherichia coli* comprising mutation in adhE, ldhA and pntA, the substrate is acetone and the polypeptide of interest is an NADPH-dependent oxidoreductase with altered cofactor specificity such that it oxidises NADH to NAD+, preferably the polypeptide of interest is *Clostridium beijerinckii* alcohol dehydrogenase (CBADH) with altered cofactor specificity such that it oxidises NADH to NAD+.

In one embodiment, the obligate or facultative anaerobe is *Escherichia coli* comprising mutation in adhE, ldhA and pntB, the substrate is acetone and the polypeptide of interest is an NADPH-dependent oxidoreductase with altered cofactor specificity such that it oxidises NADH to NAD+, preferably the polypeptide of interest is *Clostridium beijerinckii* alcohol dehydrogenase (CBADH) with altered cofactor specificity such that it oxidises NADH to NAD+.

In a preferred embodiment, the obligate or facultative anaerobe is *Escherichia coli* comprising mutation in, or deletion of, genes adhE, ldhA, sthA and pntA and/or pntB, the substrate is acetone and the polypeptide of interest is an NADPH-dependent oxidoreductase with altered co-factor specificity such that it oxidises NADH to NAD+, preferably the polypeptide of interest is *Clostridium begjerinckii* alcohol dehydrogenase (CBADH) with altered co-factor specificity such that it oxidises NADH to NAD+.

In another embodiment, the methods of the present invention may be used to identify variant polypeptides of interest that do not display NADH and/or NADPH dependent oxidoreductase activity but are coupled to a reaction of oxidation of NADH and/or NADPH. Accordingly, the exogenous substrate may be a precursor or intermediate of a substrate for a polypeptide that acts to oxidise NADH and/or NADPH. In one embodiment, when the substrate is a precursor or intermediate of a substrate for a polypeptide that acts to oxidise NADH and/or NADPH, the polypeptide of interest may act to convert the substrate into a substrate for a polypeptide that acts to oxidise NADH and/or NADPH, or act to convert the substrate to any intermediate along the metabolic pathway that results in the production of a substrate for a polypeptide that acts to oxidise NADH and/or NADPH.

In some embodiments, the polypeptide that acts to oxidise NADH and/or NADPH is promiscuous, such that it will oxidise NADH and/or NADPH in the presence of an intermediate substrate produced by the polypeptide of interest that is different to its natural substrate.

In another embodiment, the polypeptide of interest may act to transport an exogenous substrate from the culture media into the obligate or facultative anaerobe.

Accordingly, the polypeptide of interest may be a membrane transporter. The membrane transporter may be an active transporter, a passive transporter or a membrane channel. In this embodiment, the obligate or facultative anaerobe may be transformed with a library of variants of a membrane transporter among which one or more variants is capable of transporting an exogenous substrate from the culture media into the obligate or facultative anaerobe. The obligate or facultative anaerobe may also be transformed with an NADH and/or NADPH dependent oxidoreductase capable of reducing the substrate introduced by the membrane transporter, or a library of variants of it, some of which are expected to be able to reduce the substrate. Alternatively, the obligate or facultative anaerobe may endogenously express an NADH and/or NADPH-dependent oxidoreductase.

Preferably, the membrane transporter is capable of introducing a substrate into the obligate or facultative anaerobe such that, without the activity of the membrane transporter, the substrate can only enter the obligate or facultative anaerobe at a limited rate (either by passive diffusion through the membrane or channels or by the action of transporters natively present in cells).

In some embodiments, the polypeptide that acts to oxidise NADH and/or NADPH is promiscuous, such that it will oxidise NADH and/or NADPH in the presence of an external substrate transported into the cell by the polypeptide of interest that is different to its natural substrate.

Preferably, when the polypeptide of interest is a membrane transporter, the obligate or facultative anaerobe is impermeable to an exogenous substrate and has no membrane transporters present and/or no wild type polypeptide that acts to oxidise NADH and/or NADPH and/or comprises an NADH-dependent reductase from another organism.

The methods of the present invention can be used to develop and identify thermostable enzymes. Accordingly, in another embodiment, the obligate or facultative anaerobe of the invention is a thermophilic organism and the obligate or facultative anaerobe is cultured in step iii) of the first aspect at a temperature greater than 37° C., preferably at least 40° C., more preferably at least 50° C., even more preferably at least 60° C. and most preferably at least 70° C. and the variant polypeptide of interest, preferably an enzyme, is one which is able to provide for oxidation, or an increase in oxidation, of NADH and/or NADPH at such temperatures.

Preferably, the thermophilic organism is selected from the group consisting of: *Thermoanaerobacter ethanolicus, Caldicellulosiruptor lactoaceticus, Anoxybacillus kamchatkensis, Clostridium thermocellum, Geobacillus thermoglucosidasius*. Preferably, the thermophilic organism is *Geobacillus thermoglucosidasius*.

The methods of the present invention can be used to develop or identify a polypeptide associated with the expression or activity of any polypeptide described herein.

Accordingly, in another embodiment, the polypeptide is a factor required for the expression or correct folding of a polypeptide that enables the obligate or facultative anaerobe to oxidise, or to increase oxidation of, NADH and/or NADPH in the presence of the substrate. Preferably, the polypeptide is a chaperone, an enzyme involved in the synthesis of co-factors or prosthetic groups required for the proper formation or folding of the NADH/NADPH-dependent enzyme, or a transcription factor.

In another embodiment, the polypeptide is a factor required by a factor that is required for the expression or correct folding of a polypeptide that enables the obligate or facultative anaerobe to oxidise, or to increase oxidation of, NADH and/or NADPH in the presence of the substrate. Preferably, the polypeptide is a chaperone, an enzyme involved in the synthesis of co-factors or prosthetic groups required for the proper formation or folding of the factor that is required for the expression or correct folding of a polypeptide that enables the obligate or facultative anaerobe to oxidise, or to increase oxidation of, NADH and/or NADPH in the presence of the substrate.

In a second aspect of the invention there is provided a kit for identifying a variant polypeptide of interest, or its encoding polynucleotide, the kit comprising:

i) an obligate or facultative anaerobe that is rendered incapable of, or displays a reduction in, the oxidation of NADH and/or NADPH; and ii) growth media comprising a substrate;

wherein a variant polypeptide of interest will enable the obligate or facultative anaerobe to oxidise, or to increase oxidation of, NADH and/or NADPH in the presence of the substrate when grown under anaerobic fermentation conditions.

The kit may further comprise a plurality of variant polypeptides.

The obligate or facultative anaerobe may be rendered incapable of, or display a reduction in, the oxidation of NADH and/or NADPH by having at least one gene, or product thereof, associated with an NAD⁺ and/or NADP⁺ regeneration metabolic pathway, which is non-functional and/or inhibited. Preferably, at least one gene has been deleted, disrupted or mutated.

In one preferred embodiment, the genes may be lactate dehydrogenase, alcohol dehydrogenase, soluble transhydrogenase and/or transmembrane transhydrogenase genes. In an embodiment in which the obligate or facultative anaerobe is *Escherichia coli*, lactate dehydrogenase (i.e. *Escherichia coli* ldhA), alcohol dehydrogenase (i.e. *Escherichia coli* adhE), soluble transhydrogenase (i.e. *Escherichia coli* sthA) and/or transmembrane transhydrogenase (i.e. *Escherichia coli* pntA and/or pntB) or a product thereof, associated with an NAD+ and/or NADP+ regeneration metabolic pathway, is non-functional and/or inhibited.

The obligate or facultative anaerobe, variant polypeptide of interest or its encoding polynucleotide, substrate and anaerobic fermentation conditions are as defined in the first aspect.

In a preferred embodiment, the obligate or facultative anaerobe is *Escherichia coli* comprising mutation in, or deletion of, genes adhE and ldhA, the substrate is acetone and the polypeptide of interest is an NADPH-dependent oxidoreductase with altered co-factor specificity such that it oxidises NADH to NAD+.

In a preferred embodiment, the obligate or facultative anaerobe is *Escherichia coli* comprising mutation in, or deletion of, genes adhE, ldhA and sthA the substrate is acetone and the polypeptide of interest is an NADPH-dependent oxidoreductase with altered co-factor specificity such that it oxidises NADH to NAD+.

In a preferred embodiment, the obligate or facultative anaerobe is *Escherichia coli* comprising mutation in, or deletion of, genes adhE, ldhA and pntA, the substrate is acetone and the polypeptide of interest is an NADPH-dependent oxidoreductase with altered co-factor specificity such that it oxidises NADH to NAD+.

In a preferred embodiment, the obligate or facultative anaerobe is *Escherichia coli* comprising mutation in, or deletion of, genes adhE, ldhA and pntB, the substrate is acetone and the polypeptide of interest is an NADPH-dependent oxidoreductase with altered co-factor specificity such that it oxidises NADH to NAD+.

In a preferred embodiment, the obligate or facultative anaerobe is *Escherichia coli* comprising mutation in, or deletion of, genes adhE, ldhA, pntA and pntB, the substrate is acetone and the polypeptide of interest is an NADPH-dependent oxidoreductase with altered co-factor specificity such that it oxidises NADH to NAD+.

In another preferred embodiment, the obligate or facultative anaerobe is *Escherichia coli* comprising mutation in, or deletion of, genes adhE, ldhA, sthA and pntB, the substrate is acetone and the polypeptide of interest is an NADPH dependent oxidoreductase with altered co-factor specificity such that it oxidises NADH to NAD+.

In another preferred embodiment, the obligate or facultative anaerobe is *Escherichia coli* comprising mutation in, or deletion of, genes adhE, ldhA, sthA and pntA, the substrate is acetone and the polypeptide of interest is an NADPH dependent oxidoreductase with altered co-factor specificity such that it oxidises NADH to NAD+

In another preferred embodiment, the obligate or facultative anaerobe is *Escherichia coli* comprising mutation in, or deletion of, genes adhE, ldhA, sthA, pntA and pntB, the substrate is acetone and the polypeptide of interest is an NADPH dependent oxidoreductase with altered co-factor specificity such that it oxidises NADH to NAD+.

Advantageously, kits of the invention enable the identification or selection of variant polypeptides exhibiting altered properties compared to their wild-type counterparts.

Where the variant polypeptide is an enzyme, these properties may relate to altered specificity as defined in the first aspect.

In another embodiment, the kit of the present invention may be used to identify variant polypeptides of interest that do not display NADH and/or NADPH-dependent oxidoreductase activity but are coupled to an NADH and/or NADPH oxidation reaction.

Accordingly, the substrate may be a precursor or intermediate of a substrate for a polypeptide that acts to oxidise NADH and/or NADPH. In one embodiment, when the substrate is a precursor or intermediate of a substrate for a polypeptide that acts to oxidise NADH and/or NADPH, the polypeptide of interest may act to convert the substrate into a substrate for a polypeptide that acts to oxidise NADH and/or NADPH, or act to convert the substrate to any intermediate along the metabolic pathway that results in the production of a substrate for a polypeptide that acts to oxidise NADH and/or NADPH.

In another embodiment, the obligate or facultative anaerobe of the invention is a thermophilic organism and the variant polypeptide of interest, preferably an enzyme, is one which is able to provide for oxidation, or an increase in oxidation, of NADH and/or NADPH at temperatures of greater than 37° C., preferably at least 40° C., more preferably at least 50° C., even more preferably at least 60° C. and most preferably at least 70° C.

The present invention also relates to polypeptides of interest that have been identified using the method of the first aspect of the invention.

Accordingly, in a third aspect of the invention, there is provided a variant of *Clostridium begjerinckii* alcohol dehydrogenase, which comprises a modification of one or more amino acids relative to the wild-type sequence of SEQ ID NO: 1, wherein the variant has altered cofactor specificity compared to its corresponding wild-type, such that it utilises NADH instead of NADPH.

In one embodiment, the wild-type *Clostridium beijerinckii* alcohol dehydrogenase (CBADH) is provided by gene bank locus ID is AF157307.2. The skilled person would understand that the locus AF157307.2 (otherwise known as AF157307) encodes several genes, the 2$^{nd}$ being the CBADH gene. The protein sequence may be represented by the GeneBank ID AAA23199.2 and may comprise an amino acid sequence as set out in SEQ ID No:1, as follows:

-continued

[SEQ ID NO: 1]
MKGFAMLGINKLGWIEKERPVAGSYDAIVRPLAVSPCTSDIHTVFEGAL

GDRKNMILGHEAVGEVVEVGSEVKDFKPGDRVIVPCTTPDWRSLEVQAG

FQQHSNGMLAGWKFSNFKDGVFGEYFHVNDADMNLAILPKDMPLENAVM

ITDMMTTGFHGAELADIQMGSSVVVIGIGAVGLMGIAGAKLRGAGRIIG

VGSRPICVEAAKFYGATDILNYKNGHIVDQVMKLINGKGVDRVIMAGGG

SETLSQAVSMVKPGGIISNINYHGSGDALLIPRVEWGCGMAHKTIKGGL

CPGGGRLRAEMLRDMVVYNRVDLSKLVTHVYHGFDHIEEALLLMKDKPKD

LIKAVVIL

In one embodiment, the amino acid variant of CBADH comprises amino acid substitutions at positions 198, 199 and 218, optionally further comprising an amino acid substitution at position 200. Preferably, the substitution at position 198 is a substitution of Glycine with Aspartate, the substitution at position 199 is a substitution of Serine with Tyrosine and the substitution at position 218 is a substitution of Tyrosine to Proline. Preferably, the substitution at position 200 is a substitution of Arginine with Glycine.

Thus, in one embodiment, the amino acid variant of CBADH is provided herein as SEQ ID NO: 2, as follows:

[SEQ ID NO: 2]
MKGFAMLGINKLGWIEKERPVAGSYDAIVRPLAVSPCTSDIHTVFEGALG

DRKNMILGHEAVGEVVEVGSEVKDFKPGDRVIVPCTTPDWRSLEVQAGFQ

QHSNGMLAGWKFSNFKDGVFGEYFHVNDADMNLAILPKDMPLENAVMITD

MMTTGFHGAELADIQMGSSVVVIGIGAVGLMGIAGAKLRGAGRIIGVDYR

PICVEAAKFYGATDILNPKNGHIVDQVMKLINGKGVDRVIMAGGGSETLS

QAVSMVKPGGIISNINYHGSGDALLIPRVEWGCGMAHKTIKGGLCPGGRL

RAEMLRDMVVYNRVDLSKLVTHVYHGFDHIEEALLLMKDKPKDLIKAVVI

L

Accordingly, preferably the variant of CBADH comprises an amino acid sequence substantially as set out in SEQ ID NO: 2, or a fragment or variant thereof.

In one embodiment, the variant of CBADH may be encoded by a nucleotide sequence which is provided herein as SEQ ID NO: 3:

[SEQ ID NO: 3]
atgaaaggctttgccatgctgggtattaacaaattaggatggattgaaaa agaacgccccgtcgcgggttcctatgatgcgattgtacgaccettagccg tttcccgtgcactagcgatattcatacagtatttgaaggggctctcggc gatcgaaagaatatgattttaggccatgaagccgttggcgaagtcgttga agtgggctccgaagtgaaagatttcaaaccgggtgaccgtgtcatcgtgc cctgtactaccccagattggcgctctctggaggttcaagctggttttcaa caacatagtaatggtatgttggccggctggaagttttccaacttcaaaga tggagtatttggggagtattttcatgtgaacgatgcggatatgaatttgg ccatcctgccaaaagacatgcccttggagaatgctgtaatgatcaccgat atgatgaccaccggatttcatggggccgagttggccgatatccagatggg tagttctgtcgttgtgattggtatcggggcagttgggttaatgggaattg ctggggccaaattacgcggaGCAGGTCGGATTATTGGTGTCGACTATAGA

CCTATTTGCGTTGAGGCCGCCAAGTTCTACGGCGCGACCGACATTCTGAA

TCCGAAAAATGGCCATATTGTGGACcaggtaatgaagctaaccaatggga aaggcgtggaccgtgtgattatggctggaggtgggagtgaaacactgagc caagcagtgagcatggtgaaacctgggggaattatcagcaatatcaacta tcacggctctggtgacgctttgttaattccccgcgtggaatggggatgtg gcatggcgcacaagacgatcaaaggcggtttgtgtcccggaggccgttta cgggccgaaatgctacgggatatggtggtgtacaaccgtgtggatttgtc caagctggtgactcacgtttatcacggttttgaccatattgaagaagcct tgctactcatgaaagataaacctaaagatctcattaaggccgtagttatc ctctaa Hence, preferably the variant of CBADH may be encoded by a nucleic acid sequence as substantially set out in SEQ ID NO: 3, or a fragment or variant thereof.

In a fourth aspect of the invention, there is provided a variant of *Myxococcus stipitatus* imine reductase, which comprises a modification of one or more amino acids relative to the wild-type sequence of SEQ ID NO: 34, wherein the variant has altered cofactor specificity compared to its corresponding wild-type, such that it utilises NADH instead of NADPH.

In one embodiment, the wild-type imine reductase is a *Myxococcus stipitatus* imine reductase, and is preferably provided by gene bank locus ID. The protein sequence may be represented by the GeneBank ID WP_015347361 and may comprise an amino acid sequence as set out in SEQ ID No:34, as follows:

[SEQ ID No: 34]
MKPTLTVIGAGRMGSALIKAFLQSGYTTTVWNRTKAKSEPLAKLGAHLAD

TVRDAVKRSDIIVVNVLDYDTSDQLLRQDEVTRELRGKLLVQLTSGSPAL

AREQETWARQHGIDYLDGAIMATPDFIGQAECALLYSGSAALFEKHRAVL

NVLGGATSHVGEDVGHASALDSALLFQMWGTLFGTLQALAISRAEGIPLE

KTTAFIKLTEPVTQGAVADVLTRVQQNRLTADAQTLASLEAHNVAFQHLL

ALCEERNIHRGVADAMYSVIREAVKAGHGKDDFAILTRFLK

In one embodiment, the amino acid variant of *Myxococcus stipitatus* imine reductase comprises amino acid substitutions at positions 32, 33, 34 and/or 37, preferably at positions 32, 33, 34 and 37 of the wild type sequence.

Preferably, the substitution at position 32 is a substitution of Asparagine with Glutamic Acid, the substitution at position 33 is a substitution of Arginine with Valine, the substitution at position 34 is a substitution of Tyrosine with Arginine and the substitution at position 37 is a substitution of Lysine with Arginine.

Thus, in one embodiment, the amino acid variant of *Myxococcus stipitatus* imine reductase is provided herein as SEQ ID No: 35, as follows:

[SEQ ID No: 35]
MKPTLTVIGAGRMGSALIKAFLQSGYTTTVWEVRKARSEPLAKLGAHLAD

TVRDAVKRSDIIVVNVLDYDTSDQLLRQDEVTRELRGKLLVQLTSGSPAL

AREQETWARQHGIDYLDGAIMATPDFIGQAECALLYSGSAALFEKHRAVL

NVLGGATSHVGEDVGHASALDSALLFQMWGTLFGTLQALAISRAEGIPLE

KTTAFIKLTEPVTQGAVADVLTRVQQNRLTADAQTLASLEAHNVAFQHLL

ALCEERNIHRGVADAMYSVIREAVKAGHGKDDFAILTRFLK

Accordingly, preferably the variant of *Myxococcus stipi-tatus* imine reductase comprises an amino acid sequence substantially as set out in SEQ ID NO: 35, or a fragment or variant thereof.

In one embodiment, the variant of *Myxococcus stipitatus* imine reductase may be encoded by a nucleotide sequence which is provided herein as SEQ ID NO: 36:

[SEQ ID No: 36]
ATGAAACCGACCCTGACCGTTATTGGCGCTGGCCGTATGGGCTCCGCACT

GATTAAAGCATTCCTGCAATCTGGCTACACGACCACGGTGTGGGAGGTGC

GGAAAGCCCGGAGCGAACCGCTGGCAAAACTGGGCGCACATCTGGCTGAT

ACGGTGCGTGACGCCGTTAAACGCAGCGATATTATCGTGGTTAATGTGCT

GGATTATGACACCTCTGATCAGCTGCTGCGCCAAGACGAAGTGACGCGTG

AACTGCGCGGCAAACTGCTGGTTCAGCTGACCAGCGGTTCTCCGGCACTG

GCTCGTGAACAGGAAACGTGGGCGCGCCAACATGGCATTGATTATCTGGA

CGGTGCGATCATGGCCACCCCGGATTTTATTGGCCAGGCAGAATGCGCTC

TGCTGTACAGTGGTTCCGCGGCCCTGTTCGAAAAACACCGTGCTGTCCTG

AATGTGCTGGGCGGTGCCACCAGCCATGTCGGCGAAGATGTTGGTCATGC

CTCAGCACTGGACAGCGCCCTGCTGTTTCAGATGTGGGGCACCCTGTTCG

GTACGCTGCAAGCACTGGCTATTTCTCGCGCAGAAGGCATCCCGCTGGAA

AAAACCACGGCGTTTATCAAACTGACCGAACCGGTCACCCAGGGTGCCGT

TGCAGATGTCCTGACCCGTGTTCAGCAAAATCGCCTGACCGCAGACGCTC

AGACGCTGGCAAGTCTGGAAGCTCATAACGTGGCGTTCCAACACCTGCTG

GCCCTGTGTGAAGAACGTAATATCCATCGCGGTGTTGCGGATGCCATGTA

CTCCGTTATTCGTGAAGCGGTCAAAGCCGGCCACGGTAAAGATGACTTTG

CAATTCTGACCCGCTTCCTGAAATAA

Hence, preferably the variant of *Myxococcus stipitatus* imine reductase may be encoded by a nucleic acid sequence as substantially set out in SEQ ID NO: 36, or a fragment or variant thereof.

In a fifth aspect, there is provided a variant *Enterobacter cloacae* nitroreductase, which comprises a modification of one or more amino acids relative to the wild-type sequence of SEQ ID No: 37, wherein the variant has altered substrate specificity, such that it is able to catalyse the reduction of 2-nitrobenzoic acid (2-NBA) and/or 4-nitrobenzyl alcohol more efficiently than the wild type nitroreductase.

In one embodiment, the wild-type nitroreductase is *Enterobacter cloacae* nsfB nitroreductase, and is preferably provided by gene bank locus ID M63808.1. The protein sequence may be represented by the GeneBank ID AAA62801 and may comprise an amino acid sequence as set out in SEQ ID No: 37, as follows:

[SEQ ID No: 37]
MDIISVALKRHSTKAFDASKKLTAEEAEKIKTLLQYSPSSTNSQPWHFIV

ASTEEGKARVAKSAAGTYVFNERKMLDASHVVVFCAKTAMDDAWLERVVD

QEEADGRENTPEAKAANHKGRTYFADMHRVDLKDDDQWMAKQVYLNVGNF

LLGVGAMGLDAVPIEGFDAAILDEEFGLKEKGFTSLVVVPVGHHSVEDFN

ATLPKSRLPLSTIVTEC

In one embodiment, the amino acid variant of *Entero-bacter cloacae* nitroreductase comprises amino acid substi-tutions at positions 40, 41, 68 and/or 124, preferably at positions 41, 68 and 124 or positions 40, 41 and 124.

Preferably, the substitution at position 40 is a substitution of Serine with Alanine, the substitution at position 41 is a substitution of Threonine with Isoleucine or Leucine, the substitution at position 68 is a substitution of Tyrosine with Leucine and the substitution at position 124 is a substitution of Phenylalanine with Alanine or Leucine.

In one embodiment, the variant has altered substrate specificity, such that it is able to catalyse the reduction of 2-nitrobenzoic acid (2-NBA) more efficiently than the wild type nitroreductase and the variant comprises a substitution at position 40, which is a substitution of Serine with Alanine, a substitution at position 41, which is a substitution of Threonine with Isoleucine and a substitution at position 124, which is a substitution of Phenylalanine with Alanine.

Thus, in one embodiment, the amino acid variant of *Enterobacter cloacae* nitroreductase is provided herein as SEQ ID NO: 38, as follows:

[SEQ ID No: 38]
MDIISVALKRHSTKAFDASKKLTAEEAEKIKTLLQYSPSAINSQPWHFIV

ASTEEGKARVAKSAAGTYVFNERKMLDASHVVVFCAKTAMDDAWLERVVD

QEEADGRFNTPEAKAANHKGRTYAADMHRVDLKDDDQWMAKQVYLNVGNF

LLGVGAMGLDAVPIEGFDAAILDEEFGLKEKGFTSLVVVPVGHHSVEDFN

ATLPKSRLPLSTIVTEC

Accordingly, preferably the variant of *Enterobacter cloa-cae* nitroreductase comprises an amino acid sequence sub-stantially as set out in SEQ ID NO: 38, or a fragment or variant thereof.

In one embodiment, the variant of *Enterobacter cloacae* nitroreductase may be encoded by a nucleotide sequence which is provided herein as SEQ ID NO: 39:

[SEQ ID No: 39]
ATGGATATCATTTCTGTCGCCCTGAAACGCCACTCTACCAAGGCGTTCGA

CGCAAGCAAAAAACTGACCGCGGAAGAAGCGGAAAAAATCAAAACCCTGC

TGCAGTACAGCCCGTCCGCAATAAACTCCCAGCCGTGGCACTTCATTGTA

GCCAGCACCGAGGAAGGAAAAGCGCGCGTGGCGAAGTCCGCTGCGGGCAC

CTATGTGTTCAACGAACGCAAAATGCTGGATGCTTCCCACGTGGTGGTGT

TCTGCGCGAAAACCGCGATGGATGACGCCTGGCTGGAGCGCGTCGTGGAT

CAGGAAGAGGCCGATGGCCGTTTCAACACGCCGGAAGCCAAAGCCGCAAA

CCATAAGGGCCGCACCTACGCAGCCGACATGCACCGCGTGGATCTGAAAG

ATGACGACCAGTGGATGGCGAAGCAGGTTTACCTGAACGTCGGCAACTTC

-continued

```
CTGCTGGGCGTGGGCGCGATGGGTCTGGACGCGGTACCAATTGAAGGTTT

CGACGCCGCTATTCTCGACGAAGAGTTTGGCCTGAAAGAGAAAGGCTTCA

CCAGCCTGGTGGTGGTACCGGTTGGGCACCACAGCGTGGAAGATTTCAAC

GCCACGCTGCCGAAATCTCGCCTGCCGCTGAGCACGATTGTGACCGAGTG

CTAA
```

Hence, preferably the variant of *Enterobacter cloacae* nitroreductase may be encoded by a nucleic acid sequence as substantially set out in SEQ ID NO: 39, or a fragment or variant thereof.

In one embodiment, the variant has altered substrate specificity, such that it is able to catalyse the reduction of 4-nitrobenzyl alcohol more efficiently than the wild type nitroreductase and the variant comprises a substitution at position 41, which is a substitution of Threonine with Leucine, a substitution at position 68, which is a substitution of Tyrosine with Leucine and a substitution at position 124, which is a substitution of Phenylalanine with Leucine.

Thus, in one embodiment, the amino acid variant of *Enterobacter cloacae* nitroreductase is provided herein as SEQ ID NO: 40, as follows:

```
                                        [SEQ ID No: 40]
MDIISVALKRHSTKAFDASKKLTAEEAEKIKTLLQYSPSSLNSQPWHFIV

ASTEEGKARVAKSAAGTLVFNERKMLDASHVVVFCAKTAMDDAWLERVVD

QEEADGRFNTPEAKAANHKGRTYLADMHRVDLKDDDQWMAKQVYLNVGNF

LLGVGAMGLDAVPIEGFDAAILDEEFGLKEKGFTSLVVVPVGHHSVEDFN

ATLPKSRLPLSTIVTEC
```

Accordingly, preferably the variant of nitroreductase comprises an amino acid sequence substantially as set out in SEQ ID NO: 40, or a fragment or variant thereof.

In one embodiment, the variant of *Enterobacter cloacae* nitroreductase may be encoded by a nucleotide sequence which is provided herein as SEQ ID NO: 41:

```
                                        [SEQ ID No: 41]
ATGGATATCATTTCTGTCGCCCTGAAACGCCACTCTACCAAGGCGTTCGA

CGCAAGCAAAAAACTGACCGCGGAAGAAGCGGAAAAAATCAAAACCCTGC

TGCAGTACAGCCCGTCCTCACTAAACTCCCAGCCGTGGCACTTCATTGTA

GCCAGCACCGAGGAAGGAAAAGCGCGCGTGGCGAAGTCCGCTGCGGGCAC

CCTTGTGTTCAACGAACGCAAAATGCTGGATGCTTCCCACGTGGTGGTGT

TCTGCGCGAAAACCGCGATGGATGACGCCTGGCTGGAGCGCGTCGTGGAT

CAGGAAGAGGCCGATGGCCGTTTCAACACGCCGGAAGCCAAAGCCGCAAA

CCATAAGGGCCGCACCTACCTCGCCGACATGCACCGCGTGGATCTGAAAG

ATGACGACCAGTGGATGGCGAAGCAGGTTTACCTGAACGTCGGCAACTTC

CTGCTGGGCGTGGGCGCGATGGGTCTGGACGCGGTACCAATTGAAGGTTT

CGACGCCGCTATTCTCGACGAAGAGTTTGGCCTGAAAGAGAAAGGCTTCA

CCAGCCTGGTGGTGGTACCGGTTGGGCACCACAGCGTGGAAGATTTCAAC

GCCACGCTGCCGAAATCTCGCCTGCCGCTGAGCACGATTGTGACCGAGTG

CTAA
```

Hence, preferably the variant of *Enterobacter cloacae* nitroreductase may be encoded by a nucleic acid sequence as substantially set out in SEQ ID NO: 41, or a fragment or variant thereof.

The skilled person would understand that catalysing the reduction of 2-nitrobenzoic acid (2-NBA) and/or 4-nitrobenzyl alcohol more efficiently than the wild-type nitroreductase may refer to improved kinetic parameters.

Improved kinetic parameters may relate to a lower Km that the wild-type nitroreductase. Preferably, Km values are at least 1.5, 2, 3, 5 or 10 times lower than the Km of the wild-type enzyme. Most preferably, Km values are at least 10 times lower than the Km of the wild-type enzyme.

Preferably, the Km value is less than 9 mM, 8 mM 7 mM 6 mM 5 mM, 4 mM, 3 mM, 2 mM or 1 mM. Preferably, the Km value is less than 9 mM. Preferably, the Km value is less than 1 mM, 0.1 mM or 0.01 mm. The skilled person would understand that mM refers to milliMolar.

Improved kinetic parameters may relate to a higher Kcat that the wild-type nitroreductase. Preferably, kcat values are at least 1.5, 2, 3, 5 or 10 times larger than the kcat of the wild-type enzyme. Most preferably, Kcat values are at least 10 times larger than the Kcat of the wild-type enzyme.

In a sixth aspect, there is provided a nucleic acid comprising a nucleotide sequence encoding the variant of CBADH of the third aspect, the variant of imine reductase of the fourth aspect or the variant of nitroreductase of the fifth aspect.

The nucleic acid may preferably be an isolated or purified nucleic acid sequence. The nucleic acid sequence may preferably be a DNA sequence.

The nucleic acid molecule may be contained within a suitable vector to form a recombinant vector.

Hence, in a seventh aspect of the invention, there is provided a vector comprising the nucleic acid sequence according to the sixth aspect.

The vector may for example be a plasmid, cosmid or phage and/or be a viral vector. Such recombinant vectors are highly useful in the delivery systems of the invention for transforming cells with the nucleic acid molecule. The nucleic acid sequence may preferably be a DNA sequence.

Preferably, the vector of the seventh aspect is recombinant. Recombinant vectors may also include other functional elements. For example, they may further comprise a variety of other functional elements including a suitable promoter for initiating transgene expression upon introduction of the vector in a host cell. For instance, the vector is preferably capable of autonomously replicating in the nucleus of the host cell. In this case, elements which induce or regulate DNA replication may be required in the recombinant vector. Alternatively, the recombinant vector may be designed such that it integrates into the genome of a host cell. In this case, DNA sequences which favour targeted integration (e.g. by homologous recombination) are envisaged. Suitable promoters may include the SV40 promoter, CMV, EF1a, PGK, viral long terminal repeats, as well as inducible promoters, such as the Tetracycline inducible system, as examples. The cassette or vector may also comprise a terminator, such as the Beta globin, SV40 polyadenylation sequences or synthetic polyadenylation sequences. The recombinant vector may also comprise a promoter or regulator or enhancer to control expression of the nucleic acid as required. Tissue specific promoter/enhancer elements may be used to regulate expression of the nucleic acid in specific cell types. The promoter may be constitutive, inducible or regulated.

The vector may also comprise DNA coding for a gene that may be used as a selectable marker in the cloning process, i.e. to enable selection of cells that have been transfected or transformed, and to enable the selection of cells harbouring vectors incorporating heterologous DNA. For example, ampicillin, neomycin, puromycin or chloramphenicol resistance is envisaged. Alternatively, the selectable marker gene may be in a different vector to be used simultaneously with the vector containing the transgene. Antibiotic marker free selection systems may also be used, for example a poison/antidote system or auxotrophic system.

The cassette or vector may also comprise DNA involved with regulating expression of the transgene.

Purified vector may be inserted directly into a host cell by suitable means, e.g. direct endocytic uptake. The vector may be introduced directly into cells of a host subject (e.g. a eukaryotic or prokaryotic cell) by transfection, infection, electroporation, microinjection, cell fusion, protoplast fusion or ballistic bombardment. Alternatively, vectors of the invention may be introduced directly into a host cell using a particle gun.

The nucleic acid molecule may (but not necessarily) be one, which becomes incorporated in the DNA of cells. Undifferentiated cells may be stably transformed leading to the production of genetically modified daughter cells (in which case regulation of expression in the subject may be required e.g. with specific transcription factors or gene activators). Alternatively, the delivery system may be designed to favour unstable or transient transformation of differentiated cells. When this is the case, regulation of expression may be less important because expression of the DNA molecule will stop when the transformed cells die or stop expressing the protein.

Alternatively, the delivery system may provide the nucleic acid molecule to host cell without it being incorporated in a vector. For instance, the nucleic acid molecule may be incorporated within a liposome or virus particle. Alternatively a "naked" nucleic acid molecule may be inserted into a subject's cells by a suitable means e.g. direct endocytic uptake.

The nucleic acid molecule may be transferred to host cells by transfection, infection, microinjection, cell fusion, protoplast fusion or ballistic bombardment. For example, transfer may be by ballistic transfection with coated gold particles, liposomes containing the nucleic acid molecule, viral vectors (e.g. adenovirus) and means of providing direct nucleic acid uptake (e.g. endocytosis) by application of the nucleic acid molecule directly.

Advantageously, the enzyme of the third aspect of the invention may replace the wild type enzyme in an isopropanol metabolic pathway to improve yield.

Accordingly, in an eighth aspect of the invention there is provided a method of producing isopropanol, comprising:
  i) providing a microorganism expressing acetyl-CoA acetyltransferase, acetoacetate decarboxylase, acetyl-CoA:acetoacetyl-CoA transferase and a variant of CBADH according to the third aspect;
  ii) culturing the microorganism of step i) in culture media comprising acetone; and
  iii) obtaining isopropanol from the culture.

Preferably, the microorganism may be a bacterium, archaeon, alga, yeast or fungus. A suitable yeast may include *Saccharomyces* spp., preferably *S. cerevisiae*. A suitable fungus may include *Aspergillus* spp., preferably *A. fumigatus*. Preferably, however, the microorganism is a bacterium. A suitable bacterium may include *Geobacillus* spp., Most preferably, the bacterium is *Escherichia coli*. Preferably, the microorganism is an obligate or facultative anaerobe. Preferably, the obligate or facultative anaerobe is *Escherichia coli*.

Preferably, the acetyl-CoA acetyltransferase is *Escherichia coli* acetyl-CoA acetyltransferase (atoB). Preferably, the acetyl-CoA:acetoacetyl-CoAtransferase is *Escherichia coli* acetyl-CoA:acetoacetyl-CoA transferase (atoAD). Alternatively, the acetyl-CoA acetyltransferase is acetyl-CoA acetyltransferase from *Clostridium acetobutylicum* (thlA) and the acetyl-CoA:acetoacetyl-CoA transferase is acetyl-CoA:acetoacetyl-CoA transferase from *Clostridium acetobutylicum* (ctfAB). Preferably, the acetoacetate decarboxylase is *Clostridium acetobutylicum* acetoacetate decarboxylase (adc).

The skilled person would understand that acetyl-CoA acetyltransferase transferase may be referred to by the EC number 2.3.1.9, and may be referred to as thioloase, or synthetic thiolase.

The skilled person would understand that acetyl-CoA: acetoacetyl-CoA transferase may be referred to by the EC number 2.8.3.8, and may be referred to as acetoacetate: acetyl-CoA CoA-transferase, acyl-CoA:acetate CoA-transferase or acetoacetyl-CoA transferase, amongst other names.

The skilled person would understand that atoAD refers to two genes, atoA and atoD, which encode different subunits of acetyl-CoA:acetoacetyl-CoAtransferase.

Preferably, step (ii) of the method is performed under anaerobic fermentation conditions. Preferably, anaerobic fermentation conditions are as defined in the first aspect. Preferably, step (ii) of the method is performed under substantially oxygen-free conditions.

In a ninth aspect of the invention, there is provided a microorganism that expresses acetyl-CoA acetyltransferase, acetoacetate decarboxylase, acetyl-CoA:acetoacetyl-CoA transferase and a variant of CBADH according to the third aspect, wherein the microorganism is capable of producing isopropanol when cultured in culture media comprising acetone.

Preferably, the microorganism is as described in the eighth aspect.

Preferably, the microorganism is an obligate or facultative anaerobe that is capable of producing isopropanol when cultured under anaerobic fermentation conditions, preferably substantially oxygen-free conditions, in culture media comprising acetone.

Preferably, the obligate or facultative anaerobe is *Escherichia coli*. Preferably, the acetyl-CoA acetyltransferase is *Escherichia coli* acetyl-CoA acetyltransferase (atoB). Preferably, the acetoacetate decarboxylase is *Clostridium acetobutylicum* acetoacetate decarboxylase (adc). Preferably, the acetyl-CoA:acetoacetyl-CoAtransferase is *Escherichia coli* acetyl-CoA:acetoacetyl-CoAtransferase (atoAD).

In a tenth aspect of the invention there is provided a method of producing 2-methylpyrrolidine, comprising:
  i) providing a microorganism expressing a variant of imine reductase according to the fourth aspect;
  ii) culturing the microorganism of step i) in culture media comprising 2-methylpyrroline; and
  iii) obtaining 2-methylpyrrolidine from the culture.

Preferably, the microorganism may be a bacterium, archaeon, alga, yeast or fungus. A suitable yeast may include *Saccharomyces* spp., preferably *S. cerevisiae*. A suitable fungus may include *Aspergillus* spp., preferably *A. fumigatus*. Preferably, however, the microorganism is a bacterium. A suitable bacterium may include *Geobacillus* spp., Most preferably, the bacterium is *Escherichia coli*. Preferably, the microorganism is an obligate or facultative anaerobe. Preferably, the obligate or facultative anaerobe is *Escherichia coli*.

Preferably, step (ii) of the method is performed under anaerobic fermentation conditions. Preferably, anaerobic fermentation conditions are as defined in the first aspect. Preferably, step (ii) of the method is performed under substantially oxygen-free conditions.

In an eleventh aspect of the invention, there is provided a microorganism that expresses a variant of imine reductase according to the fourth aspect.

Preferably, the microorganism is as defined in the tenth aspect.

Preferably, the microorganism is an obligate or facultative anaerobe that is capable of producing 2-methylpyrrolidine when cultured under anaerobic fermentation conditions, preferably substantially oxygen-free conditions, in culture media comprising 2-methylpyrroline.

Preferably, the obligate or facultative anaerobe is *Escherichia coli*. Preferably, the enzyme is *Myxococcus stipitatus* imine.

In a tenth aspect of the invention there is provided a method of producing 2-hydroxylaminoebenzoic acid and/or 2-aminobenzoic acid, comprising:

i) providing a microorganism expressing a variant of nitroreductase according to the fifth aspect;

ii) culturing the microorganism of step i) in culture media comprising 2-nitrobenzoic acid; and iii) obtaining 2-hydroxylaminoebenzoic acid and/or 2-aminobenzoic acid from the culture.

Preferably, the microorganism may be a bacterium, archaeon, alga, yeast or fungus. A suitable yeast may include *Saccharomyces* spp., preferably *S. cerevisiae*. A suitable fungus may include *Aspergillus* spp., preferably *A. fumigatus*. Preferably, however, the microorganism is a bacterium. A suitable bacterium may include *Geobacillus* spp., Most preferably, the bacterium is *Escherichia coli*. Preferably, the microorganism is an obligate or facultative anaerobe. Preferably, the obligate or facultative anaerobe is *Escherichia coli*.

Preferably, step (ii) of the method is performed under anaerobic fermentation conditions. Preferably, anaerobic fermentation conditions are as defined in the first aspect. Preferably, step (ii) of the method is performed under substantially oxygen-free conditions.

In an eleventh aspect of the invention, there is provided a microorganism that expresses a variant of nitroreductase according to the fifth aspect.

Preferably, the microorganism is as defined in the tenth aspect.

Preferably, the microorganism is an obligate or facultative anaerobe that is capable of producing 2-hydroxylaminoebenzoic acid or 2-aminobenzoic acid when cultured under anaerobic fermentation conditions, preferably substantially oxygen-free conditions, in culture media comprising 2-nitrobenzoic acid.

Preferably, the obligate or facultative anaerobe is *Escherichia coli*. Preferably, the enzyme is *Enterobacter cloacae* nfsB nitroreductase.

In a twelfth aspect of the invention there is provided a method of producing 4-hydroxylaminobenzylic alcohol or 4-aminobenzylic alcohol, comprising:

i) providing a microorganism expressing a variant of nitroreductase according to the fifth aspect;

ii) culturing the microorganism of step i) in culture media comprising 4-nitrobenzylic alcohol; and iii) obtaining 4-hydroxylaminobenzylic alcohol or 4-aminobenzylic alcohol from the culture.

Preferably, the microorganism may be a bacterium, archaeon, alga, yeast or fungus. A suitable yeast may include *Saccharomyces* spp., preferably *S. cerevisiae*. A suitable fungus may include *Aspergillus* spp., preferably *A. fumigatus*. Preferably, however, the microorganism is a bacterium. A suitable bacterium may include *Geobacillus* spp., Most preferably, the bacterium is *Escherichia coli*. Preferably, the microorganism is an obligate or facultative anaerobe. Preferably, the obligate or facultative anaerobe is *Escherichia coli*.

Preferably, step (ii) of the method is performed under anaerobic fermentation conditions. Preferably, anaerobic fermentation conditions are as defined in the first aspect. Preferably, step (ii) of the method is performed under substantially oxygen-free conditions.

In a thirteenth aspect of the invention, there is provided a microorganism that expresses a variant of nitroreductase according to the fifth aspect.

Preferably, the microorganism is as defined in the tenth twelfth.

Preferably, the microorganism is an obligate or facultative anaerobe that is capable of producing 4-hydroxylaminobenzylic alcohol or 4-aminobenzylic alcohol when cultured under anaerobic fermentation conditions, preferably substantially oxygen-free conditions, in culture media comprising 4-nitrobenzylic alcohol.

Preferably, the obligate or facultative anaerobe is *Escherichia coli*. Preferably, the enzyme is *Enterobacter cloacae* nfsB nitroreductase.

The inventor's selection methods may also be used to select for optimised nucleic acid sequences regulating the expression of and/or encoding metabolic pathway components of interest. The method advantageously ensures that selection pressure eliminates defective variants without a completely functional pathway.

Accordingly, in the fourteenth aspect of the invention, there is provided a method of generating a variant metabolic pathway of interest, the method comprising:

i) generating a plurality of: (a) variant components of a metabolic pathway, (b) variant polynucleotide sequences encoding the variant components, and/or (c) variant polynucleotide sequences which regulate the expression of genes encoding the components;

ii) culturing, in growth media, an obligate or facultative anaerobe comprising the variant of step (i), wherein, in the presence of the variant, the anaerobe is able to oxidise, or to increase oxidation of, NADH and/or NADPH in the presence of the substrate, and wherein, in the absence of the variant, the anaerobe is incapable of, or displays a reduction in, the oxidation of NADH and/or NADPH under anaerobic fermentation conditions in the presence of a substrate;

iii) selecting an obligate or facultative anaerobe that grows or displays a growth advantage in the growth media; and iv) identifying the variant metabolic pathway of interest, in the obligate or facultative anaerobe of step (iii).

The obligate or facultative anaerobe, anaerobic fermentation conditions, substrate and growth media may be as defined in the first aspect.

The variant components of a metabolic pathway may be polypeptides. Preferably the variant components of a metabolic pathway are enzymes.

Preferably, the polynucleotide sequences encoding the variant components are DNA molecules. Preferably, the polynucleotide sequences encoding the variant components encode metabolic pathway enzymes.

The skilled person would understand that the variant polynucleotide sequences which regulate the expression of genes encoding the components may be non-protein coding sequences that regulate the expression of one or more of the variant components of a metabolic pathway.

The variant polynucleotide of step (c) may be a regulatory element selected from the group consisting of: enhancers, operators, promoters, transcription factor binding sites/recognition sequences, transcriptional terminators, antiterminators, riboregulators, ribozymes, insulators, synthetic elements such as RiboJ, ribosome binding sites, different variants of coding sequences which may functionally differ for example with different codon usage, 5' untranslated regions, 5' untranslated regions, ribonuclease recognition sequences, binding sites/recognition sequences for RNA-binding proteins, binding sites/recognition sequences for histones or other DNA/chromosome remodelling factors.

The variation may relate to variants of a polypeptide or polynucleotide that has been in some way modified from a wild-type polypeptide or polynucleotide. For example, the variant polypeptide may comprise at least one amino acid or nucleotide substitution, deletion or insertion compared to its wild-type counterpart. However, the skilled person would also appreciate that variant in relation to the metabolic pathway of interest may relate to the replacement of a wild-type polypeptide and/or polynucleotide with a different, naturally occurring polypeptide and/or polynucleotide.

Preferably, the variant polynucleotide of step (c) may be a promoter and/or ribosomal binding site, as is exemplified in figure.

Preferably, step i) comprises generating a plurality of variant polynucleotide sequences which regulate the expression of genes encoding the components.

Preferably, step i) comprise generating variant polynucleotide sequences encoding the variant components and variant polynucleotide sequences which regulate the expression of genes encoding the components, such that the combination of variant polynucleotide sequences constitutes a complete variant metabolic pathway of interest.

The variant metabolic pathway of interest may relate to a metabolic pathway that has altered substrate specificity and/or produces a different compound to that of the wild-type pathway. The different compound may be a naturally occurring compound or a non-naturally occurring compound.

The variant metabolic pathway of interest may display an increase in the production of the compound produced by the metabolic pathway, when compared to wild-type pathway.

Thus, the method may further comprise: step v) detecting a compound that is produced by the variant metabolic pathway of interest, and optionally comparing the concentration of the compound that is produced by the variant metabolic pathway of interest with that of the concentration of the compound that is produced by the wild-type metabolic pathway of interest.

The metabolic pathway of interest may be an isopropanol metabolic pathway. The isopropanol metabolic pathway may be as defined in the third aspect.

Preferably, the isopropanol metabolic pathway comprises the enzymes *Clostridium acetobutylicum* acetyl-CoA acetyl-transferase (thl) and acetoacetate decarboxylase (adc), *Escherichia coli* acetoacetyl-CoA transferase (atoAD) and wildtype CBADH. Preferably, the pathway is as defined in the third aspect.

Preferably, the variant metabolic pathway of interest is a variant isopropanol metabolic pathway. Preferably, the variant isopropanol metabolic pathway comprises at least one variant polynucleotide sequences which regulate the expression of genes encoding the components, preferably a plurality of variant polynucleotide sequences which regulate the expression of genes encoding the components.

The invention also extends to variant metabolic pathways that have been identified by methods of the fourteenth aspect.

Thus, in a fifteenth aspect there is provided a variant metabolic pathway of interest that has been obtained by, or is obtainable from, the method of the fourteenth aspect.

In a sixteenth aspect there is provided a polynucleotide sequence that encodes variant isopropanol metabolic pathway components, comprising a polynucleotide sequence as substantially set out in SEQ ID Nos: 88 or 89, or a fragment or variant thereof.

Preferably, the isopropanol pathway is as defined in the fourteenth aspect.

Thus, the polynucleotide may be SEQ ID No: 88, as follows:

[SEQ ID No: 88]
```
TTGACAGCTAGCTCAGTCCTAGGGACTATGCTAGCCCACTACGTTTTTTA

GAAAAAGGAGGTATGCGAGatgaaaaattgtgtcatcgtcagtgcggtac gtactgctatcggtagttttaacggttcactcgcttccaccagcgccatc gacctgggggcgacagtaattaaagccgccattgaacgtgcaaaaatcga ttcacaacacgttgatgaagtgattatgggtaacgtgttacaagccgggc tggggcaaaatccggcgcgtcaggcactgttaaaaagcgggctggcagaa acggtgtgcggattcacggtcaataaagtatgtggttcgggtcttaaaag tgtggcgcttgccgcccaggccattcaggcaggtcaggcgcagagcattg tggcggggggtatggaaaatatgagtttagccccctacttactcgatgca aaagcacgctctggttatcgtcttggagacggacaggtttatgacgtaat cctgcgcgatggcctgatgtgcgccacccatggttatcatatggggatta ccgccgaaaacgtggctaaagagtacggaattacccgtgaaatgcaggat gaactggcgctacattcacagcgtaaagcggcagccgcaattgagtccgg tgcttttacagccgaaatcgtcccggtaaatgttgtcactcgaaagaaaa ccttcgtgttcagtcaagacgaattcccgaaagcgaattcaacggctgaa gcgttaggtgcattgcgcccggccttcgataaagcaggaacagtcaccgc tgggaacgcgtctggtattaacgacggtgctgccgctctggtgattatgg aagaatctgcggcgctggcagcaggccttacccccctggctcgcattaaa agttatgccagcggtggcgtgcccccccgcattgatgggtatggggccagt acctgccacgcaaaaagcgttacaactggcggggctgcaactggcggata ttgatctcattgaggctaatgaagcatttgctgcacagttccttgccgtt gggaaaaacctgggctttgattctgagaaagtgaatgtcaacggcggggc catcgcgctcgggcatcctatcggtgccagtggtgctcgtattctggtca cactattacatgccatgcaggcacgcgataaaacgctggggctggcaaca ctgtgcattggcggcggtcagggaattgcgatggtgattgaacggttgaa ttaaCTCGGTACCAAAGACGAACAATAAGACGCTGAAAAGCGTCTTTTTT
```

-continued

```
CGTTTTGGTCCGGAAATGCAGCTGATGGCTAGCTCAGTCCTAGGGATTAT

GCTAGCCCACTACGTTTTTTAGAAAAAGGAGGTATGCGAGATGaaaacaa aattgatgacattacaagacgCCACCGGCTTCTTTCGTGACGGCATGACC

ATCATGGTGGGCGGATTTATGGGGATTGGCACTCCATCCCGCCTGGTTGA

AGCATTACTGGAATCTGGTGTTCGCGACCTGACATTGATAGCCAATGATA

CCGCGTTTGTTGATACCGGCATCGGTCCGCTCATCGTCAATGGTCGAGTC

CGCAAAGTGATTGCTTCACATATCGGCACCAACCCGGAAACAGGTCGGCG

CATGATATCTGGTGAGATGGACGTCGTTCGGTGCCGCAAGGTACGCTAA

TCGAGCAAATTCGCTGTGGTGGAGCTGGACTTGGTGGTTTTCTCACCCCA

ACGGGTGTCGGCACCGTCGTAGAGGAAGGCAAACAGACACTGACACTCGA

CGGTAAAACCTGGCTGCTCGAACGCCCACTGCGCGCCGACCTGGCGCTAA

TTCGCGCTCATCGTTGCGCACACACTTGGCAACCTGACCTATCAACTTAGC

GCCCGCAACTTTAACCCCCTGATAGCCCTTGCGGCTGATATCACGCTGGT

AGAGCCAGATGAACTGGTCGAAACCGGCGAGCTGCAACCTGACCATATTG

TCACCCCTGGTGCCGTTATCGACCACATCATCGTTTCACAGGAGAGCAAA taaCTCGGTACCAAATTCCAGAAAAGAGGCCTCCCGAAAGGGGGGCCTTT

TTTCGTTTTGGTCCGGAAGGTCAGTTGACAGCTAGCTCAGTCCTAGGGAC

TATGCTAGCCCAAGCTCCTTAGCTCCTAAAGGAGGTAGTACATATGGATG

CGAAACAACGTATTGCGCGCCGTGTGGCGCAAGAGCTTCGTGATGGTGAC

ATCGTTAACTTAGGGATCGGTTTACCCACAATGGTCGCCAATTATTTACC

GGAGGGTATTCATATCACTCTGCAATCGGAAAACGGCTTCCTCGGTTTAG

GCCCGGTCACGACAGCGCATCCAGATCTGGTGAACGCTGGCGGGCAACCG

TGCGGTGTTTTACCCGGTGCAGCCATGTTTGATAGCGCCATGTCATTTGC

GCTAATCCGTGGCGGTCATATTGATGCCTGCGTGCTCGGCGGTTTGCAAG

TAGACGAAGAAGCAAACCTCGCGAACTGGGTAGTGCCTGGGAAAATGGTG

CCCGGTATGGGTGGCGCGATGGATCTGGTGACCGGGTCGCGCAAAGTGAT

CATCGCCATGGAACATTGCGCCAAAGATGGTTCAGCAAAAATTTTGCGCC

GCTGCACCATGCCACTCACTGCGCAACATGCGGTGCATATGCTGGTTACT

GAACTGGCTGTCTTTCGTTTTATTGACGGCAAAATGTGGCTCACCGAAAT

TGCCGACGGGTGTGATTTAGCCACCGTGCGTGCCAAAACAGAAGCTCGGT

TTGAAGTCGCCGCCGATCTGgaatacgcaacggggtgatttaGGAAACACA

GAAAAAAGCCCGCACCTGACAGTGCGGGCTTTTTTTTTCGACCAAAGGGG

AGCTTCAGTTGACGGCTAGCTCAGTCCTAGGTACAGTGCTAGCCCACATG

ATCGAATGATTAAAGGAGGTTGGAGGTATGttaaaggatgaagtaattaa acaaattagcacgccattaacttcgcctgcatttcctagaggaccctata aatttcataatcgtgagtattttaacattgtatatcgtacagatatggat gcacttcgtaaagttgtgccagagcctttagaaattgatgagcccttagt caggtttgaaattatggcaatgcatgatacgagtggacttggttgttata cagaaagcggacaggctattcccgtaagctttaatggagttaagggagat tatcttcatatgatgtatttagataatgagcctgcaattgcagtaggaag
```

-continued

```
ggaattaagtgcatatcctaaaaagctcgggtatccaaagcttttgtgg attcagatactttagtaggaactttagactatggaaaacttagagttgcg acagctacaatggggtacaaacataaagccttagatgctaatgaagcaaa ggatcaaatttgtcgccctaattatatgttgaaaataatacccaattatg atggaagccctagaatatgtgagcttataaatgcgaaaatcacagatgtt accgtacatgaagcttggacaggaccaactcgactgcagttatttgatca cgctatggcgccacttaatgatttgccagtaaaagagattgtttctagct ctcacattcttgcagatataatattgcctagagctgaagttatatatgat tatcttaagtaaTTCAGCCAAAAAACTTAAGACCGCCGGTCTTGTCCACT

ACCTTGCAGTAATGCGGTGGACAGGATCGGCGGTTTTCTTTTCTCTTCTC

AAGGACGCTCAGCTGATGGCTAGCTCAGTCCTAGGGATTATGCTAGCCCA

ACAGGATACATCTGTAAAGGAGGTAACGATGATGaaaggctttgccatgc tgggtattaacaaattaggatggattgaaaaagaacgccccgtcgcgggt tcctatgatgcgattgtacgacccttagccgtttccccgtgcactagcga tattcatacagtatttgaagggggctctcggcgatcgaaagaatatgattt taggccatgaagccgttggcgaagtcgttgaagtgggctccgaagtgaaa gatttcaaaccgggtgaccgtgtcatcgtgccctgtactaccccagattg gcgctctctggaggttcaagctggttttcaacaacatagtaatggtatgt tggccggctggaagttttccaacttcaaagatggagtatttggggagtat tttcatgtgaacgatgcggatatgaatttggccatcctgccaaaagacat gcccttggagaatgctgtaatgatcaccgatatgatgaccaccggatttc atggggccgagttggccgatatccagatgggtagttctgtcgttgtgatt ggtatcggggcagttgggttaatgggaattgctggggccaaattacgcgg agcaggtcggattattggtgtcggcagtcggcctatttgcgttgaggccg ccaagttctacggcgcgaccgacattctgaattacaaaaatggccatatt gtggaccaggtaatgaagctaaccaatgggaaaggcgtggaccgtgtgat tatggctggaggtgggagtgaaacactgagccaagcagtgagcatggtga aacctgggggaattatcagcaatatcaactatcacggctctggtgacgct ttgttaattccccgcgtggaatggggatgtggcatggcgcacaagacgat caaaggcggtttgtgtcccggaggccgtttacgggccgaaatgctacggg atatggtggtgtacaaccgtgtggatttgtccaagctggtgactcacgtt tatcacggttttgaccatattgaagaagccttgctactcatgaaagataa acctaaagatctcattaaggccgtagttatcctctaaCTCGGTACCAAAG

ACGAACAATAAGACGCTGAAAAGCGTCTTTTTTTCGTTTTGGTCC
```

Hence, preferably the polynucleotide may be a nucleic acid sequence as substantially set out in SEQ ID NO: 88, or a fragment or variant thereof.

Thus, the polynucleotide may be SEQ ID No: 89, as follows:

[SEQ ID No: 89]

TTGACAGCTAGCTCAGTCCTAGGGACTATGCTAGCCCAAAAACACTAGACTGGAAAGGAGGTAGAGAATatgaaaaat tgtgtcatcgtcagtgcggtacgtactgctatcggtagttttaacggttcactcgcttccaccagcgccatcgacctg ggggcgacagtaattaaagccgccattgaacgtgcaaaaatcgattcacaacacgttgatgaagtgattatgggtaac gtgttacaagccgggctggggcaaaatccggcgcgtcaggcactgttaaaaagcgggctggcagaaacggtgtgcgga ttcacggtcaataaagtatgtggttcgggtcttaaaagtgtggcgcttgccgcccaggccattcaggcaggtcaggcg cagagcattgtggcggggggtatggaaaatatgagtttagccccctacttactcgatgcaaaagcacgctctcggttat cgtcttggagacggacaggtttatgacgtaatcctgcgcgatggcctgatgtgcgccacccatggttatcatatgggg attaccgccgaaaacgtggctaaagagtacggaattacccgtgaaatgcaggatgaactggcgctacattcacagcgt aaagcggcagccgcaattgagtccggtgcttttacagccgaaatcgtcccggtaaatgttgtcactcgaaagaaaacc ttcgtgttcagtcaagacgaattcccgaaagcgaattcaacggctgaagcgttaggtgcattgcgcccggccttcgat aaagcaggaacagtcaccgctgggaacgcgtctggtattaacgacggtgctgccgctctggtgattatggaagaatct gcggcgctggcagcaggccttacccccctggctcgcattaaaaagttatgccagcggtggcgtgccccccgcattgatg ggtatggggccagtacctgccacgcaaaaagcgttacaactggcggggctgcaactggcggatattgatctcattgag gctaatgaagcatttgctgcacagttccttgccgttgggaaaaacctgggctttgattctgagaaagtgaatgtcaac ggcggggccatcgcgctcgggcatcctatcggtgccagtggtgctcgtattctggtcacactattacatgccatgcag gcacgcgataaaacgctggggctggcaacactgtgcattggcggcggtcagggaattgcgatggtgattgaacggttg aattaaCTCGGTACCAAAGACGAACAATAAGACGCTGAAAAGCGTCTTTTTTCGTTTTGGTCCGGAAATGCAGCTGAT GGCTAGCTCAGTCCTAGGGATTATGCTAGCCCAACAGGATACATCTGTAAAGGAGGTAACGATGATGaaaacaaaatt gatgacattacaagacgCCACCGGCTTCTTTCGTGACGGCATGACCATCATGGTGGGCGGATTTATGGGGATTGGCAC

TCCATCCCGCCTGGTTGAAGCATTACTGGAATCTGGTGTTCGCGACCTGACATTGATAGCCAATGATACCGCGTTTGT

TGATACCGGCATCGGTCCGCTCATCGTCAATGGTCGAGTCCGCAAAGTGATTGCTTCACATATCGGCACCAACCCGGA

AACAGGTCGGCGCATGATATCTGGTGAGATGGACGTCGTTCTGGTGCCGCAAGGTACGCTAATCGAGCAAATTCGCTG

TGGTGGAGCTGGACTTGGTGGTTTTCTCACCCCAACGGGTGTCGGCACCGTCGTAGAGGAAGGCAAACAGACACTGAC

ACTCGACGGTAAAACCTGGCTGCTCGAACGCCCACTGCGCGCCGACCTGGCGCTAATTCGCGCTCATCGTTGCGACAC

ACTTGGCAACCTGACCTATCAACTTAGCGCCCGCAACTTTAACCCCCTGATAGCCCTTGCGGCTGATATCACGCTGGT

AGAGCCAGATGAACTGGTCGAAACCGGCGAGCTGCAACCTGACCATATTGTCACCCCTGGTGCCGTTATCGACCACAT

CATCGTTTCACAGGAGAGCAAAtaaCTCGGTACCAAATTCCAGAAAAGAGGCCTCCCGAAAGGGGGGCCTTTTTTCGT

TTTGGTCCGGAAGGTCAGTTGACAGCTAGCTCAGTCCTAGGTACTGTGCTAGCCCAAGCTCCTTAGCTCCTAAAGGAG

GTAGTACATATGGATGCGAAACAACGTATTGCGCGCCGTGTGGCGCAAGAGCTTCGTGATGGTGACATCGTTAACTTA

GGGATCGGTTTACCCACAATGGTCGCCAATTATTTACCGGAGGGTATTCATATCACTCTGCAATCGGAAAACGGCTTC

CTCGGTTTAGGCCCGGTCACGACAGCGCATCCAGATCTGGTGAACGCTGGCGGGCAACCGTGCGGTGTTTTACCCGGT

GCAGCCATGTTTGATAGCGCCATGTCATTTGCGCTAATCCGTGGCGGTCATATTGATGCCTGCGTGCTCGGCGGTTTG

CAAGTAGACGAAGAAGCAAACCTCGCGAACTGGGTAGTGCCTGGGAAAATGGTGCCCGGTATGGGTGGCGCGATGGAT

CTGGTGACCGGGTCGCGCAAAGTGATCATCGCCATGGAACATTGCGCCAAAGATGGTTCAGCAAAAATTTTGCGCCGC

TGCACCATGCCACTCACTGCGCAACATGCGGTGCATATGCTGGTTACTGAACTGGCTGTGTCTTTCGTTTTATTGACGGC

AAAATGTGGCTCACCGAAATTGCCGACGGGTGTGATTTAGCCACCGTGCGTGCCAAAACAGAAGCTCGGTTTGAAGTC

GCCGCCGATCTGaatacgcaacggggtgatttataaGGAAACACAGAAAAAAGCCCGCACCTGACAGTGCGGGCTTTT

TTTTTCGACCAAAGGGGAGCTTCAGTTGACAGCTAGCTCAGTCCTAGGTACTGTGCTAGCCCAACAGGATACATCTGT

AAAGGAGGTAACGATGATGttaaaggatgaagtaattaaacaaattagcacgccattaacttcgcctgcatttcctag aggaccctataaatttcataatcgtgagtattttaacattgtatatcgtacagatatggatgcacttcgtaaagttgt -continued

```
gccagagcctttagaaattgatgagcccttagtcaggtttgaaattatggcaatgcatgatacgagtggacttggttg ttatacagaaagcggacaggctattcccgtaagctttaatggagttaagggagattatcttcatatgatgtatttaga taatgagcctgcaattgcagtaggaagggaattaagtgcatatcctaaaaagctcgggtatccaaagctttttgtgga ttcagatactttagtaggaactttagactatggaaaacttagagttgcgacagctacaatggggtacaaacataaagc cttagatgctaatgaagcaaaggatcaaatttgtcgccctaattatatgttgaaaataatacccaattatgatggaag ccctagaatatgtgagcttataaatgcgaaaatcacagatgttaccgtacatgaagcttggacaggaccaactcgact gcagttatttgatcacgctatggcgccacttaatgatttgccagtaaaagagattgtttctagctctcacattcttgc agatataatattgcctagagctgaagttatatatgattatcttaagTTCAGCCAAAAAACTTAAGACCGCCGGTCTTG

TCCACTACCTTGCAGTAATGCGGTGGACAGGATCGGCGGTTTTCTTTTCTCTTCTCAAGGACGCTCAGCTGATGGCTA

GCTCAGTCCTAGGGATTATGCTAGCCCACATGATCGAATGATTAAAGGAGGTTGGAGGTATGaaaggctttgccatgc tgggtattaacaaattaggatggattgaaaaagaacgccccgtcgcgggttcctatgatgcgattgtacgacccttag ccgtttccccgtgcactagcgatattcatacagtatttgaaggggctctcggcgatcgaaagaatatgattttaggcc atgaagccgttggcgaagtcgttgaagtgggctccgaagtgaaagatttcaaaccgggtgaccgtgtcatcgtgccct gtactaccccagattggcgctctctggaggttcaagctggtttcaacaacatagtaatggtatgttggccggctgga agttttccaacttcaaagatggagtatttggggagtattttcatgtgaacgatgcggatatgaatttggccatcctgc caaaagacatgcccttggagaatgctgtaatgatcaccgatatgatgaccaccggatttcatggggccgagttggccg atatccagatgggtagttctgtcgttgtgattggtatcggggcagttgggttaatgggaattgctggggccaaattac gcggagcaggtcggattattggtgtcggcagtcggcctatttgcgttgaggccgccaagttctacggcgcgaccgaca ttctgaattacaaaaatggccatattgtggaccaggtaatgaagctaaccaatgggaaaggcgtggaccgtgtgatta tggctggaggtgggagtgaaacactgagccaagcagtgagcatggtgaaacctgggggaattatcagcaatatcaact atcacggctctggtgacgctttgttaattccccgcgtggaatggggatgtggcatggcgcacaagacgatcaaaggcg gtttgtgtcccggaggccgtttacgggccgaaatgctacgggatatggtggtgtacaaccgtgtggatttgtccaagc tggtgactcacgtttatcacggtttttgaccatattgaagaagccttgctactcatgaaagataaacctaaagatctca ttaaggccgtagttatcctcTAACTCGGTACCAAAGACGAACAATAAGACGCTGAAAAGCGTCTTTTTTCGTTTTGGT cc
```

Hence, preferably polynucleotide may be a nucleic acid sequence as substantially set out in SEQ ID NO: 89, or a fragment or variant thereof.

In a seventeenth aspect of the invention, there is provided a microorganism that comprises a) a variant metabolic pathway of interest that has been obtained, or is obtainable from, the method of the fourteenth aspect, or b) a polynucleotide sequence that encodes variant isopropanol metabolic pathway components of the sixteenth aspect.

Preferably, the microorganism may be a bacterium, archaeon, alga, yeast or fungus. A suitable yeast may include *Saccharomyces* spp., preferably *S. cerevisiae*. A suitable fungus may include *Aspergillus* spp., preferably *A. fumigatus*. Preferably, however, the microorganism is a bacterium. A suitable bacterium may include *Geobacillus* spp., Most preferably, the bacterium is *Escherichia coli*. Preferably, the microorganism is an obligate or facultative anaerobe. Preferably, the obligate or facultative anaerobe is *Escherichia coli*.

Preferably, the microorganism is an obligate or facultative anaerobe that is capable of producing isopropanol when cultured under anaerobic fermentation conditions, preferably substantially oxygen-free conditions. in culture media comprising acetone.

Preferably, the microorganism comprises acetyl-CoA acetyltransferase, acetoacetate decarboxylase, acetyl-CoA:acetoacetyl-CoA transferase and CBADH, preferably as defined in the third aspect.

It will be appreciated that the invention extends to any nucleic acid or peptide or variant, derivative or analogue thereof, which comprises substantially the amino acid or nucleic acid sequences of any of the sequences referred to herein, including variants or fragments thereof. The terms "substantially the amino acid/nucleotide/peptide sequence", "variant" and "fragment", can be a sequence that has at least 40% sequence identity with the amino acid/nucleotide/peptide sequences of any one of the sequences referred to herein, for example 40% identity with the sequence identified as SEQ ID Nos: 1 to 105.

Amino acid/polynucleotide/polypeptide sequences with a sequence identity which is greater than 65%, more preferably greater than 70%, even more preferably greater than 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet, etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (v) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: END-GAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps and either including or excluding overhangs. Preferably, overhangs are included in the calculation. Hence, a most preferred method for calculating percentage identity between two sequences comprises (i) preparing a sequence alignment using the ClustalW program using a suitable set of parameters, for example, as set out above; and (ii) inserting the values of N and T into the following formula:—Sequence Identity=(N/T)*100.

Alternative methods for identifying similar sequences will be known to those skilled in the art. For example, a substantially similar nucleotide sequence will be encoded by a sequence which hybridizes to DNA sequences or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C.

Alternatively, a substantially similar polypeptide may differ by at least 1, but less than 5, 10, 20, 50 or 100 amino acids from the sequences shown in, for example, SEQ ID Nos: 1 to 105.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

FIG. 1 is a schematic representation of one embodiment of the selection system of the invention. The selection system is based on a bacterial strain with impaired anaerobic fermentation. Such a strain was generated by knocking out the adhE and ldhA genes, critical for the alcoholic and lactic fermentation pathways. The strain is unable to grow under anaerobic fermentation conditions due to its inability to regenerate oxidized $NAD^+$. If cells of this strain are cultured anaerobically in a medium supplemented with a specific oxidized substrates and transformed with a library of a NAD(H)-dependent oxidoreductases or NADP(H) dependent oxidoreductases, only the cells carrying a variant oxidoreductase which is able to oxidize the supplemented substrate will be able to grow;

FIG. 2 shows anaerobic fermentative growth recovery with adhE. FIG. 2a: Growth curve of BW25113, LS1 and LS1+pLS1 cultures. LS1 cells are unable to grow in anaerobic fermentative conditions. Transformation with pLS1 (which carries the adhE gene) allows growth recovery. FIG. 2b: HPLC-RID of fermentation broth of BW25113, LS1 and LS1+pLS1 cultures. LS1 cells transformed with pLS1 show a profile of fermentation products similar to that of BW25113, except for the absence of lactate;

FIG. 3 shows metabolic complementation with TADH. FIG. 3a: LS1 cells transformed with either pLS1 or pLS12 (carrying TADH) are unable to grow under anaerobic conditions if cyclohexanone is not added to the medium. If cyclohexanone is added to the medium, LS1 cells transformed with pLS12 (but not with pLS1) achieve growth recovery through anaerobic fermentation. FIG. 3b: Quantification by means of GC of cyclohexanone and cyclohexanol in fermentation broth of LS1+pUC19, LS1+pLS1 and LS1+ pLS12 anaerobic cultures supplemented with cyclohexanone. When cells are transformed with pLS12, cyclohexanone is completely consumed, and cyclohexanol is generated. FIG. 3c: TADH is able reduce cyclohexanone, 3-methylcyclohexanone and butanal with NADH, and oxidize ethanol with NAD$^+$;

FIG. 4 shows selection of an NAD(H)-dependent variant of CBADH. FIG. 4a: LS1 cells cultured anaerobically with acetone added to the medium and transformed with the library of variants of CBADH were able to grow faster than those transformed with pLS6. FIG. 4b: When LS1 cells were transformed with the isolated variant, anaerobic growth recovery was even more efficient than when they were transformed with the library. FIG. 4c: Characterization of the fermentation broth by means of HPLC-RID (left) and GC (right) revealed that in cells transformed with the NAD(H)-dependent variant glucose consumption did not result into ethanol or lactate production as expected. Acetone was consumed and transformed into isopropanol. FIG. 4d: Enzymatic activity assays revealed the new variant had no activity with NADP(H), but had gained activity with NAD(H);

Figure 8:
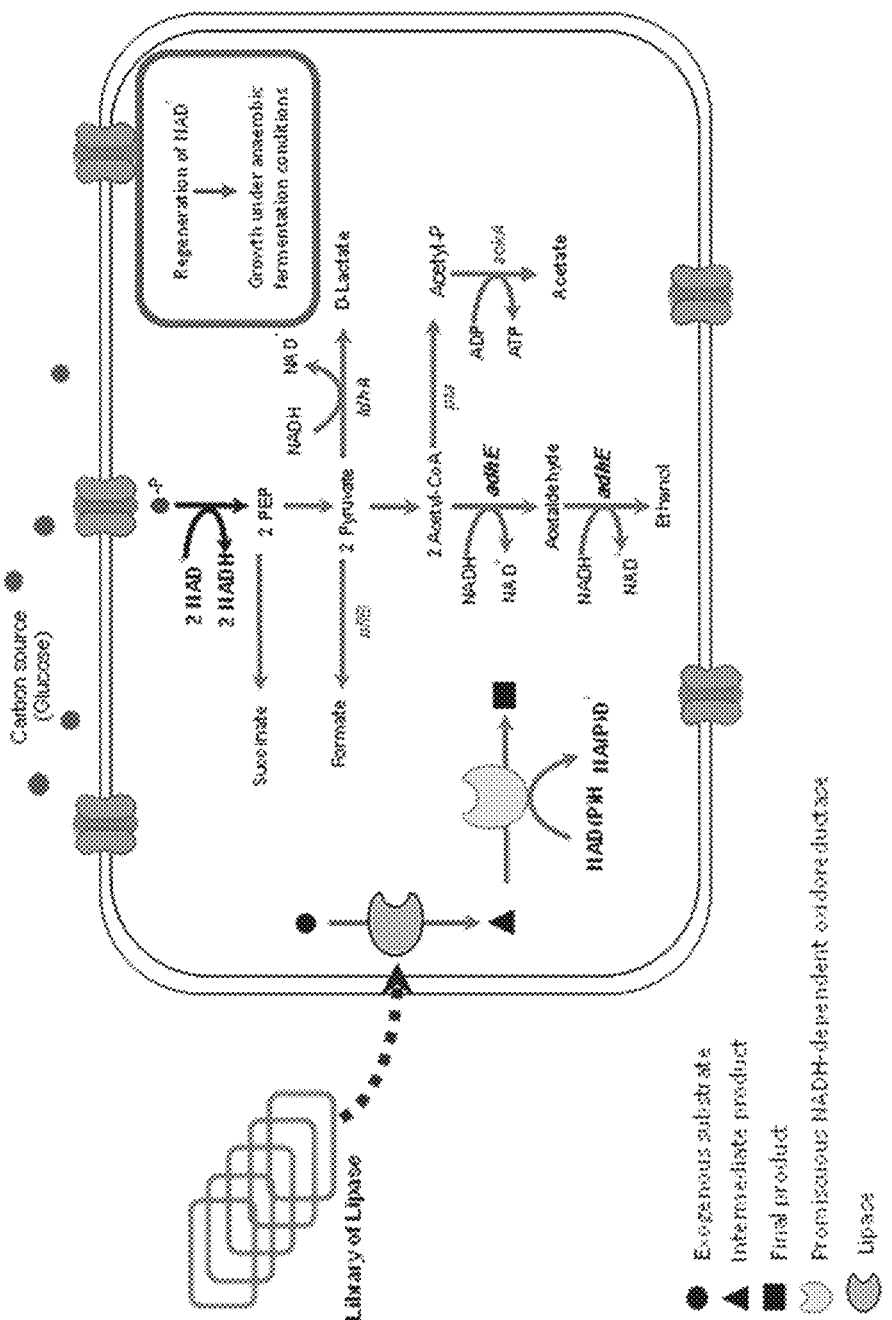
Figure 9:
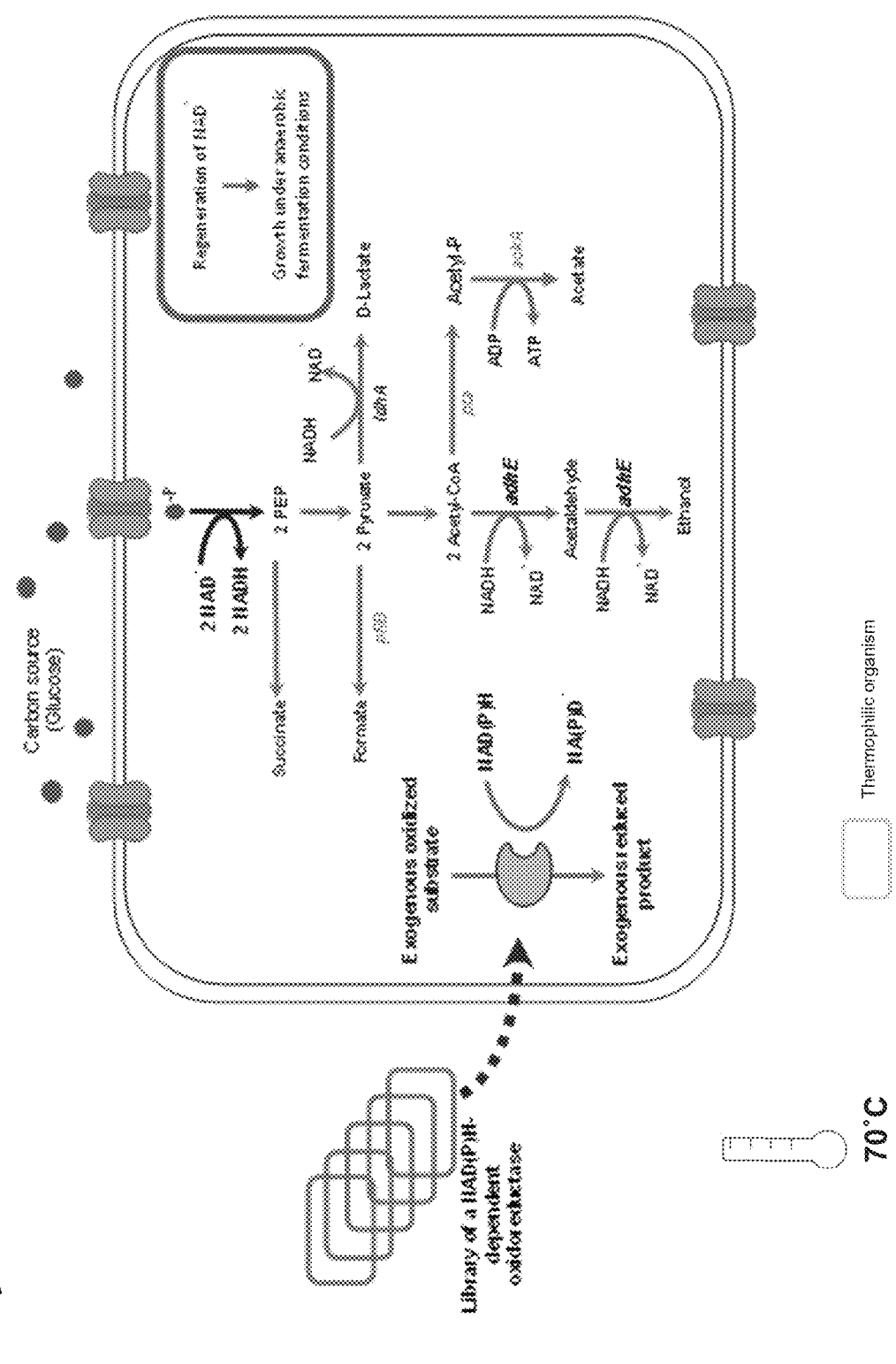
Figure 10:
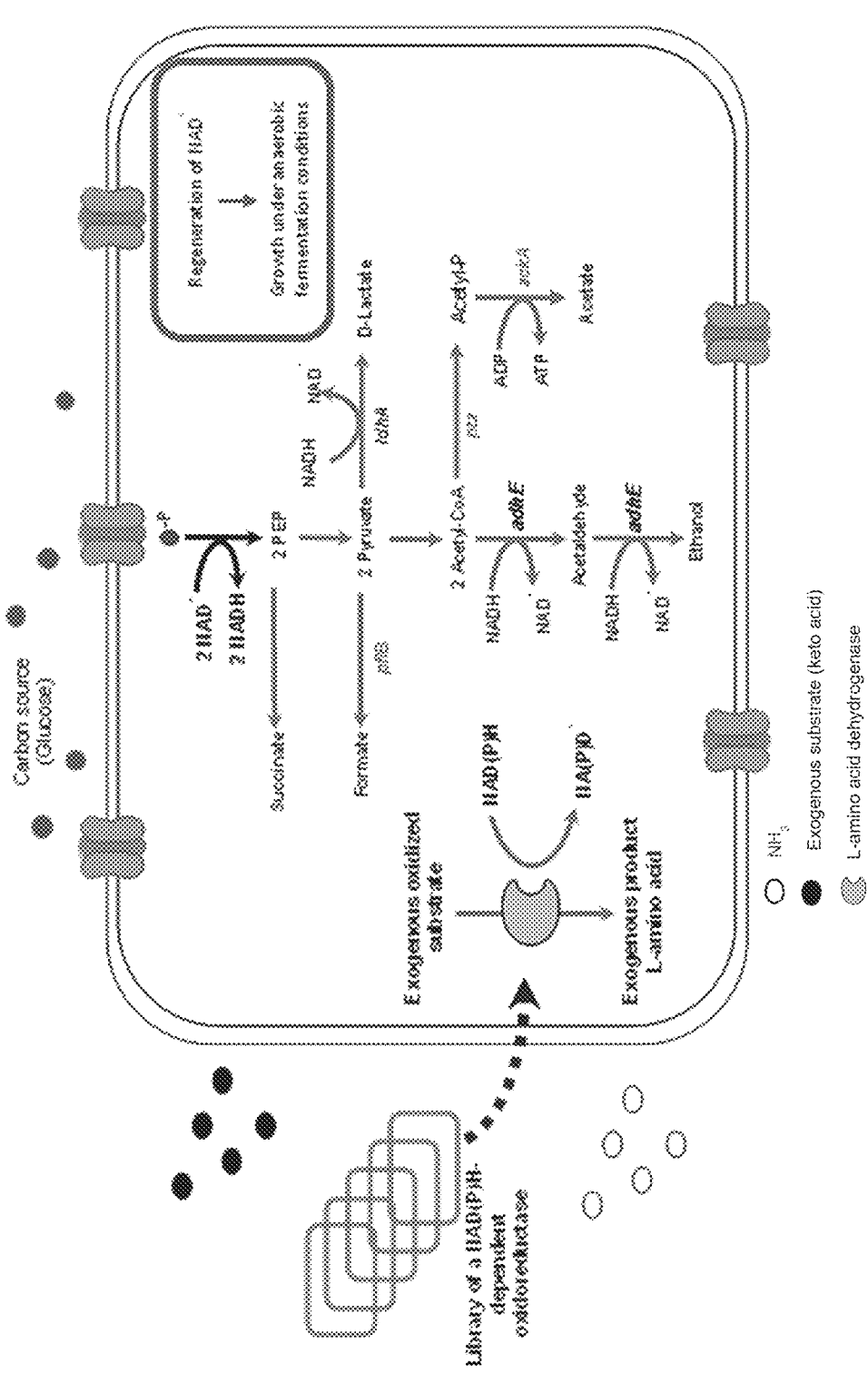
Figure 11:
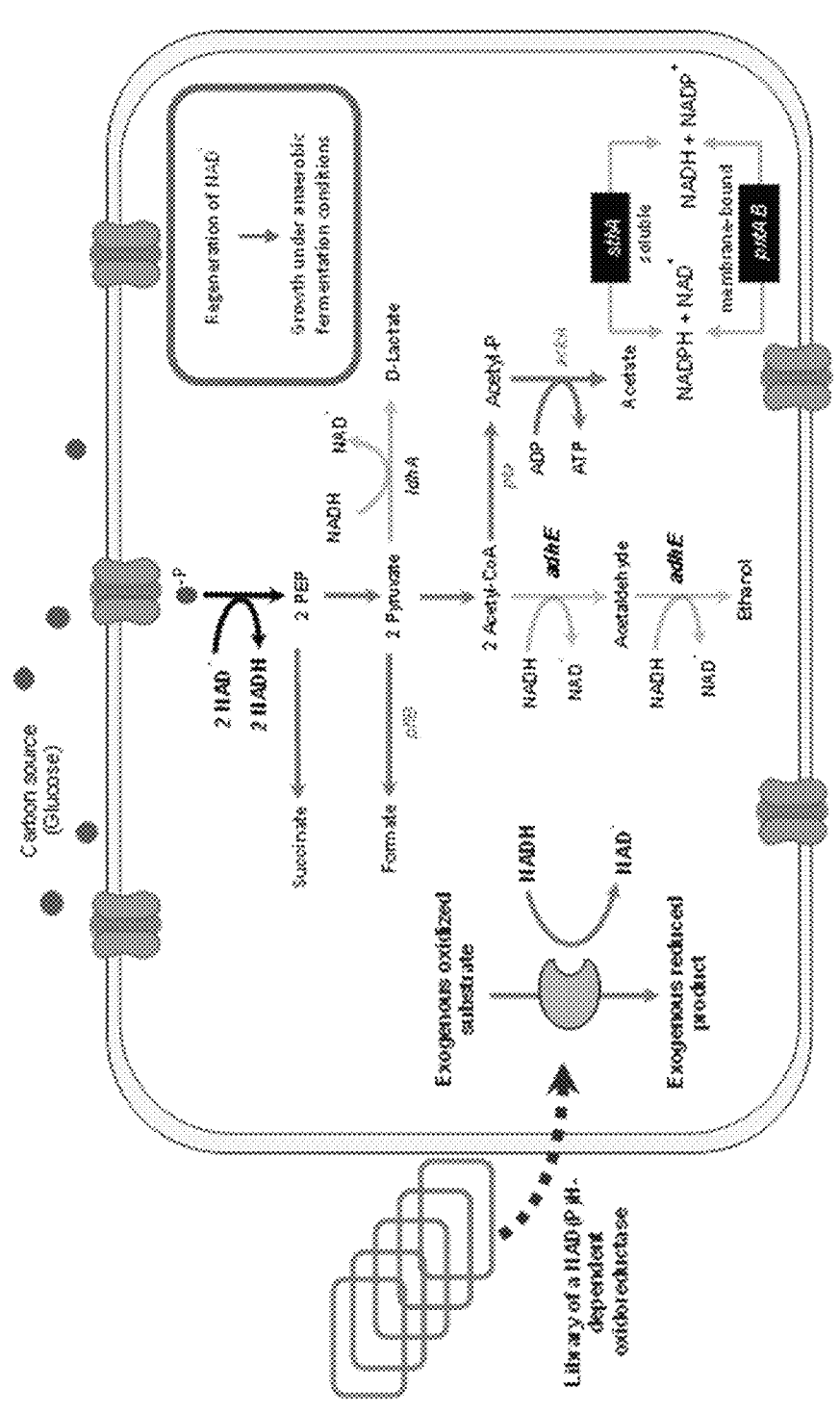
Figure 13:
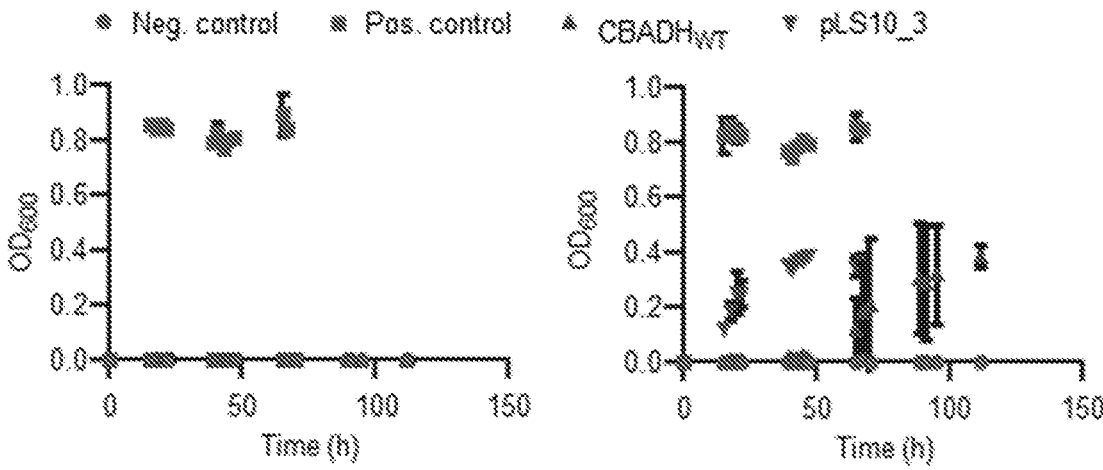
Figure 13:
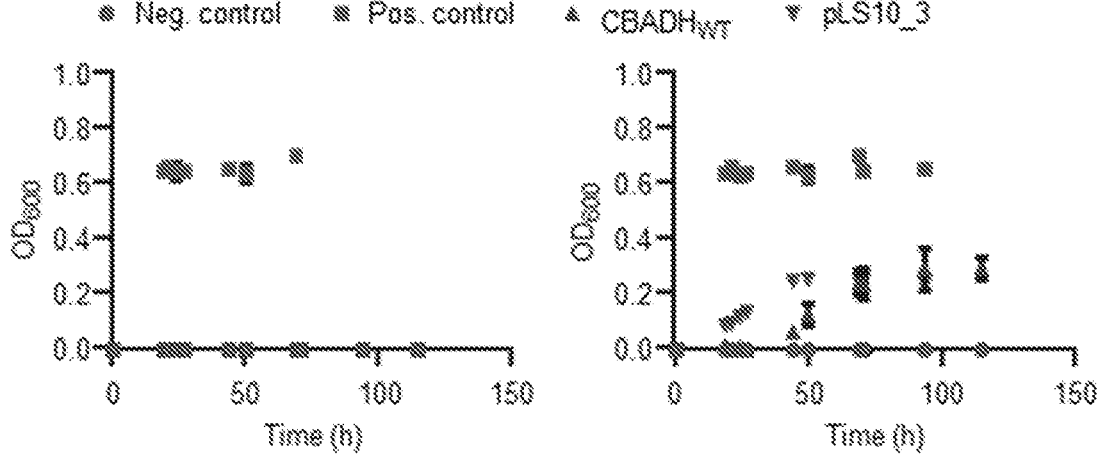
Figure 13:
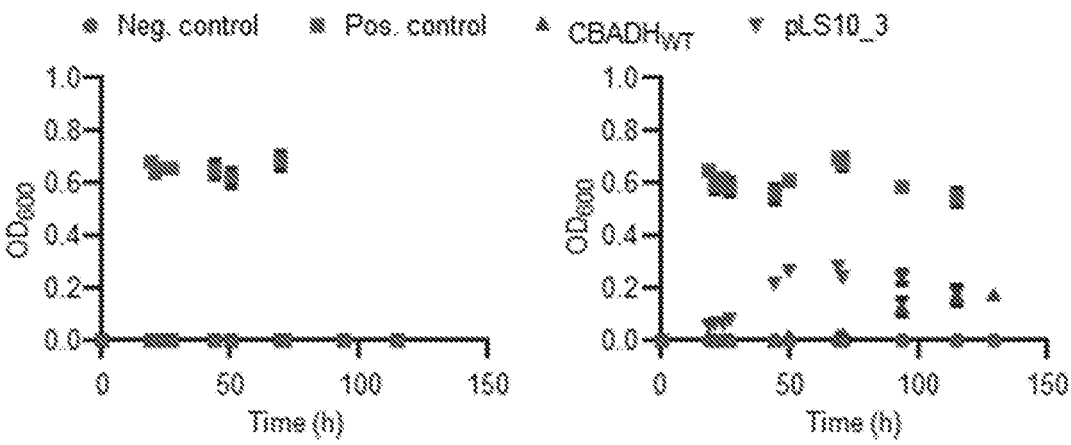
Figure 13:
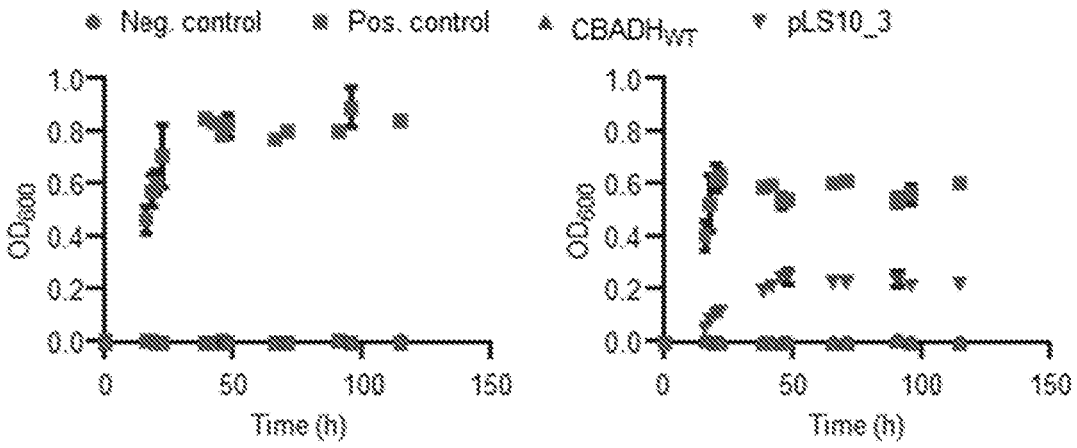
Figure 14:
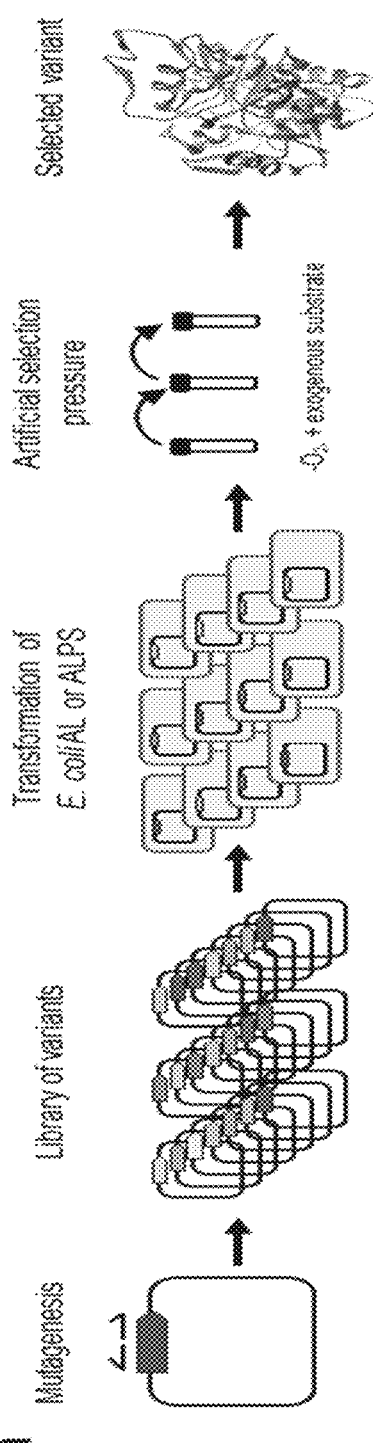
Figure 14:
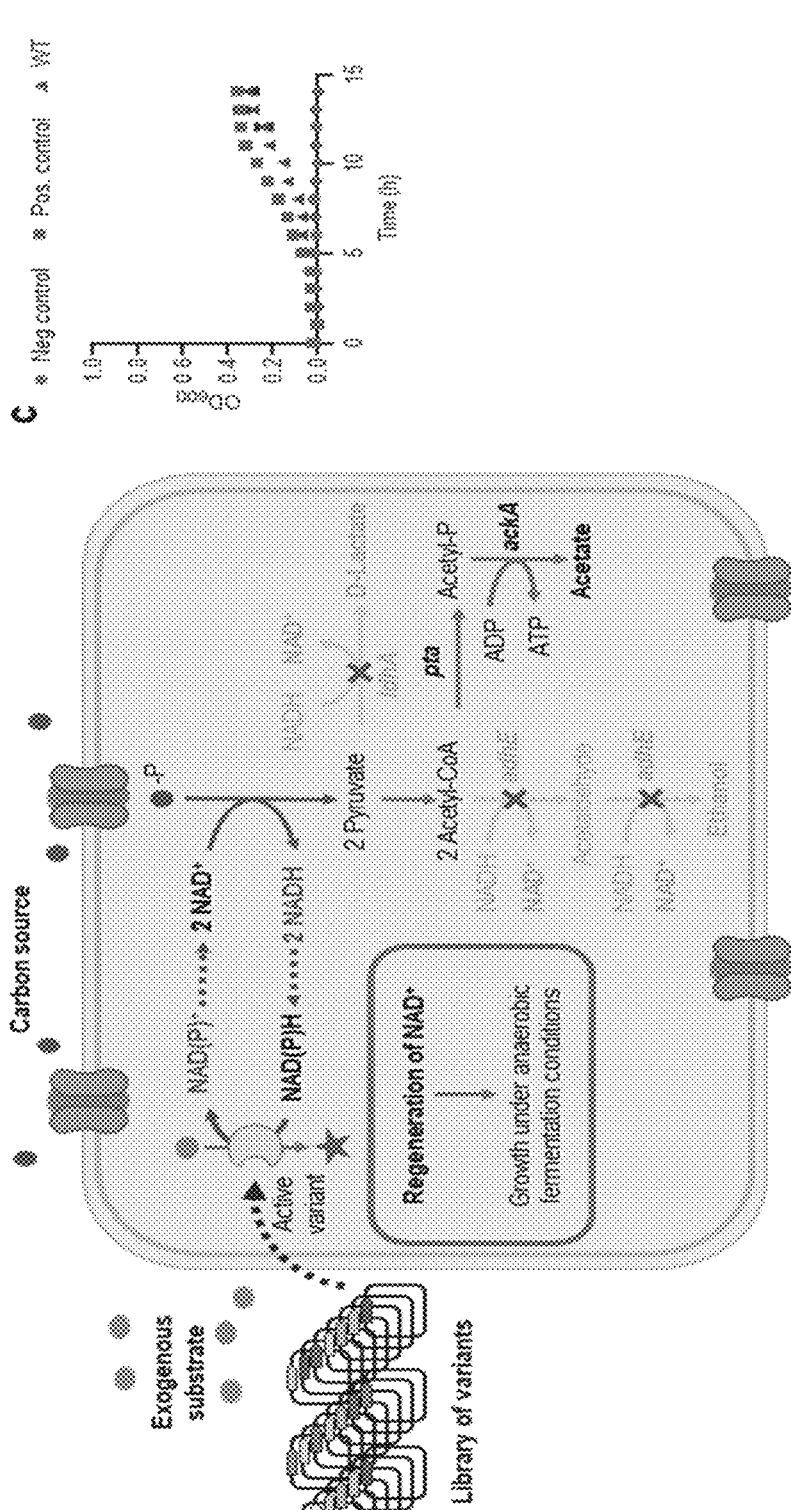
Figure 14:
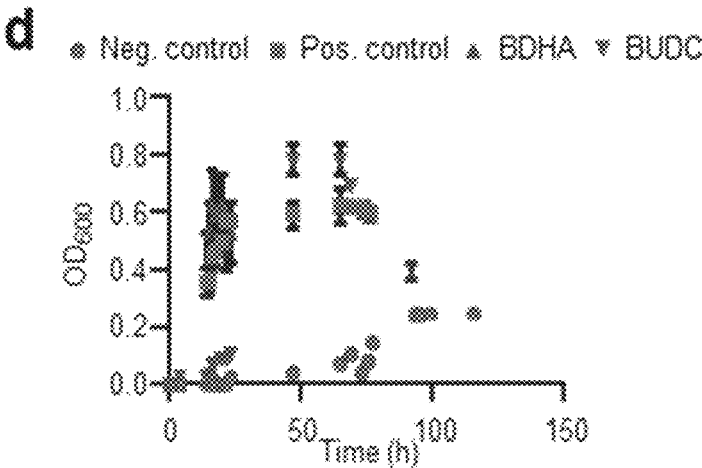
Figure 14:
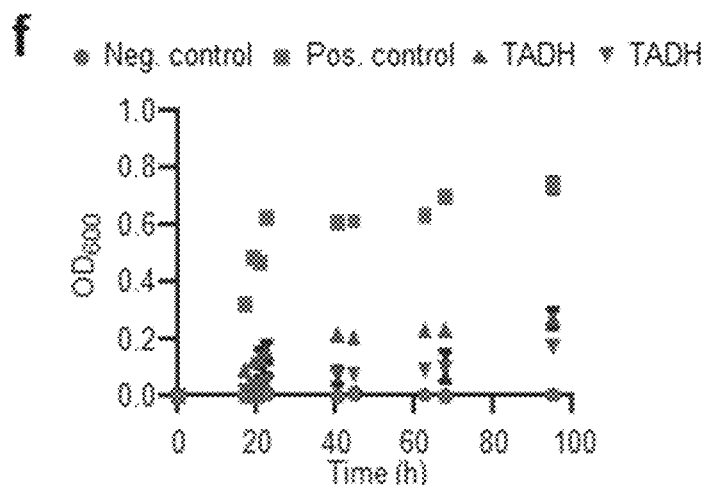
Figure 14:
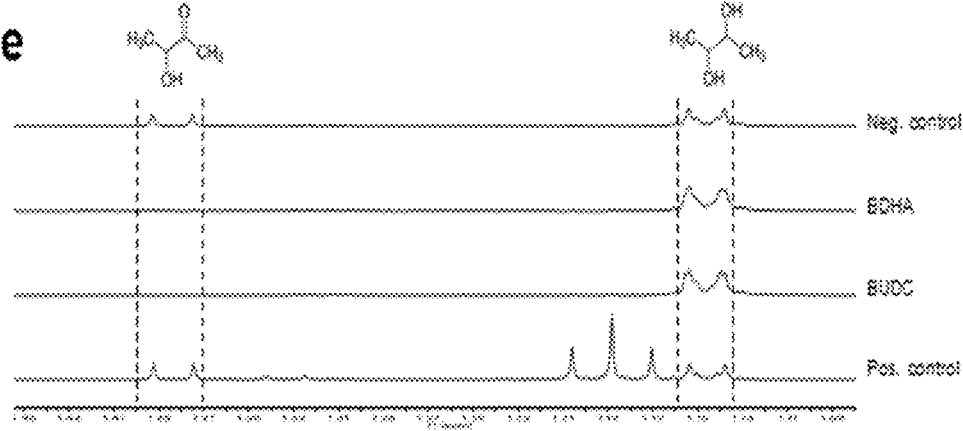
Figure 14:
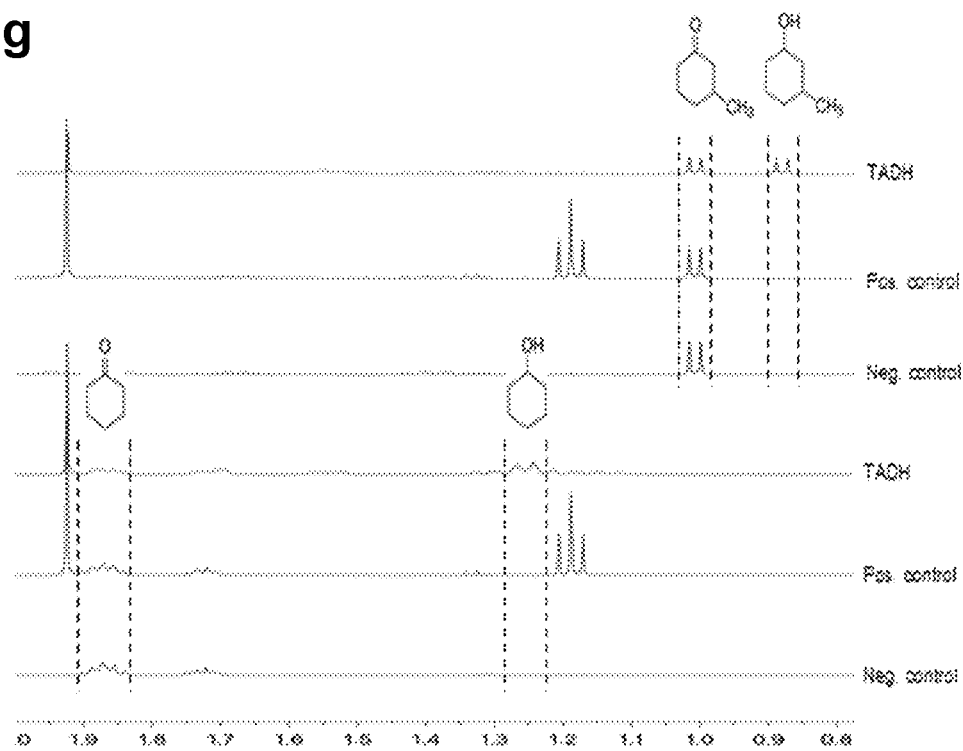
Figure 15:
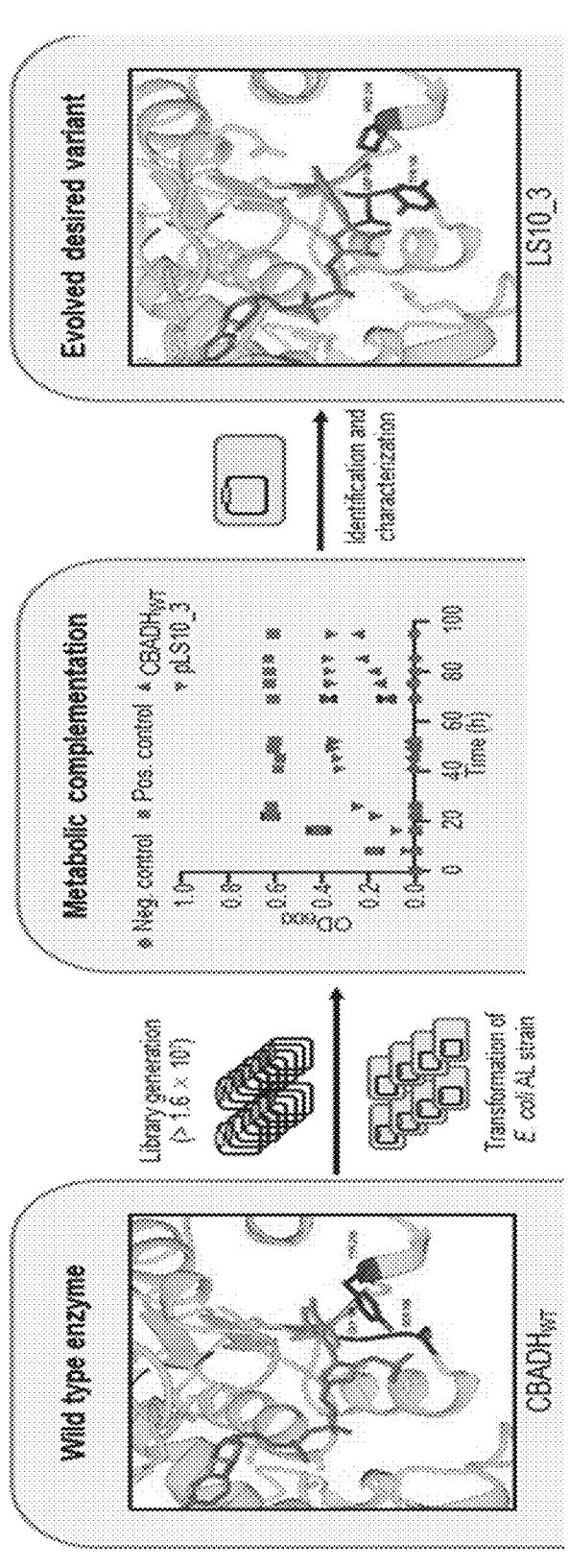
Figure 16:
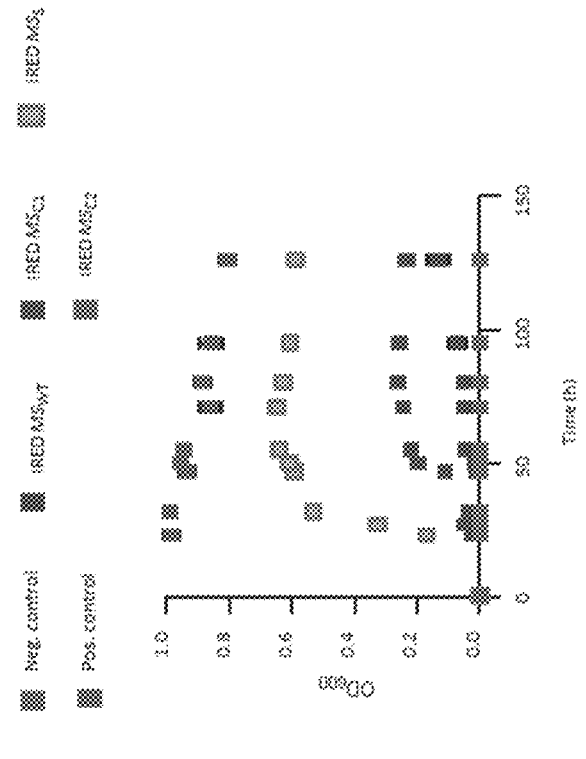
Figure 16:
Figure 16:
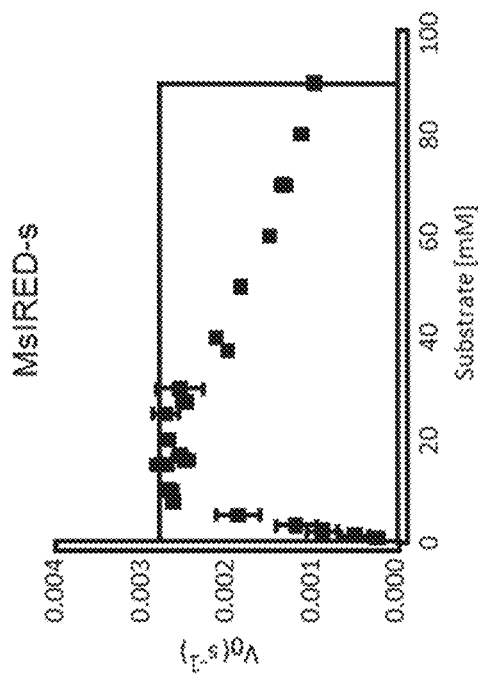
Figure 16:
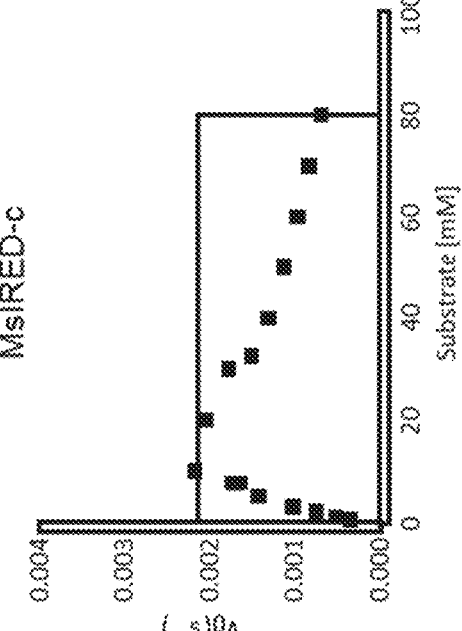
Figure 17:
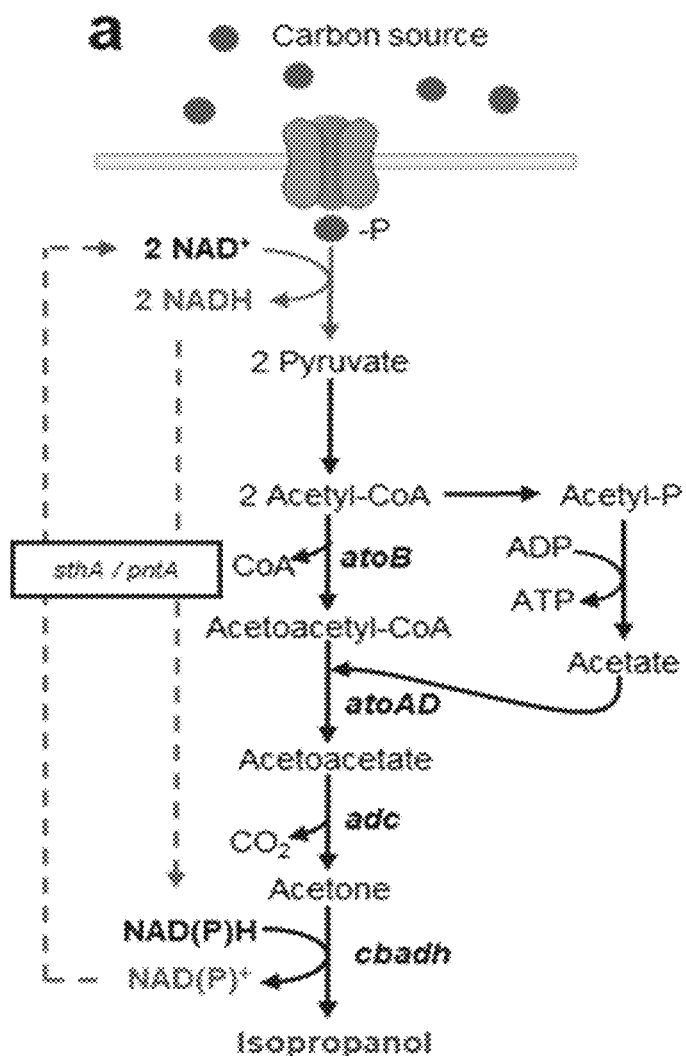
Figure 17:
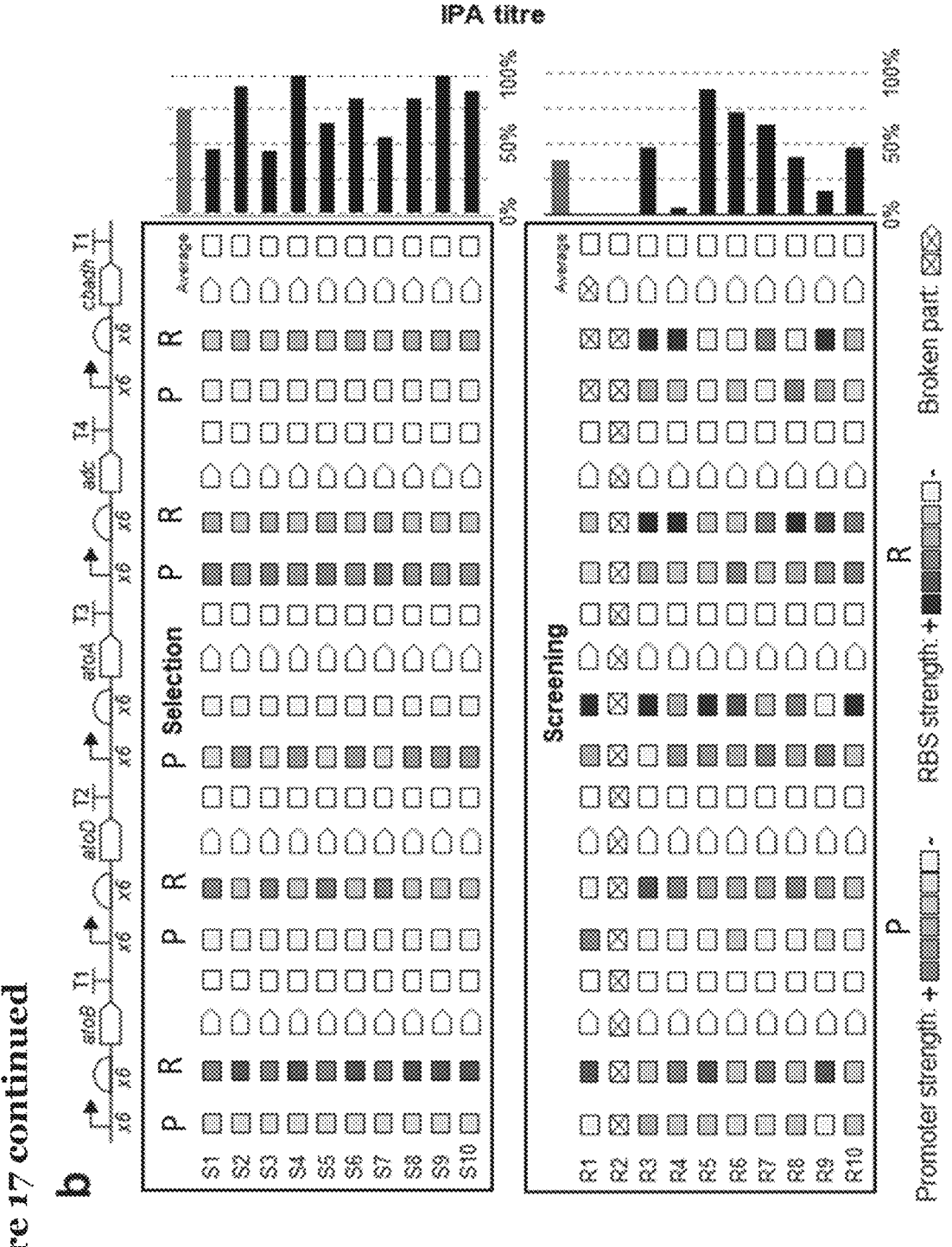
Figure 18:
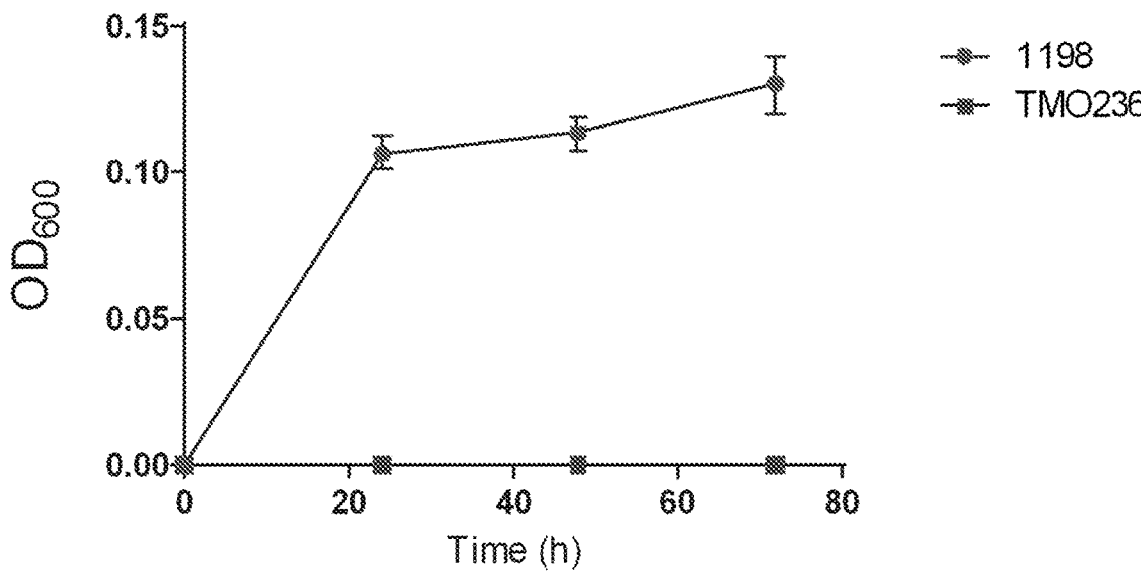
Figure 19A:
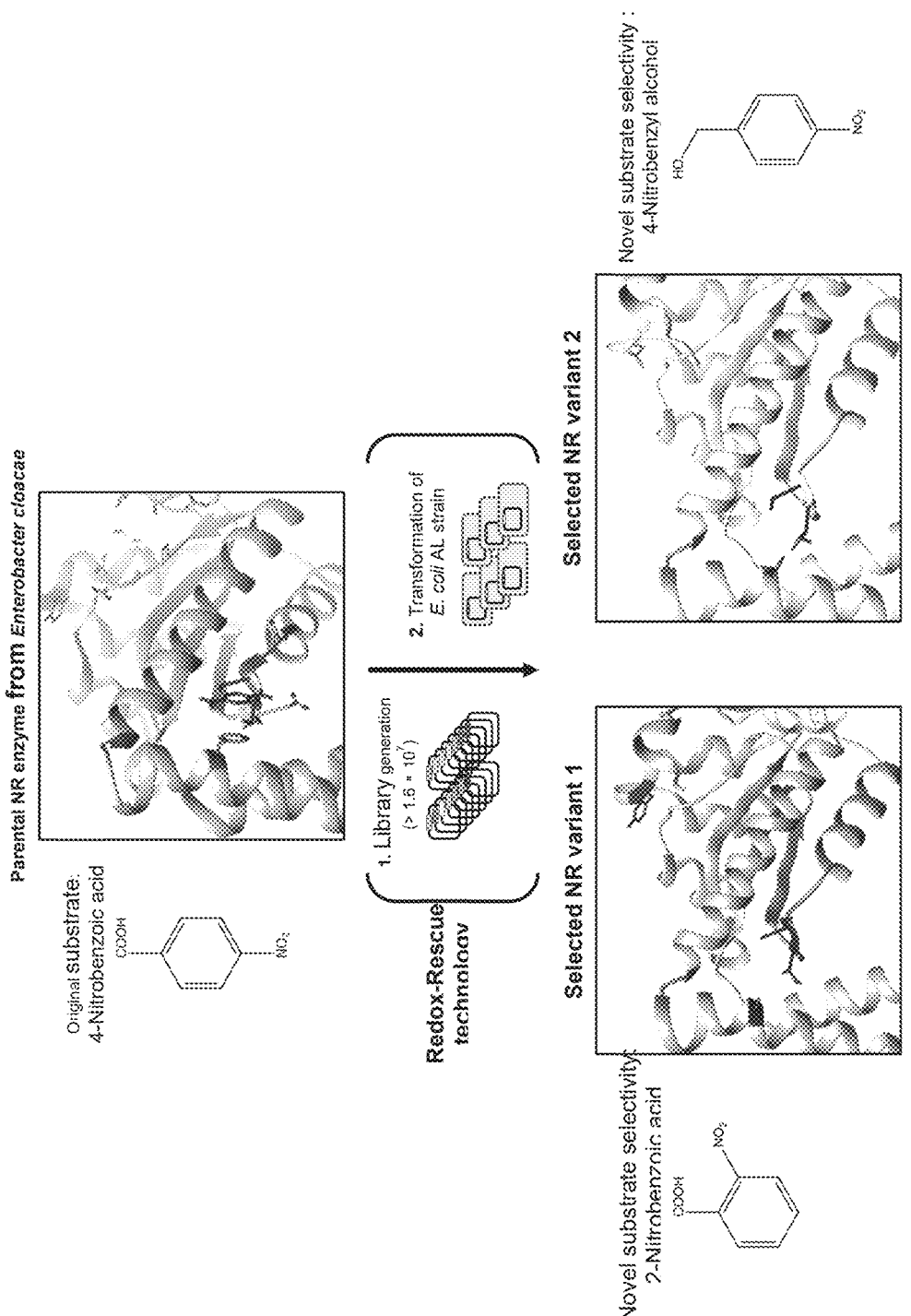
Figure 19B:
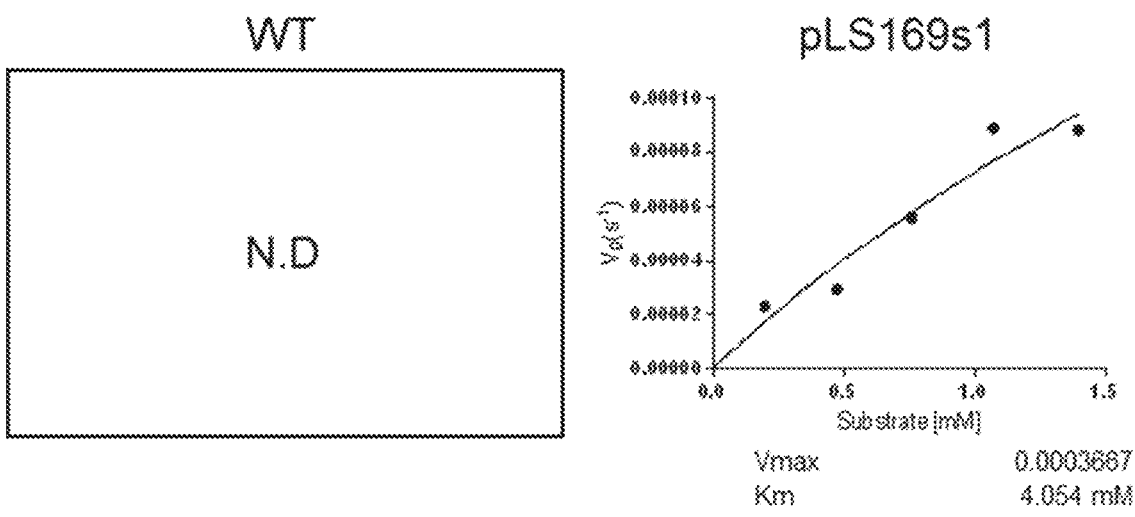
Figure 19B:
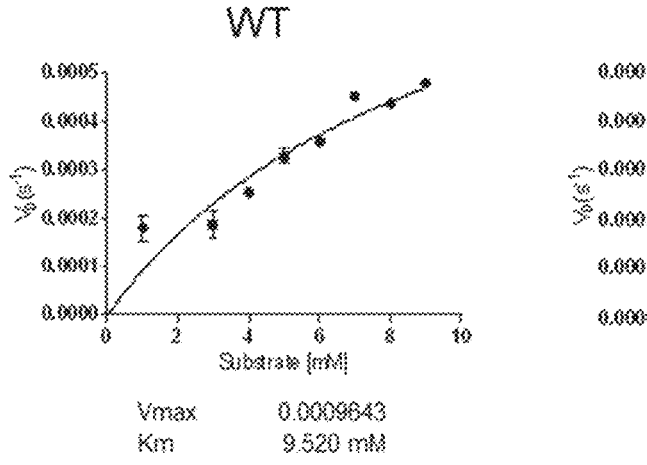
Figure 19B:
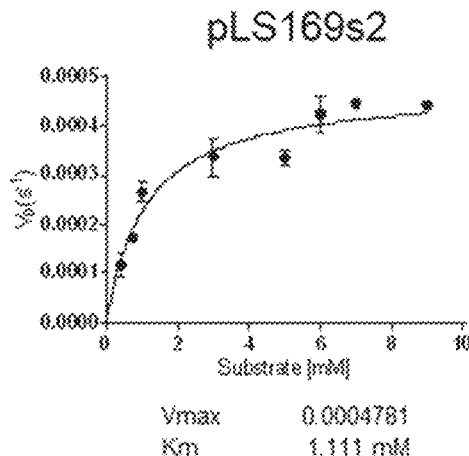

FIG. 8 is a schematic representation of one embodiment of the selection system of the invention wherein cells are transformed with a lipase and cultured in media supplemented with an ester or another molecule which the lipase can use as a substrate, yielding a molecule that can be oxidized by either an endogenous NADH-dependent oxidoreductase natively present in the cells transformed with the lipase or an exogenous NADH-dependent oxidoreductase with which the cells are also transformed;

FIG. 9 is a schematic representation of one embodiment of the selection system of the invention relating to the development of thermostable enzymes utilizing a thermophilic organism;

FIG. 10 is a schematic representation of one embodiment of the selection system of the invention wherein the polypeptide of interest is an L-amino acid dehydrogenase;

FIG. 11 shows a schematic representation of the LS5 strain. LS5 strain includes further metabolic defects in addition to those already present in LS1: both sthA and pntAB transhydrogenase-encoding genes were deleted. This removes the ability to balance the redox pools of NAD and NADP, thus making the strain unable to grow anaerobically unless transformed with a strictly NADH-dependent oxidoreductase whose substrate is present in the media;

Figure 12:
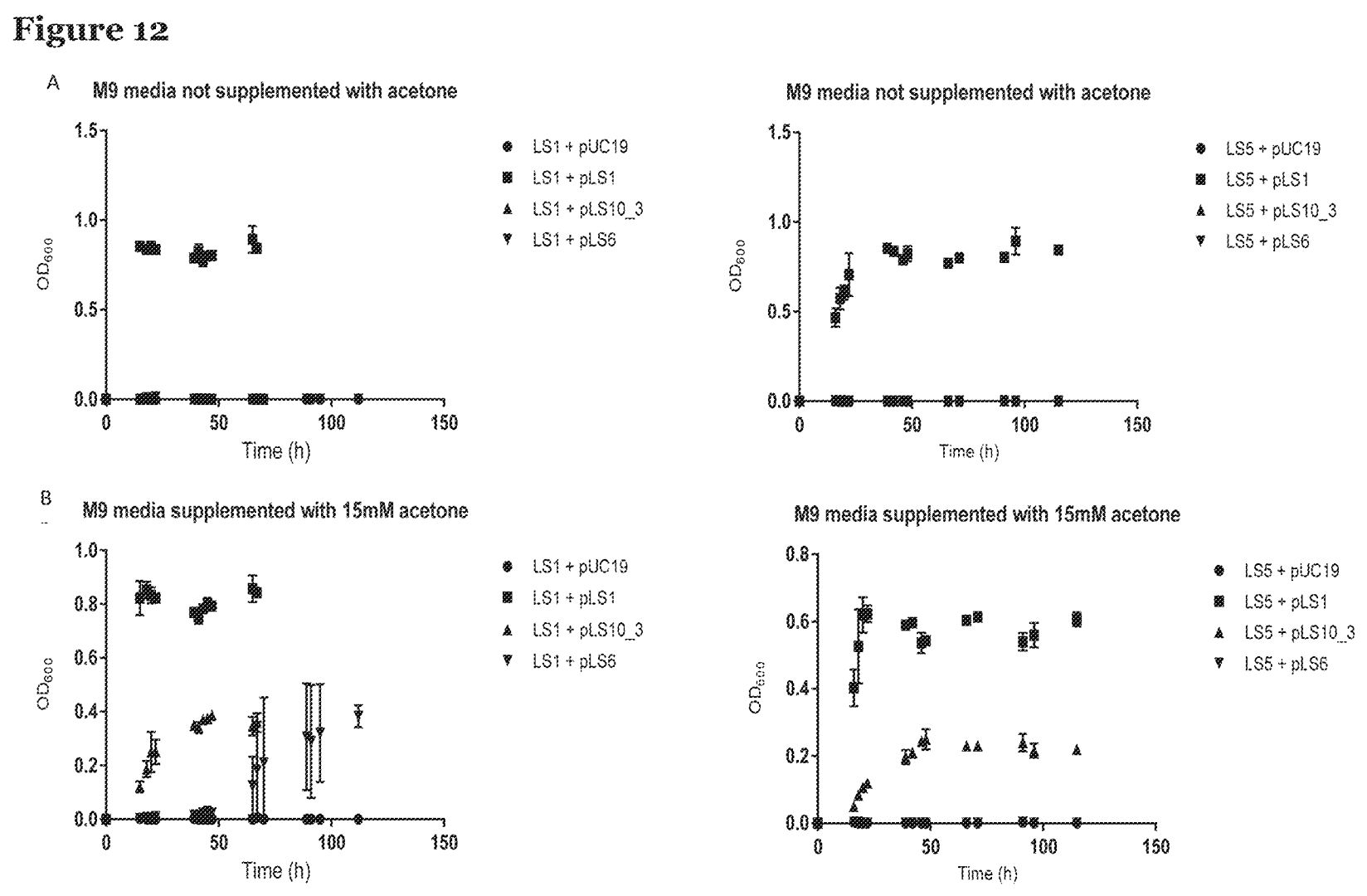

FIG. 12 shows growth curves showing that LS5 requires transformation with a strictly NADH-dependent oxidoreductase to grow anaerobically. a) Both LS1 and LS5 strains are unable to grow anaerobically in media lacking acetone, even when transformed with NAD(P)H-dependent oxidoreductases since they cannot regenerate oxidized cofactor because of the lack of the substrate. b) When the media is supplemented with acetone, LS1 strain is able to grow aerobically when transformed with either NADH-dependent or NADPH-dependent CBADH. However, LS5 strain is only able to grow anaerobically when transformed with NADH-dependent CBADH;

FIG. 13 shows a quadruple mutant strain for strict selection of NAD(H)-dependent oxidoreductases. For each *E. coli* mutant strain, anaerobic growth with (right panels) and without (left panels) acetone supplemented to the culture media was followed. a, AL mutant (ΔadhE ΔldhA). b, ALS mutant (ΔadhE ΔldhA ΔsthA). c, ALP mutant (ΔadhE ΔldhA ΔpntA). d, ALPS mutant (ΔadhE ΔldhA ΔpntB ΔsthA). Anaerobic growth of cells with at least one active transhydrogenase was recovered upon transformation of either an NADH or an NADPH-dependent oxidoreductase. However, in the case of ALPS cells, where both transhydrogenases were knocked-out, only the NADH-dependent enzyme restored anaerobic growth, which may indicate that metabolic complementation by NADPH-dependent enzymes is mediated by transhydrogenases;

FIG. 14 shows an overview of the metabolic complementation selection system. a, Schematic of the main steps for obtaining a novel biomolecule variant with the inventor's selection system. b, Overview of metabolic complementation within AL mutant cells. In AL mutant cells, both adhE and ldhA are knocked-out, which prevents them from regenerating oxidized NAD+ under anaerobic conditions. Since oxidized NAD+ is required for obtaining a constant supply of ATP through anaerobic fermentation of glucose, these cells are unable to grow anaerobically. Only upon transformation with a plasmid encoding a biomolecule able to restore the oxidation NADH (and addition to the media of the required substrate if necessary) cells overcome their metabolic impairment and anaerobic growth is restored. c, Recovery of anaerobic growth with endogenous adhE. AL cells transformed with adhE (Positive control) were able to grow anaerobically similarly to the WT cells, unlike untransformed AL cells (Negative control). d, Recovery of anaerobic growth with acetoin reductases from *Bacillus subtilis* (bdhA) and *Klebsiella pneumoniae* (budC). Cells transformed with either of the reductases displayed levels of anaerobic growth similar to the positive control, demonstrating that metabolic complementation can also be achieved with exogenous reductases. Untransformed cells also grew in media with acetoin, although with a much longer lag phase, possibly due to the presence of an endogenous acetoin reductase in the *E. coli* genome. e, NMR spectra of the fermentation broth of AL cells complemented with bhdA and budC. In both cases, the supplied acetoin was consumed and the reduced product, 2,3-butanediol, was produced. 2,3-butanediol was also observed in the fermentation broth of untransformed cells. f, Recovery of anaerobic growth with *Thermus* sp. ATN1 alcohol dehydrogenase. AL cells transformed with TADH grew anaerobically when supplemented with cyclohexanone (triangle) or 3-methylcyclohexanone (inverted triangle) (both substrates of TADH). g, NMR spectra of the fermentation broth of AL cells complemented with TADH. The alcohol corresponding to the ketone supplemented to the culture media was detected in both cases;

FIG. 15 shows the workflow of producing the variant CBADH and shows the crystal structure of pLS10 3 bound to NADH, obtaining insight into the structural basis of cofactor preference reversal;

FIG. 16 shows the evolution and characterization of a novel NADH-dependent imine reductase. a, Overimposition of a prediction of the structure of MsIRED-s (pLS133_1) (pink) and a homology model of WT MsIRED based on the crystal structure of 3ZHB (grey), with the bound NADPH cofactor displayed in orange. Structural analysis suggests that the residue substitutions present in MsIRED-s destroy the electrostatic interactions established in the WT enzyme by positively charged residues with the 2' phosphate of NADPH. b, Comparison of anaerobic growth in media with 2-methylpyrroline for cells transformed with WT MsIRED, previously engineered NADH-dependent MsIRED variants and MsIRED-s Anaerobic growth occurred to the largest extent, and with the shortest lag phase, when cells were transformed with MsIRED-s. c, Activity assays of the best previously described NADH-dependent MsIRED variant (left) and MsIRED-s (right). MsIRED-s1 had a higher affinity for the substrate, as shown by its lower Km. Furthermore, the extent of substrate inhibition was reduced in MsIRED-s, which also displayed a higher activity at the optimal substrate concentration;

FIG. 17 shows a library of pathways for isopropanol production based on the combination of genes previously designed by Hanai et al (*Clostridium acetobutylicum* acetyl-CoA acetyltransferase (thl) and acetoacetate decarboxylase (adc), *Escherichia coli* acetoacetyl-CoA transferase (atoAD) and CBADH). The figure also shows a comparison of isopropanol production under aerobic conditions was compared for randomly selected variants, variants selected in plates and variants selected in plates that grew in anaerobic liquid cultures (FIG. 17*b*);

FIG. 18 shows the growth curve under anaerobic conditions of WT *Geobacillus thermoglucosidasius* (1198) and mutant TMO0236 *Geobacillus thermoglucosidasius*. Thus highlighting that thermophilic organisms may be utilised for the selection methods of the invention;

FIGS. 19*a* and 19*b* shows the improved kinetic properties of the variant nitroreductases described in the examples; and FIG. 20 shows the isopropanol variant clones comprising variant promoters, RBS and terminator sequences. Sequence ID numbers are, starting from the Promoter J23100 and going down the figure to the terminator T4 (ECK120029600): SEQ ID No: 90 to 105.

MATERIALS AND METHODS

Plasmid Construction

The oligonucleotides listed below in Table 1 and synthetic genes listed in Table 2 were used to construct the plasmids with reductases for metabolic complementation. Table 3 lists the plasmids that were used and generated.

TABLE 1

Oligonucleotides used in this project

| Oligo ID | Sequence (5' → 3') | Source | Description |
|---|---|---|---|
| oligoLS19 | CCGTTCGCATGCAGGAGGTAC-GAACACATGGCTGTTACTAA - SEQ ID No: 4 | IDT DNA | adhE SphI (F) |
| oligoLS20 | GCTGAAGGATCCTTAAGCGGATTTTTTCG - SEQ ID No: 5 | IDT DNA | adhE BamHI (R) |
| oligoLS21 | CCGTTCG-CATGCCAATCTTAATCAAATCAGACAGA-GAGAGTACAATATGAAAAAAGTCGCAC-TTGT- SEQ ID No: 6 | IDT DNA | budC SphI (F) |
| oligoLS22 | TTCAGCGGATCCTTAGTTAAACAC-CATCCCGCCGTCGAT- SEQ ID No: 7 | IDT DNA | budC BamHI (R) |
| oligoLS23 | CCGTTCGCATGCAGGAGGTAC-GAACACATGAAGGCAGCAAGATG- SEQ ID No: 8 | IDT DNA | bdhA SphI (F) |
| oligoLS24 | GCTGAAGGATCCTTAG-TTAGGTCTAACAAGGATTTTGACT- SEQ ID No: 9 | IDT DNA | bdhA BamHI (R) |
| oligoLS87 | GTTCGCATGCATTCGGATCTATACAGA-TAAGGAGAAAGAGATGAAAGGCTTT-GCCATGCT- SEQ ID No: 10 | IDT DNA | sadh Clostridium NADPH SphI (F) |
| oligoLS88 | CTTCCATGGATCCTCACTATTAGAGGA-TAACTACGGCC- SEQ ID No: 11 | IDT DNA | sadh Clostridium NADPH BamHI (R) |
| oligoLS112 | CTTGGCGGCCTCAACGCAAA-TAGGNNNNNNNNNGACACCAA-TAATCCGACCTGC- SEQ ID No: 12 | IDT DNA | CBADH random mutagenesis 198, 199 and 200 (R) |
| oligoLS113 | TTCTACGGCGCGAC-CGACATTCTGAATNNNAAAAATGGCCATAT TGTGGAC- SEQ ID No: 13 | IDT DNA | CBADH random mutagenesis 218 (F) |
| oligoLS162 | GCTGAAGGATCCTTAG-TGGTGGTGGTGGTGGTGGTTAGGTCTAAC AAGGATTTTGA- SEQ ID No: 14 | IDT DNA | BDAH 6xHis tag C-terminus |

TABLE 1-continued

| Oligo ID | Sequence (5' → 3') | Source | Description |
|---|---|---|---|
| oligoLS163 | GCTGAAGGATCCTTAG-TGGTGGTGGTGGTGGTGGAGGATAAC-TACGGCCTTAATGAGA- SEQ ID No: 15 | IDT DNA | CBADH 6xHis tag C-terminus |
| oligoLS168 | CCGTTCGCATGCAGGAGGTAC-GAACACATG- SEQ ID No: 16 | IDT DNA | ADH from *Thermus* sp ATN1 SphI F |
| oligoLS169 | TTCAGCGGATCCTTATCCGCGAACTACAA-GCAAT- SEQ ID No: 17 | IDT DNA | ADH from *Thermus* sp ATN1 BamHI R |
| oligoLS170 | GCTGAAGGATCCTTAG-TGGTGGTGGTGGTGGTGTCCGCGAAC-TACAAGCAATACCT- SEQ ID No: 18 | IDT DNA | ADH from *Thermus* sp ATN1 6xHis tag C-terminus |
| oligoLS208 | TTCAGCGGATCCAATGTATCTGCATGAA-GCACAGACCCACCAGTTACTGG- SEQ ID No: 19 | IDT DNA | sthA-pMAK705 BamHI |
| oligoLS209 | TTCAGCaagcttCATTAAAC-CGCTCTCATCAACCATGGTCAGACCCAG-TTCG- SEQ ID No: 20 | IDT DNA | sthA-pMAK705 HindIII |
| oligoLS216 | TTCAGCGGATCCGAAACGAC-CAGAGCCGCCAGGTTCA- SEQ ID No: 21 | IDT DNA | pntA-pMAK705 BamHI |
| oligoLS218 | TTCAGCaagcttCAGGAGGGTGTTCTTAA-GCTTCATAAAAATAATCCTTCGCCTTGCGC-SEQ ID No: 22 | IDT DNA | pntA-pMAK705 HindIII |
| oligoLS228 | AAGGGGTT-GGTCTCATGTGGCTCTTCGATGttaaaggatgaagtaattaaacaaattagcacg- SEQ ID No: 23 | IDT DNA | ADC- Lvo |
| olilgoLS229 | AAGGGGTTGGTCTCTGGTCTTAC-GCTCTTCATTActtaagataatcata-tataacttcagctctaggc- SEQ ID No: 24 | IDT DNA | ADC- Lvo |
| oligoLS232 | AAGGGGTT-GGTCTCATGTGGCTCTTCGATGaaaggctttt-gccatgctg- SEQ ID No: 25 | IDT DNA | CBADH- Lvo |
| oligoLS233 | AAGGGGTTGGTCTCTGGTCTTACGCTCT TCATTAgaggataactacggccttaatgag- SEQ ID No: 26 | IDT DNA | CBADH- Lvo |
| oligoLS234 | AAGGGGTTGGTCTCATGTGGCTCTTCG ATGaaaacaaaattgatgacattacaagacg- SEQ ID No: 27 | IDT DNA | AtoD- Lvo |
| oligoLS235 | AAGGGGTTGGTCTCTGGTCTTACGCTCT TCATTAaaatcaccccgttgcgtattc- SEQ ID No: 28 | IDT DNA | AtoA- Lvo |
| oligoLS242 | AAGGGGTTGGTCTCATGTGGCTCTTCG ATGGATGCGAAACAACGTATTGCGC-SEQ ID No: 29 | IDT DNA | AtoA- Lvo |
| oligoLS243 | AAGGGGTTGGTCTCTGGTCTTACGCTCT TCATTATTTGCTCTCCTGTGAAACGATG ATGTG- SEQ ID No: 30 | IDT DNA | AtoD- Lvo |
| oligoLS244 | TTCAGCGGATCCTGTCTGTTTTGCGGTC GCCAG- SEQ ID No: 31 | IDT DNA | ldhA pMAK705 bamHI |
| oligoLS245 | TTCAGCaagcttCAAGCAGAATCAAGTTCT ACCGTGC- SEQ ID No: 32 | IDT DNA | ldhA pMAK705 HindIII |

TABLE 7

| Other oligonucleotides used in this project |
| --- |

PLS98  oligoLS294  GCAGCCATATGatgaaaggctttgccatgctgggtattaacaaattagg- SEQ ID
                    No: 42
       oligoLS295  TTATTGCTCAGCTTAgaggataactacggccttaatgagatctttaggtttatctttcat
                    gag- SEQ ID No: 43 pLS131 oligoLS344  ACGATAATATCGCTGCGTTTAAC- SEQ ID No: 44
       oligoLS345  CTGGCAAAACTGGGCGCACATC- SEQ ID No: 45
       oligoLS342  CGGTTCGCTACGGGCTTTTTCATATTCCCACACCGTGGTCG-
                    SEQ ID No: 46
       oligoLS343  GGTTAATGTGATTGATTATGACACCTCTGATCAGGTTCTGCGCC
                    AAGAC- SEQ ID No: 47 pLS132 oligoLS344  ACGATAATATCGCTGCGTTTAAC- SEQ ID No: 48
       oligoLS345  CTGGCAAAACTGGGCGCACATC- SEQ ID No: 49
       oligoLS343  GGTTAATGTGATTGATTATGACACCTCTGATCAGGTTCTGCGCC
                    AAGAC- SEQ ID No: 50
       oligoLS346  CGGTTCGCTCGCGGCTTTTTCATATTCCCACACCGTGGTCG-
                    SEQ ID No: 51 pLS133 oligoLS337  GCTGAgaagaccGACCACGGTGTGGNNNNNNNNNAAAGCCNNNA
                    GCGAACCGCTGGCAAAACTG- SEQ ID No: 52
       oligoLS338  GCTGAgaagaccgtGGTCGTGTAGCCAGATTGCAGGAATGCTTTAAT
                    CAGTGCGGAGCCCATACGGCC- SEQ ID No: 53 pLS161 oligoLS358  tctctGAAGACTCCTTAGTGGTGGTGGTGGTGGTGTTTCAGGAAGC
                    GGGTCAGAATTGCAAAG- SEQ ID No: 54
       oligoLS359  tctctGAAGACAacATGAAACCGACCCTGACCGTTATTGGC- SEQ
                    ID No: 55 pLS162 oligoLS358  tctctGAAGACTCCTTAGTGGTGGTGGTGGTGGTGTTTCAGGAAGC
                    GGGTCAGAATTGCAAAG- SEQ ID No: 56
       oligoLS359  tctctGAAGACAacATGAAACCGACCCTGACCGTTATTGGC- SEQ
                    ID No: 57 pLS164 oligoLS358  tctctGAAGACTCCTTAGTGGTGGTGGTGGTGGTGTTTCAGGAAGC
                    GGGTCAGAATTGCAAAG- SEQ ID No: 58
       oligoLS359  tctctGAAGACAacATGAAACCGACCCTGACCGTTATTGGC- SEQ
                    ID No: 59 pLS169 oligoLS363  tctctGAAGACTCGGTGCTGGCTACAATGAAGTGCCACGGCTGGGA
                    GTTNNNNNNGGACGGGCTGTACTGC- SEQ ID No: 60
       oligoLS366  ctctGAAGACCAGTGGATGGCGAAGCAGGTTTACCTGAACGTCGG-
                    SEQ ID No: 61
       oligoLS364  ctctGAAGACAGCACCGAGGAAGGAAAAGCGCGCGTGGCGAAGTC
                    CGCTGCGGGCACCNNNGTGTTCAACGAACG- SEQ ID No: 62
       oligoLS365  tctctGAAGACATCCaCTGGTCGTCATCTTTCAGATCCACGCGGTGC
                    ATGTCGGCNNNGTAGGTGCGGCC- SEQ ID No: 63

PLS46  oligoLS230  AAGGGGTTGGTCTCATGTGCTCTTCGatgaaaaattgtgtcatcgtcagtgcg
                    gtacg- SEQ ID No: 64
       oligoLS231  AAGGGGTTGGTCTCTGGTCTTACGCTCTTCAttaattcaaccgttcaatcac
                    catcgcaattccc- SEQ ID No: 65 pLS47  oligoLS234  AAGGGGTTGGTCTCATGTGGCTCTTCGATGaaaacaaaattgatgacatt
                    acaagacg- SEQ ID No: 66
       oligoLS243  AAGGGGTTGGTCTCTGGTCTTACGCTCTTCATTATTTGCTCTCCT
                    GTGAAACGATGATGTG- SEQ ID No: 67 pLS48  oligoLS235  AAGGGGTTGGTCTCTGGTCTTACGCTCTTCATTAtaaatcaccccgttgc
                    gtattc- SEQ ID No: 68
       oligoLS242  AAGGGGTTGGTCTCATGTGGCTCTTCGATGGATGCGAAACAACG
                    TATTGCGC- SEQ ID No: 69 pLS49  oligoLS228  AAGGGGTTGGTCTCATGTGGCTCTTCGATGttaaaggatgaagtaattaa
                    acaaattagcacg- SEQ ID No: 70
       oligoLS229  AAGGGGTTGGTCTCTGGTCTTACGCTCTTCATTActtaagataatcatat
                    ataacttcagctctaggc- SEQ ID No: 71

PLS50  oligoLS232  AAGGGGTTGGTCTCATGTGGCTCTTCGATGaaaggctttgccatgctgggt
                    attaac- SEQ ID No: 72
       oligoLS233  AAGGGGTTGGTCTCTGGTCTTACGCTCTTCATTAgaggataactacggc
                    cttaatgagatctttagg- SEQ ID No: 73 pLS63  oligoLS244  TTCAGCGGATCCTGTCTGTTTTGCGGTCGCCAG- SEQ ID No: 74
       oligoLS247  CACTGGAGAAAGTCTTATGTAATCTTGCCGCTCCCCTGCATTCCA
                    G- SEQ ID No: 75
       oligoLS245  TTCAGCaagcttCAAGCAGAATCAAGTTCTACCGTGC- SEQ ID No:
                    76

TABLE 7-continued

| Other oligonucleotides used in this project | | |
|---|---|---|
| | oligoLS246 | CAGGGGAGCGGCAAGATTACATAAGACTTTCTCCAGTGATGTTG AATC- SEQ ID No: 77 |
| pLS39 | oligoLS208 | TTCAGCGGATCCAATGTATCTGCATGAAGCACAGACCCACCAGT TACTGG- SEQ ID No: 78 |
| | oligoLS210 | AACAGGTAAGCCCTACCATGTAAAACTTTATCGAAATGGCCATC CATTCTTGCGCGG- SEQ ID No: 79 |
| | oligoLS209 | TTCAGCaagcttCATTAAACCGCTCTCATCAACCATGGTCAGACCCA GTTCG- SEQ ID No: 80 |
| | oligoLS211 | GCCATTTCGATAAAGTTTTACATGGTAGGGCTTACCTGTTCTTAT ACATAAAAGCAACAGAATGG- SEQ ID No: 81 |
| pLS40 | oligLS216 | TTCAGCGGATCCGAAACGACCAGAGCCGCCAGGTTCA- SEQ ID No: 82 |
| | oligLS217 | CCGATGGAAGGGAATATCATGTAAGGGGTAACATATGTCTGGAG GATTAGTTACAGCTGCATACATTGTTGCCGC- SEQ ID No: 83 |
| | oligoLS218 | TTCAGCaagcttCAGGAGGGTGTTCTTAAGCTTCATAAAAATAATC CTTCGCCTTGCGCAAA- SEQ ID No: 84 |
| | oligoLS219 | CCAGACATATGTTACCCCTTACATGATATTCCCTTCCATCGGTTT TATTGATG- SEQ ID No: 85 |

Dehydrogenase genes were amplified by PCR from either genomic DNA or gBlock synthetic DNA (IDT) (see Table 2) by using the corresponding oligonucleotides. The obtained PCR products were digested with SphI and BamHI restriction enzymes and then ligated with pUC19 using T4 DNA ligase. pUC19 was previously linearised by using the same restriction enzymes.

TABLE 2

List of Synthetic genes (gBlock)

| gBlock ID | Sequence (5' → 3') | Source | Description |
|---|---|---|---|
| gBlockLS3 | CCGTTCG- CATGCCAATCTTAATCAAATCAGACAGA- GAGAGTACAATATGAAAAAAGTCGCAC- TTGTTACCGGCGCCGGCCAGGGGATTGG- TAAAGC- TATCGCCCTTCGTCTGGTGAAGGATGGAT TTGCCGTGGCCATTGCCGATTATAAC- GACACCACCGCCAAA- GCGGTCGCCTCCGAAATCAAC- CAGGCCGGCGGCCGCGCCATGGCGGTGA AAGTGGATGTCTCCGAC- CGCGATCAGGTGTTT- GCCGCCGTCGAACAGGCGCGCAAAAC- GCTGGGCGGCTTCGAC- GTCATCGTCAACAAC- GCCGGCGTGGCGCCGTCCAC- GCCGATCGAGTCCATTACCCCGGA- GATTGTCGATAAAGTCTACAACATCAAC- GTTAAAGGGGTGATCTGGGG- CATTCAGGCGGCGGTCGAGGCCTTTAA- GAAAGAGGGTCACGGCGG- GAAAATCATCAAC- GCCTGTTCCCAGGCCGGCCACGTCGG- CAACCCGGAGCTGGCGGTATA- TAGCTCGAGTAAATTCGCCGTAC- GCGGCTTAACCCAGAC- CGCCGCTCGCGACCTCGCGCCGCTGGG- CATCACAGTCAACGGCTACTGCCCGGG- GATTGTCAAAAC- GCCAATGTGGGCCGAAATTGAC- CGCCAGGTGTCCGAAGCCGCCGGTAAAC- CGCTGGGTTACGGTACCGCCGAG- TTCGCCAAAC- GCATCACCCTCGGCCGCCTGTCCGAGCCG GAAGATGTCGCCGCCTGCGTCTCC- TATCTTGCCAGCCCGGATTCTGATTA- | IDT DNA | SphI/BamHI - sadh *Klebsiella pneumoniae* |

TABLE 2-continued

| gBlock ID | Sequence (5' → 3') | Source | Description |
|---|---|---|---|
| | TATGACCGGTCAGTCATTGCTGATCGAC-GGCGG-GATGGTGTTTAACTAAGGATCCGCTGAA - SEQ ID No: 33 | | |
| gBlockLS10 | CCGTTCGCATGCAGGAGGTAC-GAACACATGAAACCGACCCTGAC-CGTTATTGGCGCTGGCCGTATGGGCTCCG-CACTGATTAAAGCATTCCTGCAATCTGGC-TACACGACCACGGTGTGGAACCGTACCAAA-GCCAAAAGCGAACCGCTGG-CAAAACTGGGCGCACATCTGGCTGATAC-GGTGCGTGACGCCGTTAAACGCAGCGA-TATTATCGTGGTTAATGTGCTGGAT-TATGACACCTCTGATCAGCTGCTGCGCCAA-GACGAAGTGACGCGTGAACTGCGCGG-CAAACTGCTGGTTCAGCTGAC-CAGCGGTTCTCCGGCAC-TGGCTCGTGAACAGGAAAC-GTGGGCGCGCCAACATGGCATTGAT-TATCTGGACGGTGCGATCATGGCCACCCCG-GAT-TTTATTGGCCAGGCAGAATGCGCTCTGCTG-TACAG-TGGTTCCGCGGCCCTGTTCGAAAAACAC-CGTGCTGTCCTGAATGTGCTGGGCGGTGCCA-CCAGCCATGTCGGCGAAGATGTT-GGTCATGCCTCAGCACTG-GACAGCGCCCTGCTGTTTCAGATGTGGGG-CACCCTGTTCGGTACGCTGCAAGCACTGGC-TATTTCTCGCGCAGAAGGCATCCCGCTG-GAAAAAACCACGGCGTTTATCAAACTGAC-CGAACCGGTCACCCAGGGTGCCGTT-GCAGATGTCCTGACCCGTGTTCAG-CAAAATCGCCTGACCGCAGACGCTCAGAC-GCTGGCAAGTCTGGAAGCTCATAAC-GTGGCGTTCCAACAC-CTGCTGGCCCTGTGTGAAGAACGTAA-TATCCATCGCGGTGTTGCG-GATGCCATGTACTCCGTTATTCGTGAA-GCGGTCAAAGCCGGCCACGGTAAA-GATGACTTT-GCAATTCTGACCCGCTTCCTGAAA-TAAGGATCCTTCAGC - SEQ ID No: 86 | IDT DNA | RE:<br>SphI/BamHI -<br>IREDs *Myxococcus<br>stipitatus* |
| gBlockLS12 | catctGAAGACAacATGGA-TATCATTTCTGTCGCCCTGAAACGCCACTC-TACCAAGGCGTTCGACGCAA-GCAAAAAACTGACCGCGGAAGAAGCG-GAAAAAATCAAAACCCTGCTGCAG-TACAGCCCGTCCAGCAC-CAACTCCCAGCCGTGGCACTTCATT-GTAGCCAGCACCGAGGAAGGAAAA-GCGCGCGTGGCGAAGTCCGCTGCGGGCAC-CTATGTGTTCAACGAACGCAAAATGCTG-GATGCTTCCCAC-GTGGTGGTGTTCTGCGCGAAAAC-CGCGATGGATGACGCCTGGCTG-GAGCGCGTCGTGGATCAGGAA-GAGGCCGATGGCCGTTTCAACACGCCGGAA-GCCAAAGCCGCAAACCATAAGGGCCGCAC-CTACTTCGCCGACATGCACCGCGTG-GATCTGAAAGATGACGACCAGTG-GATGGCGAAGCAGGTTTACCTGAACGTCGG-CAACTTCCTGCTGGGCGTGGGCGCGATGGGT-CTGGACGCGGTACCAATTGAAGGTTTCGAC-GCCGCTATTCTCGACGAAGAGTTT-GGCCTGAAAGAGAAAGGCTTCAC-CAGCCTGGTGGTGGTACCGGTTGGGCAC-CACAGCGTGGAAGATTTCAACGCCAC-GCTGCCGAAATCTCGCCTGCCGCTGAGCAC-GATTGTGACCGAGTGCTAAGGAGTCTTCaga-ga - SEQ ID No: 87 | IDT DNA | bbsl/bbsl<br>Nitroreductase<br>*Enterobacter cloacae* |

TABLE 3

| Plasmid | Description | Antibiotic Resistance | Reference |
|---|---|---|---|
| pUC19 | High copy expression vector (pMB1 ORI) with a lacZα | Amp | Yanisch-Perron, Vieira, & Messing, 1985 |
| pCP20 | Contains FLP recombinase Temperature-sensitive ORI | Amp | Cherepanov & Wackernagel, 1995 |
| pMAK705 | Contains pSOC1 a thermo-sensitive ORI | CatP | Hamilton et al 1989 |
| pJET 1.2 | Ready selection cloning vector | Amp | Agdanaviciute, Zakare-viciene, & Lubys, 2007 (Unpublished) |
| pStA0 | Combinatorial built plasmid level 0 | Amp | G. Taylor & J. Heap (Unpublished) |
| pStA1 | Combinatorial built plasmid level 1 | tetR | G. Taylor & J. Heap (Unpublished) |
| pStA2 | Combinatorial built plasmid level 2 | KanR | G. Taylor & J. Heap (Unpublished) |
| pLS1 | pUC19 with ADH NADH-dependent from *Escherichia coli* (adhE) | Amp | This work |
| pLS2 | pUC19 with SADH NADH-dependent from *Bacillus subtilis* (bdhA) | Amp | This work |
| pLS3 | pUC19 with SADH NADH-dependent from *Klebsiella pneumoniae* (budC) | Amp | This work |
| pLS6 | pUC19 with ADH NADPH-dependent from *clostridium beijerinckii* | Amp | This work |
| pLS10 | Same as pLS6 but with 4 AAs mutated (library) | Amp | This work |
| pLS11 | pUC19 with ADH from *Thermus* sp ATN1 - 6xHis tag on the C-terminus of the TADH | Amp | This work |
| pLS12 | pUC19 with ADH from *Thermus* sp ATN1 | Amp | This work |
| PLS25 | PUC19 with SADH NADH-dependent from *Bacillus subtilis* (bdhA) but with6xHis tag on the C-terminus of bdhA | Amp | This work |
| pLS26 | Same as pLS6 but with 6xHis tag on the C-terminus of CBADH | Amp | This work |
| pLS39 | pMAK705- to knock out sthA | CatP | This work |
| pLS40 | pMAK705- to knock out pntA | CatP | This work |
| pLS46 | pStAO- atoB | Amp | This work |
| pLS47 | pStAO- atoD | Amp | This work |
| PLS48 | pStAO-atoA | Amp | This work |
| PLS49 | pStAO-ADC | Amp | This work |
| PLS50 | pStAO-CBADH_WT | Amp | This work |
| PLS51 | pStAO- CBADH_variant | Amp | This work |
| pLS53 | pStA1AB- atoB with library of pro-moters (Anderson promters) and RBS | tetR | This work |
| PLS54 | pStA1BC- atoD with library of pro-moters (Anderson promters) and RBS | tetR | This work |
| PLS55 | pStA1CD- atoA with library of pro-moters (Anderson promters) and RBS | tetR | This work |
| pLS56 | pStA1DE -ADC with library of pro-moters (Anderson promters) and RBS | tetR | This work |
| pLS57 | pStA1EZ - CBADH_WT with library of promoters (Anderson promters) and RBS | tetR | This work |
| PLS58 | pStA1EZ- CBADH_variant with li-brary of promoters (Anderson promters) and RBS | tetR | This work |
| pLS60 | pStA212- Library of the IPA path-way with CBADH-variant | KanR | This work |
| pLS61 | pStA212- pStA212- Library of the IPA pathway with CBADH-WT | KanR | This work |
| pLS63 | pMAK705- to knock out ldhA | CatP | This work |

DH5α *Escherichia coli* cells were transformed with the plasmid of interest and cultured on LB agar plates. Then single colonies were picked to do 5 mL overnight cultures. Overnight cultures were spun down and the pellets were used to extract the plasmids of interest by using QIAprep Miniprep kit (Qiagen). Plasmids were sequenced by Source BioScience.

Bacterial Strains and Culture Conditions

A list of *Escherichia coli* strains used in the study is shown in Table 4.

TABLE 4

*Escherichia coli* strains used in this project

| Strain | Description | Antibiotic Resistance | Reference |
|---|---|---|---|
| DH5α | F-, φ80dlacZΔM15, Δ(lacZYA-argF)U169, deoR, recA1, endA1, hsdR17(rK–, mK+), phoA, supE44, λ-, thi-1, gyrA96, relA1 | None | Grant et al, 1990 |
| BW25113 | F-, DE(araD-araB)567, lacZ4787(del)::rrnB-3, λ-, rph-1, DE(rhaD-rhaB)568, hsdR514 | None | Datsenko & Wanner, 2000 |
| LS1 | F-, DE(araD-araB)567, lacZ4787(del)::rrnB-3, λ-, rph-1, DE(rhaD-rhaB)568, hsdR514, ΔadhE, ΔldhA | None | This work |
| LS2 | F-, DE(araD-araB)567, lacZ4787(del)::rrnB-3, λ-, rph-1, DE(rhaD-rhaB)568, hsdR514, ΔadhE, ΔldhA | Kan | This work |
| LS5 | F-, DE(araD-araB)567, lacZ4787(del)::rrnB-3, λ-, rph-1, DE(rhaD-rhaB)568, hsdR514, ΔadhE, ΔldhA, ΔsthA, ΔpntA | Kan | This work |
| ΔldhA-JW1375 | F- DE(araD-araB)567, lacZ4787(del)::rrnB-3, λ-, rph-1, DE(rhaD-rhaB)568, hsdR514 | Kan | Baba et al, 2006 |
| ΔadhE-JW1228 | F-, DE(araD-araB)567, lacZ4787(del)::rrnB-3, λ-, rph-1, DE(rhaD-rhaB)568, hsdR514 | Kan | Baba et al, 2006 |

*Escherichia coli* strains were grown in Luria-Bertani broth (LB) at 37° C. with shaking at 250 rpm, or on LB agar plates containing the corresponding antibiotic.

Construction of *Escherichia coli* Selection Strains (LS1 and LS2)

Standard methods using pMAK705 (Hamilton et al 1989) and pCP20 (Cherepanov & Wackernagel, 1995) were used to construct the double mutant strains, triple mutant strains, and the quadruple mutant strain.

Metabolic Complementation

The LS1 mutant strain and the parental BW25113 strain were transformed with the desired plasmid and overnight pre-cultures were grown aerobically in 15 mL Falcon tubes with M9 media (0.4% glucose). These pre-cultures were used to inoculate 10 mL Hungate tubes with M9 medium (0.4% glucose) supplemented with 100 g/mL ampicillin, 1 mM IPTG and with or without the specific substrate of the dehydrogenase under anaerobic conditions at 37° C. Metabolic complementation was assessed by measuring the optical density at 600 nm every two hours during daytime.

Results

EXAMPLE 1—NAD+ REGENERATION ALONE CAN RESCUE FERMENTATIVE GROWTH OF AN ADHE/LDHA MUTANT

Figure 1:
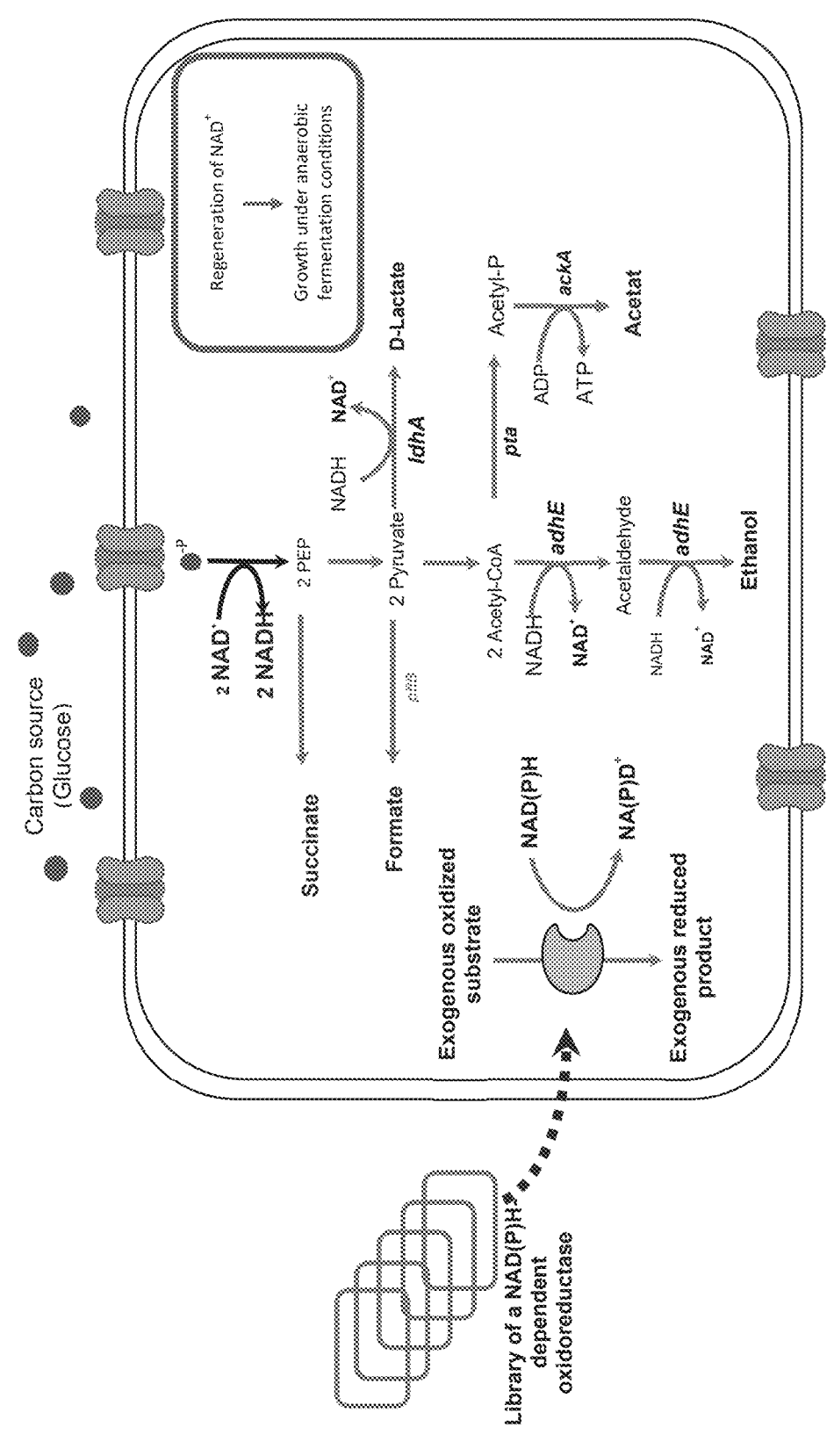
Figure 1:
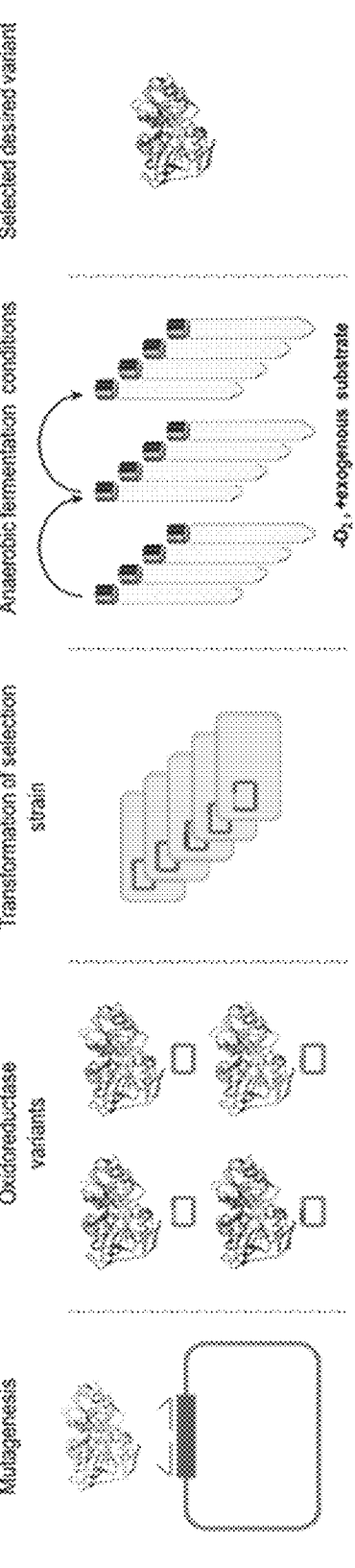
Figure 2:
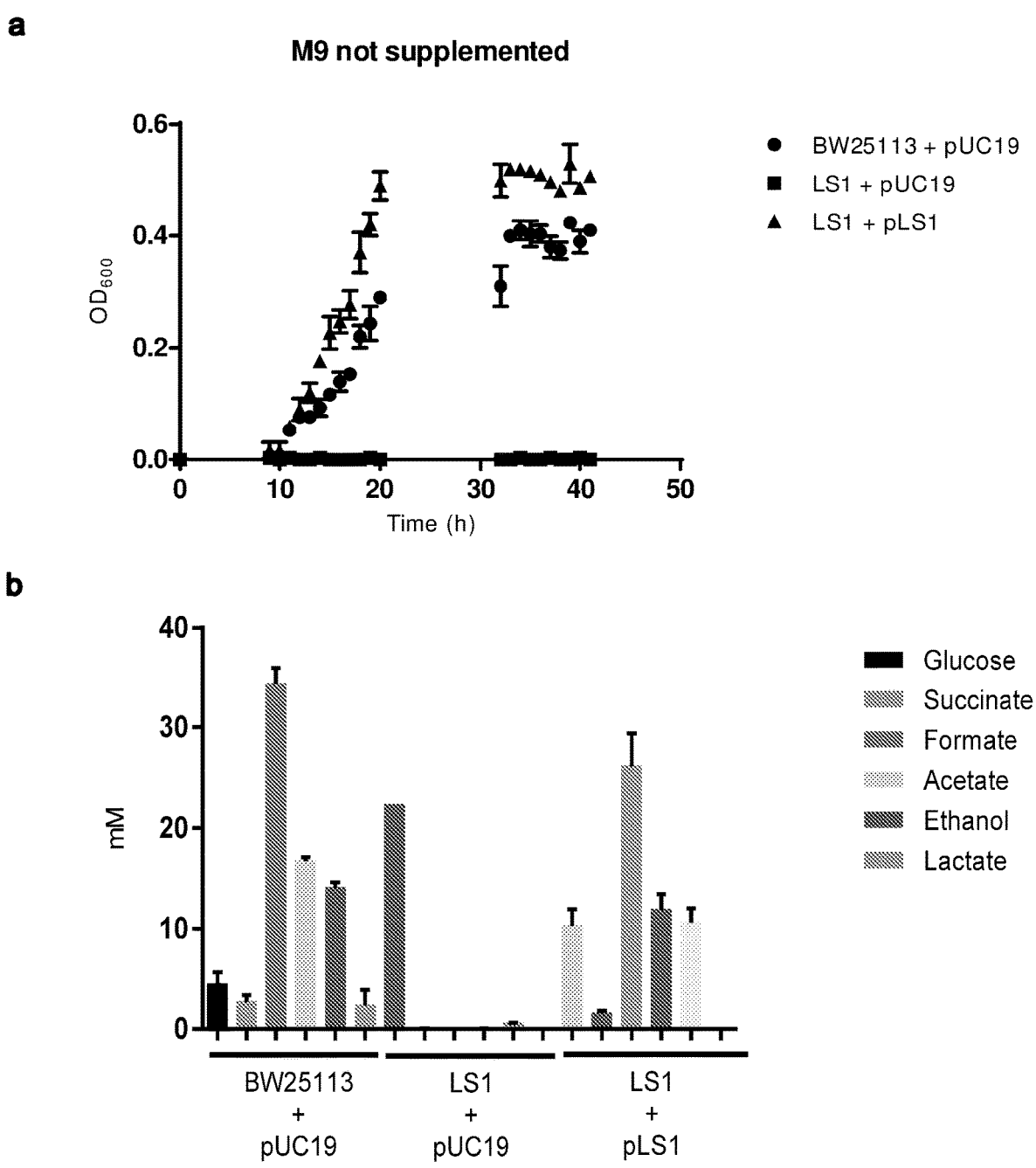

To design a system able to select specific enzyme variants depending on their ability to transfer electrons from NADH to a specific substrate, the inventors constructed an *Escherichia coli* strain, LS1, which is unable to grow under anaerobic conditions due to impaired fermentative pathways. This was achieved by deleting the genes encoding alcohol dehydrogenase (adhE) and lactate dehydrogenase (ldhA), which are essential for ethanol fermentation and lactic acid fermentation, respectively. If only adhE was deleted, cells might adapt to be able to grow. This is due to the fact that cells can in principle grow anaerobically simply by converting glucose to lactate, since the chemical stoichiometry is balanced. Only natural regulation prevents this in cells in which only adhE is mutated. Thus, deletion of ldhA in addition to adhE excludes the possibility of cells adapting to grow by lactate fermentation, in order that cells which are successfully complemented are able to grow exclusively because of the transformed oxidoreductase, and that they won't be able to grow if they are not transformed with an active variant. An article by Chang et al reported an *Escherichia coli* mutant which metabolizes glucose exclusively by means of lactic fermentation (Chang et al, 1999), which is a form of anaerobic fermentation known to occur naturally in other organisms. The growth of strain LS1 under aerobic conditions was unaltered from the wild type, but it was unable to grow anaerobically. Complementation by transformation with pLS1 (containing the endogenous adhE gene) resulted in restoration of ability to grow anaerobically, with cells transformed with this plasmid being able to grow as efficiently as wild-type cells under anaerobic conditions (FIG. 2a). HPLC-RID of the fermentation broth of these cultures confirmed the profile of produced metabolites was similar to that of the parental strain, except for the absence of lactate (FIG. 2b).

Without wishing to be bound to any particular theory, the inventors hypothesized that the main reason fermentative growth was impaired in strain LS1 was the lack of regeneration of oxidized NAD+, necessary for anaerobic glycolysis to continue. Thus, fermentative anaerobic growth recovery would be achievable by transforming cells with a plasmid containing any exogenous NADH-dependent oxidoreductase and culturing them in minimal M9 medium supplemented with the appropriate oxidized substrate for the exogenous enzyme. To confirm this hypothesis, the inventors tested metabolic complementation with several exogenous enzymes. First, strain LS1 cells were transformed with pLS2 and pLS3, both of them containing 2,3-butanediol dehydrogenases from *Bacillus subtilis* (bdhA) and *Klebsiella pneumoniae* (budC), respectively. Both enzymes are able to catalyse the reduction of acetoin coupled to the oxidation of NADH. When transformed cells were grown anaerobically, growth recovery was achieved if the medium was supplemented with acetoin. Interestingly, anaerobic growth recovery was also observed when mutant cells transformed with a control plasmid not containing any exogenous enzyme were supplemented with acetoin. However, growth rate of cells was much slower than when they were transformed with pLS2 and pLS3. These results suggest that the *Escherichia coli* genome encodes an endogenous enzyme able to catalyse the reduction of acetoin coupled to the oxidation of NADH. The longer time needed for growth recovery compared to the cells transformed with the exogenous enzymes indicate that the endogenous enzyme has a low activity towards acetoin, or alternatively its expression level is low. A potential candidate for this enzyme is YohF, a putative oxidoreductase which has been predicted to be an acetoin reductase based on sequence similarity with confirmed acetoin reductases (Reed et al, 2003).

Figure 3:
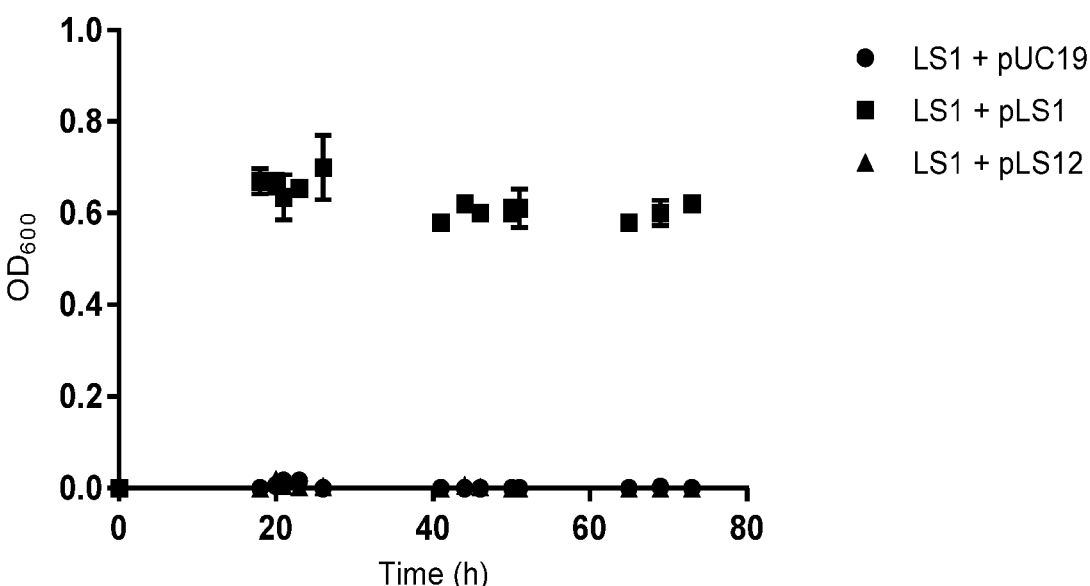
Figure 3:
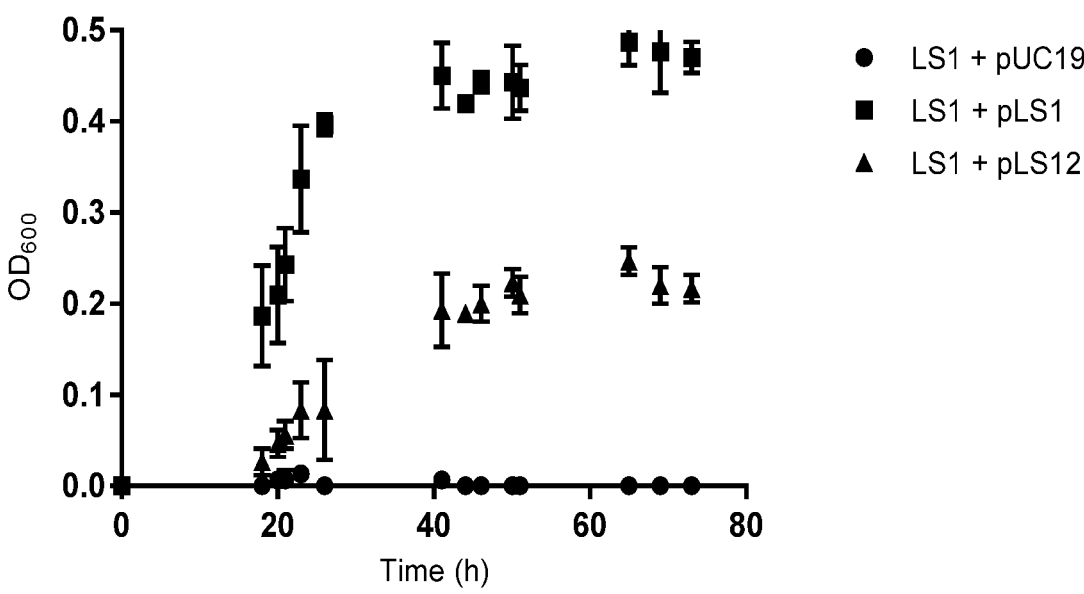
Figure 3:
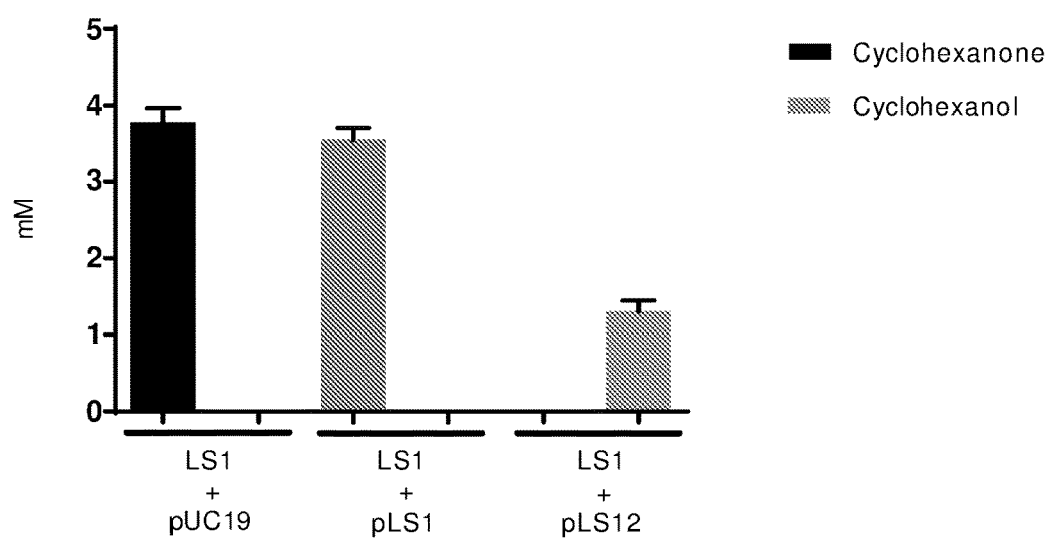
Figure 3:
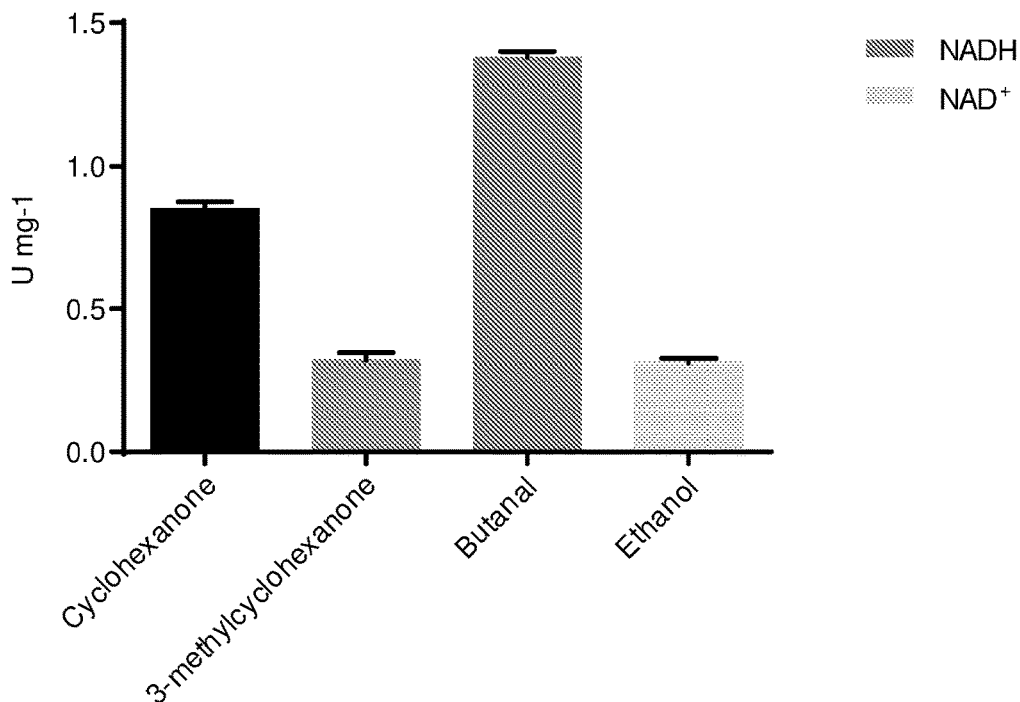

To completely rule out that growth recovery was mostly due to the activity of an endogenous enzyme, the inventors tested another exogenous enzyme, alcohol dehydrogenase from *Thermus* sp. ATN1 (TADH), which is able to act on a broad range of substrates (Höllrigl et al, 2008). The inventors chose two substrates towards which no endogenous *Escherichia coli* enzyme was described to have any activity: cyclohexanone and 3-methylcyclohexanone. Cells transformed with pLS12 (containing TADH) were able to grow anaerobically when media was supplemented with either of the two substrates, but no growth recovery was observed when cells were transformed with a control plasmid (FIG. 3*a*). Enzymatic activity assays with raw cell lysate obtained from the cultures showed that the enzymes were properly expressed and able to reduce both cyclohexanone and 3-methylcyclohexanone, with the activity towards cyclohexanone being 2.5 times greater than towards 3-methylcyclohexanone (FIG. 3*c*). The lower activity with the latter substrate, together with its higher toxicity, explains why cultures supplemented with 3-methylcyclohexanone reach a lower maximum cell density than when supplemented with cyclohexanone. Enzymatic activity towards each substrate was confirmed by assays performed with purified enzyme. Moreover, while HPLC-RID confirmed that neither ethanol nor lactate were produced, gas chromatography revealed that cultures transformed with pLS12 consumed all of the provided cyclohexanone/3-methylcyclohexanone, and converted it into the corresponding alcohol (FIG. 3*b*). These findings support that growth recovery was due to regeneration of oxidized NAD$^+$ by the activity of the exogenous enzyme. A stoichiometric conversion of the substrates into the alcohols was not detected; this is probably caused by the volatile nature of both substrates and products which facilitates losses due to evaporation.

EXAMPLE 2—EVOLUTION OF A NOVEL NADH-DEPENDENT ACETONE REDUCTASE BY SELECTION FOR NAD$^+$ REGENERATION

CBADH is an oxidoreductase able to oxidize isopropanol and reduce acetone characterized by its very high preference for NADP(H) over NAD(H) (Korkhin et al, 1998). In order to test the potential of the described system as a selection tool, the inventors decided to attempt to obtain a variant of CBADH with reversed cofactor specificity, based on the rationale that such a variant would allow for a more efficient growth recovery.

They first tested if wild-type CBADH was able to achieve metabolic complementation. When LS1 strain (ΔadhE ΔldhA double mutant) cells transformed with pLS6, containing the wild type enzyme, were cultured anaerobically in media supplemented with acetone, growth recovery was only observed after 55 hours, a much longer period than LS1 cells transformed with NAD(H)-dependent enzymes. The inventors hypothesized that the very slow metabolic complementation with wild type CBADH might have been due to the activity of a transhydrogenase, which would use the accumulated pool of reduced NADH to reduce NADP$^+$, generating NAD$^+$ and NADPH. The genome of *Escherichia coli* contains two transhydrogenase genes: sthA and pntA. The inventors decided to test the effect of knocking out both genes.

The generation of the library of variants of CBADH took the available structural information as the starting point. Korkhin and collaborators (Korkhin et al, 1998) solved the crystal structure of CBADH and identified a set of 4 amino acid residues (G198, S199, R200 and Y218) potentially critical for the specificity of the enzyme towards NADP(H). All 4 residues made contacts with the 2'-phosphate oxygens of NADP(H) and were conserved in other NADP(H)-dependent alcohol dehydrogenases. The inventors made and tested the specific variant described in Korkhin et al, but found that it did not work. Thus, the inventors decided to generate a library of CBADH variants by using a standard PCR-based method to perform saturation mutagenesis of the codons corresponding to these 4 amino acid residues.

LS1 strain cells transformed with three independently-generated libraries and grown anaerobically in media supplemented with acetone required only 24 hours on average to reach exponential phase of growth, a much shorter period than the required for cells transformed with the wild type CBADH. Clones were was isolated from the three anaerobic cultures and plasmid DNA was prepared, resulting in pLS10_1, pLS10_2 and pLS10_3, respectively. Transforming LS1 strain cells with pLS10_1, pLS10_2 and pLS10_3 allowed growth recovery under anaerobic conditions in media supplemented with acetone. Furthermore, GC analysis of the fermentation broth confirmed the presence of isopropanol in cultures transformed with pLS10_1 at much higher levels than in those transformed with pLS6, which correlated with the absence of acetone.

Sequencing of pLS10_1, pLS10_2 and pLS10_3 revealed that all of them encoded the same CBADH variant, which contained 8 point mutations in the DNA sequence resulting in 3 amino acid residue substitutions at the protein level: G198D, S199Y and Y218P. Enzymatic activity assays with purified enzyme showed a 4.6-fold increase in activity for the reduction of acetone to isopropanol with NADH as the cofactor when compared to the wild type, and 10-fold increase for the oxidation of isopropanol to acetone with NAD$^+$ as the cofactor. Interestingly, the new variant showed no significant activity for both the reduction and oxidation reactions when NADP(H) was provided as the cofactor. Surprisingly, even though Korkhin et al predicted an R200G mutation to be one of the substitutions most likely to have the effect of cofactor specificity reversal, this residue remained unchanged in our NAD(H)-dependent variant. Moreover, none of the substitutions found for the other 3 residues matched those suggested in the Korkhin et al study. However, the G198D mutation has been found to switch the cofactor specificity of *Thermoanaerobacter brockii* and *Clostridium autoethanogenum* alcohol dehydrogenases from NADP(H) to NAD(H) (Maddock, Patrick & Gerth, 2015). Indeed, structure-based alignment of several NADP (H)-dependent and NAD(H)-dependent dehydrogenases revealed that the residue at position 198 is always acidic in NAD(H)-dependent dehydrogenases. In the same study, it was shown that position 218 is frequently an alanine, serine or proline in NAD(H)-dependent dehydrogenases.

Interestingly, the Cofactory server for identification of cofactor specificity of Rossmann folds based on their amino acid sequence (Geertz-Hansen et al, 2014) was not able to determine if the wild type enzyme would bind preferentially NAD(H) or NADP(H), but it predicted correctly that our NAD(H)-dependent variant had a preference for NAD(H). On the other hand, CSR-SALAD, a recently-developed tool to predict mutations to reverse nicotinamide cofactor specificity reversal (Cahn et al, 2017), correctly identified residues 198, 199 and 218 as recommended targets to attempt cofactor specificity reversal. However, none of the suggested mutations for positions 199 and 218 matched those found in our variant; only for position 198 the recommendations included a substitution for an Asp residue.

In order to try to understand why these mutations led to cofactor specificity reversal, the inventors generated a structural model of the mutated protein by using the structure of the wild type enzyme as the template with the SWISS-MODEL server. Comparison of the wild type structure with the model of the mutant enzyme revealed some information about the structural basis for the cofactor specificity reversal. The substitution of G198 by an aspartate residue placed a negatively charged sidechain in close proximity of the 2' phosphate group of NADPH, which very likely contributes to the inability of the mutant enzyme to accept NADP(H) as the cofactor. Furthermore, the small side chain of S199 is in a position where it does not pose any impediment to the binding of NADP(H), and possibly could form a hydrogen bond with its 2' phosphate group. In the mutant enzyme, it is replaced by a tyrosine residue, with a much bulkier sidechain which is not predicted to be placed in a position where it could form a hydrogen bond with the 2' phosphate.

Finally, the reason why the Y218P substitution contributed to cofactor specificity reversal remains unclear, since this residue is not located in the vicinity of the 2' phosphate, but instead contacts the adenine ring moiety.

FIG. 15 summarises the workflow of producing the variant CBADH and shows the crystal structure of pLS10 3 bound to NADH, obtaining insight into the structural basis of cofactor preference reversal.

A summary of the NMR spectra confirming the formation of isopropanol both when transforming with the library or pLS10 1, pLS10_2, pLS10 3 can be seen in Table 5, and Table 6 shows that pLS10_1, pLS10_2, pLS10_3 comprising the variant gained activity with NADH and activity with NADPH had been lost (Table 6).

| | | | | δ of characteristic signal of substrate (ppm) | δ of characteristic signal of product (ppm) | | | | | | | |
|---|---|---|---|---|---|---|---|---|---|---|---|---|
| Transformed plasmid/ library | Encoded enzymes(s) | Exogenous substrate | Resulting product | | | Substrate concentration | Product concentration | Ethanol concentration | Lactate concentration | Succinate concentration | Acetate concentration | Formate concentration |
| pLS1 | adhE | — | — | — | — | — | — | 13.8 | 0 | 5.2 | 12.1 | 20.7 |
| pLS2 | bdhA | acetoin | 2,3-butanediol | 1.38 (d, 3) | 1.15 (d, 6) | 0 | 8.4 | 0 | 0 | 0.5 | 6.7 | 3.7 |
| pLS3 | budC | acetoin | 2,3-butanediol | 1.38 (d, 3) | 1.15 (d, 6) | 0.2 | 8.3 | 0 | 0 | 0.7 | 7.9 | 5 |
| pLS6 | CBADH | acetoin | iso-propanol | 2.24 (s, 6) | 1.18 (d, 6) | 0.1 | 10.8 | 0 | 0 | 1.1 | 8.1 | 5.8 |
| pLS10_3 | CBADH-s | acetoin | iso-propanol | 2.24 (s, 6) | 1.18 (d, 6) | 0.5 | 12.7 | 0 | 0 | 1.1 | 13 | 9.9 |
| pLS130 | MsIRED | 2-methyl-1-pyrroline | 2-methyl-pyrrolidine | 2.43 (s, 3) | 1.38 (d, 3) | 5.5 | 6.6 | 0 | 0 | 1.2 | 4.3 | 2.1 |
| pLS131 | MsIRED-c | 2-methyl-1-pyrroline | 2-methyl-pyrrolidine | 2.43 (s, 3) | 1.38 (d, 3) | 3.45 | 9.2 | 0 | 0 | 1.7 | 10.7 | 7.9 |
| pLS133s1 | MsIRED-s | 2-methyl-1-pyrroline | 2-methyl-pyrrolidine | 2.43 (s, 3) | 1.38 (d, 3) | 0.8 | 13.4 | 0 | 0 | 2 | 15.9 | 12.8 |
| pLS168 | EntNFSB | 2-nitrobenzoic acid | ? | 8.10 (d, 1) | ?2.38 (s, ?) | 14.1 | ? | 0 | 0 | 0 | 0.7 | 0.4 |
| pLS168 | EntNFSB | 4-nitrobenzoic alcohol | ? | 8.27 (d, 2) | ?2.38 (s, ?), 8.01 (d, ?) | 8.28 | ? | 0 | 0 | 0 | 0.8 | 0.4 |
| pLS169s1 | EntNFSB-s1 | 2-nitrobenzoic acid | ? | 8.10 (d, 1) | ?2.38 (s, ?) | 12.4 | ? | 0 | 0 | 0.3 | 4.4 | 2.9 |
| pLS169s2 | EntNFSB-s2 | 4-nitrobenzylic alcohol | ? | 8.27 (d, 2) | ?2.38 (s, ?), Multiple signals between 6.5 and 8 ppm | 0 | ? | 0 | 0 | 1 | 13.2 | 7.9 |

1H NMR analysis of fermentation broth of anaerobic cultures

TABLE 6

Kinetics of evolved and parental enzymes

| Enzyme | Variable substrate | Cofactor | Substrate Km | kcat | kcat/Km (min−1 mM−1) | Ki (substrate) | Enzyme concentration |
|---|---|---|---|---|---|---|---|
| CBADH | Isopropanol | NADP+ (1 mM) | 5.80 mM | 1185.6 min−1 | 204.6 | — | 110 nM |
| CBADH | Isopropanol | NAD+ | ND | ND | ND | — | 110 nM |
| CBADH-s | Isopropanol | NADP+ | ND | ND | ND | — | 110 nM |
| CBADH-s | Isopropanol | NAD+ (10 mM) | 17.49 mM | 333 min−1 | 19 | — | 110 nM |
| MsIRED | 2-methylpyrroline | NADPH (0.25 mM) | 3.56 mM | 89.8 min−1 | 25.2 | 18.05 mM | 1.2 uM |
| MsIRED | 2-methylpyrroline | NADH | ND | ND | ND | — | 1.2 uM |
| MsIRED-c | 2-methylpyrroline | NADH (0.25 mM) | 41.79 mM | 119.6 min−1 | 2.9 | 4.21 mM | 1.2675 uM |
| MsIRED-s | 2-methylpyrroline | NADH (0.25 mM) | 19.57 mM | 78.1 min−1 | 4 | 11.42 mM | 1.25 uM |
| EntNFSB | 2-nitrobenzoic acid | NADH | N.D. | ? N.D. | N.D. | N.D. | 1 uM |
| EntNFSB-s1 | 2-nitrobenzoic acid | NADH | 4.054 | 1.17 min −1 | 0.29 mM | | 1 uM |

TABLE 6-continued

| | | | Kinetics of evolved and parental enzymes | | | | |
| Enzyme | Variable substrate | Cofactor | Substrate Km | kcat | kcat/Km (min−1 mM−1) | Ki (substrate) | Enzyme concentration |
| --- | --- | --- | --- | --- | --- | --- | --- |
| EntNFSB | 4-nitrobenzyl alcohol | NADH | 9.52 mM | 8.76 min −1 | 0.92 mM | | 1 uM |
| EntNFSB-s2 | 4-nitrobenzyl alcohol | NADH | 1.111 mM | 4.35 min −1 | 3.92 mM | | 1 uM |

EXAMPLE 3—INTEGRATION OF NADH-DEPENDENT CBADH INTO AN ISOPROPANOL PRODUCTION PATHWAY

Figure 5:
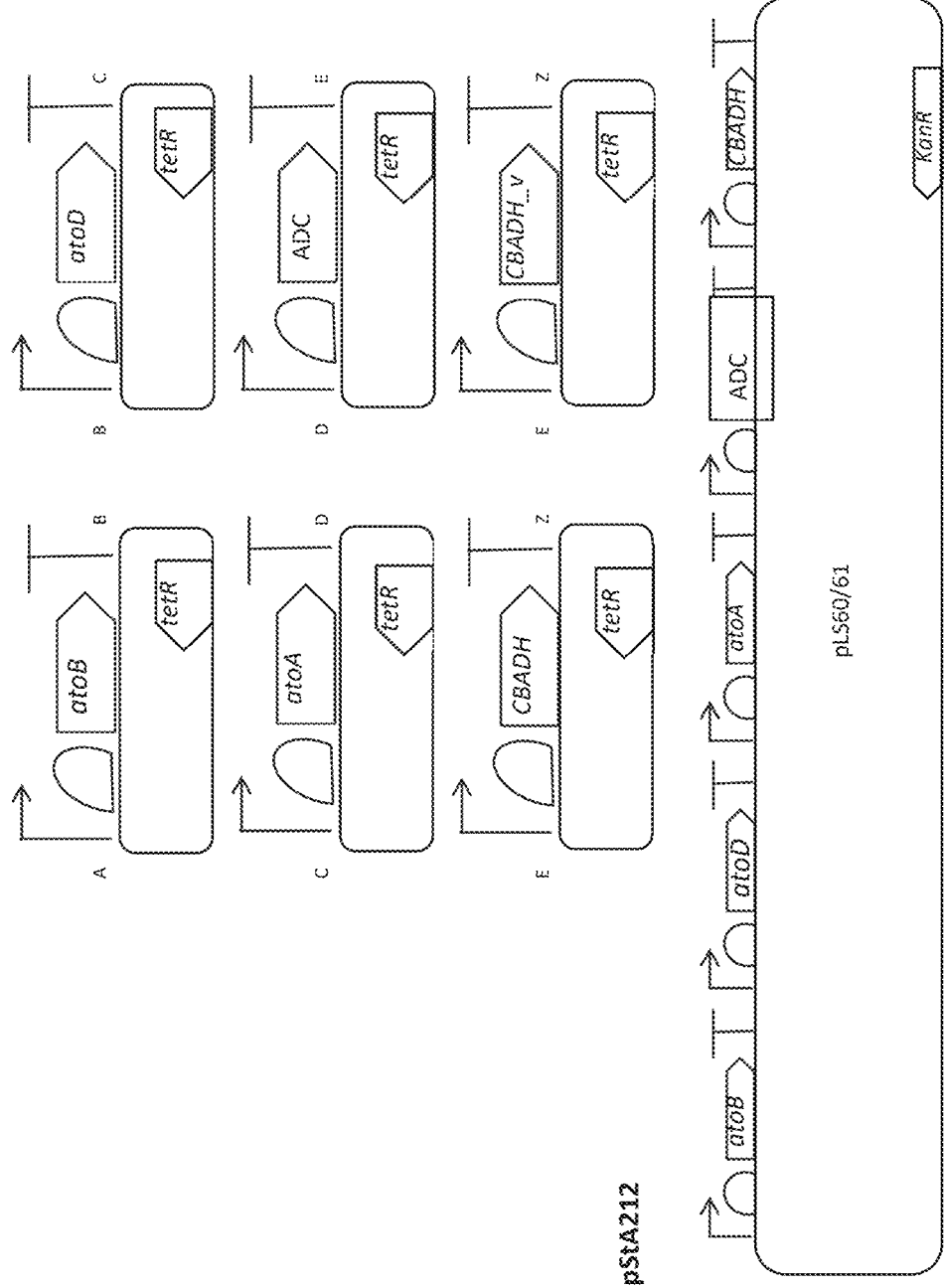
FIG. 5 shows a DNA sequence combinatorially assembled to express an isopropanol pathway including an integrated NAD(H)-dependent variant of CBADH.
Figure 5:
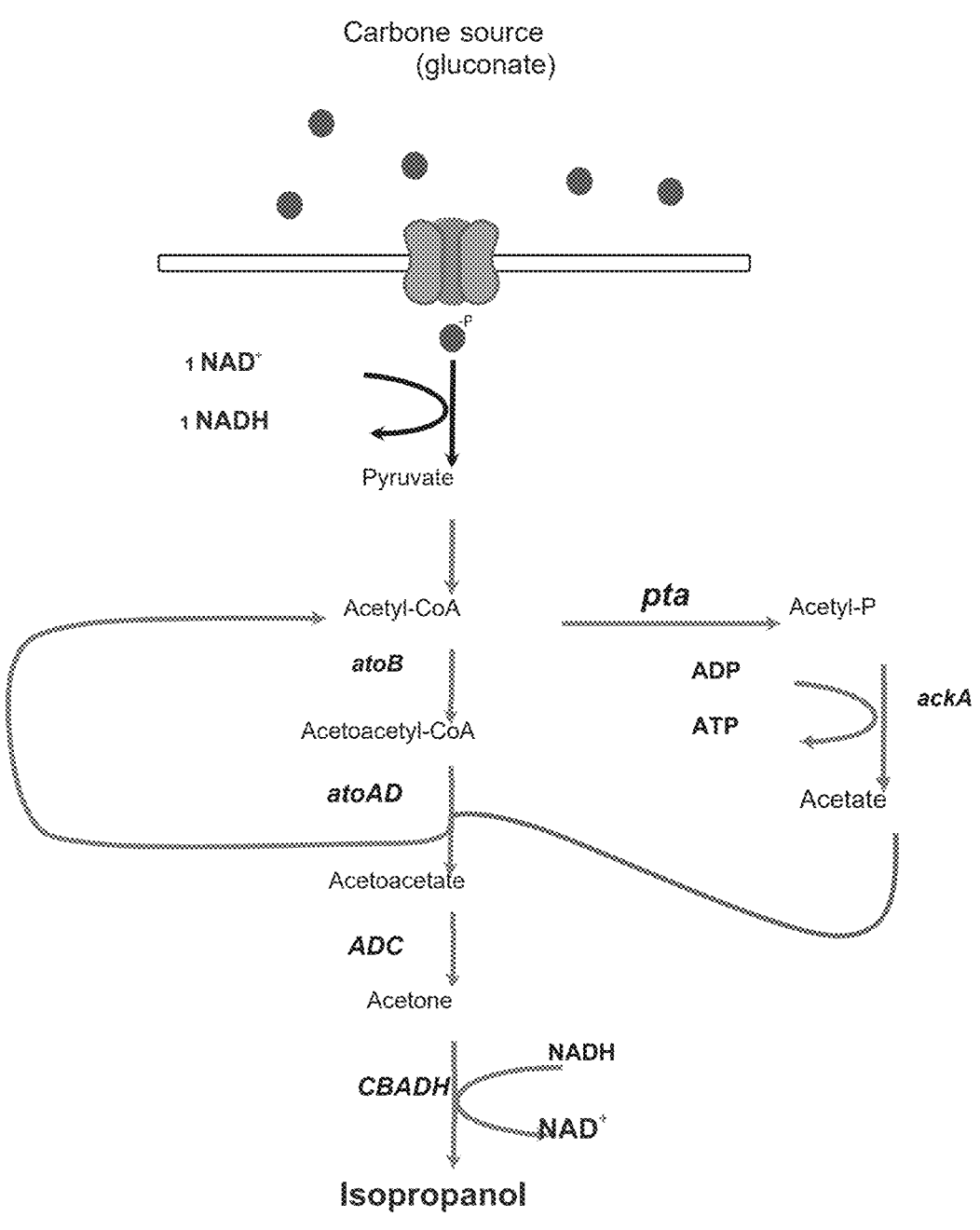
Figure 6:
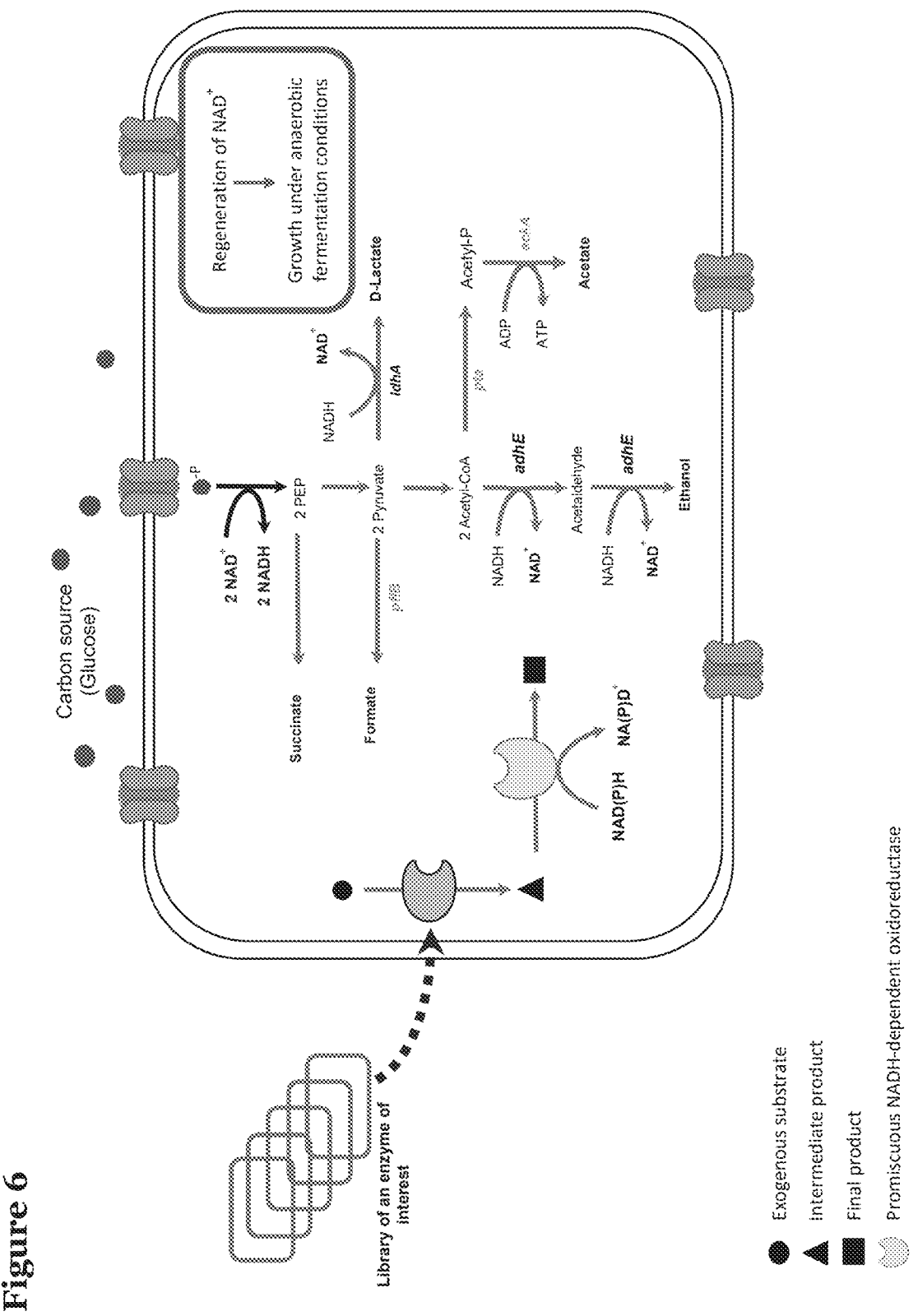
FIG. 6 is a schematic representation of one embodiment of the selection system of the invention wherein the polypeptide of interest is an enzyme that catalyses the conversion of an exogenous substrate into an intermediate product that is utilised as a substrate for a promiscuous NADH-dependent oxidoreductase.
Figure 7:
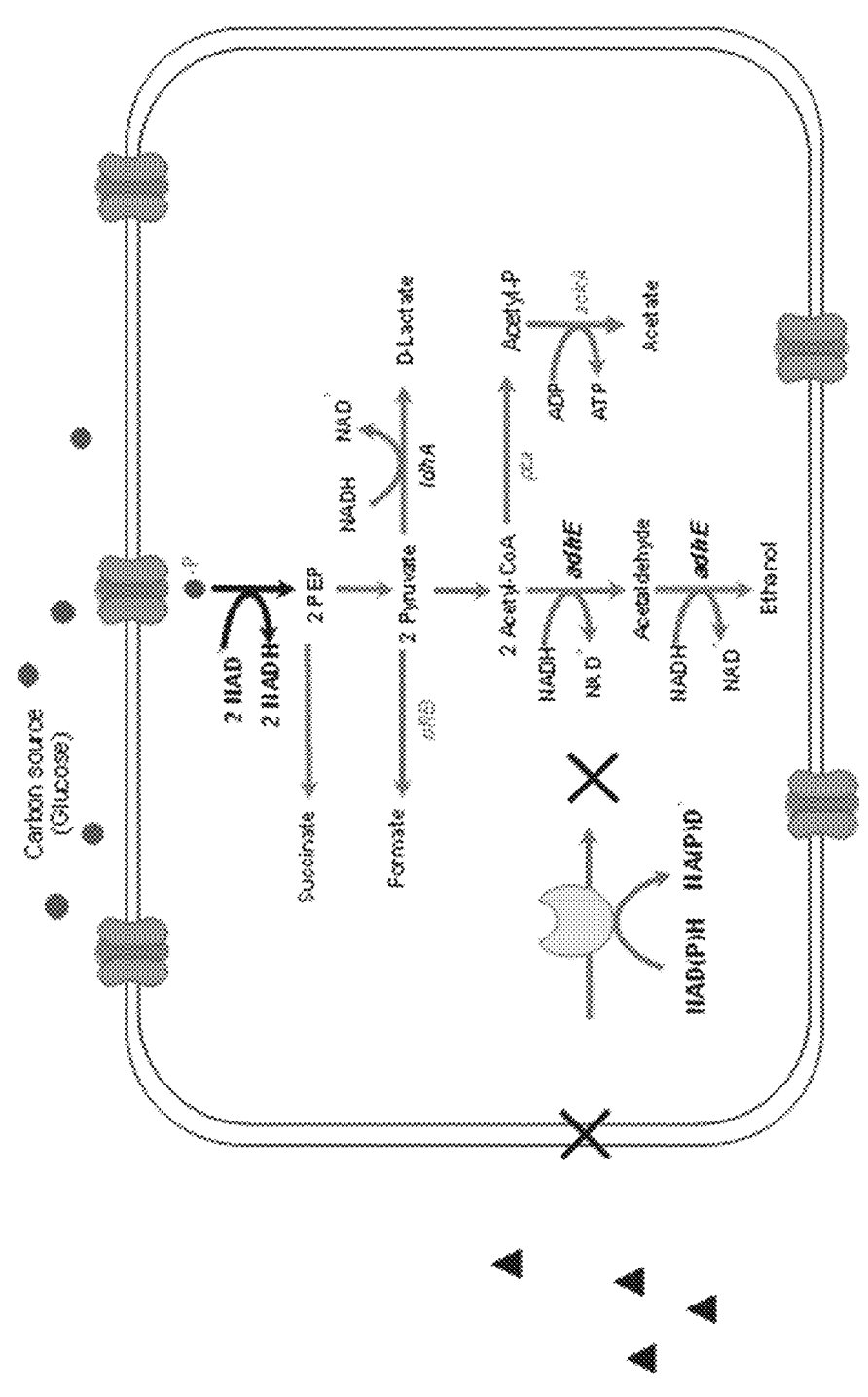
FIG. 7 is a schematic representation of one embodiment of the selection system of the invention wherein the polypeptide of interest is a membrane transporter.
Figure 7:
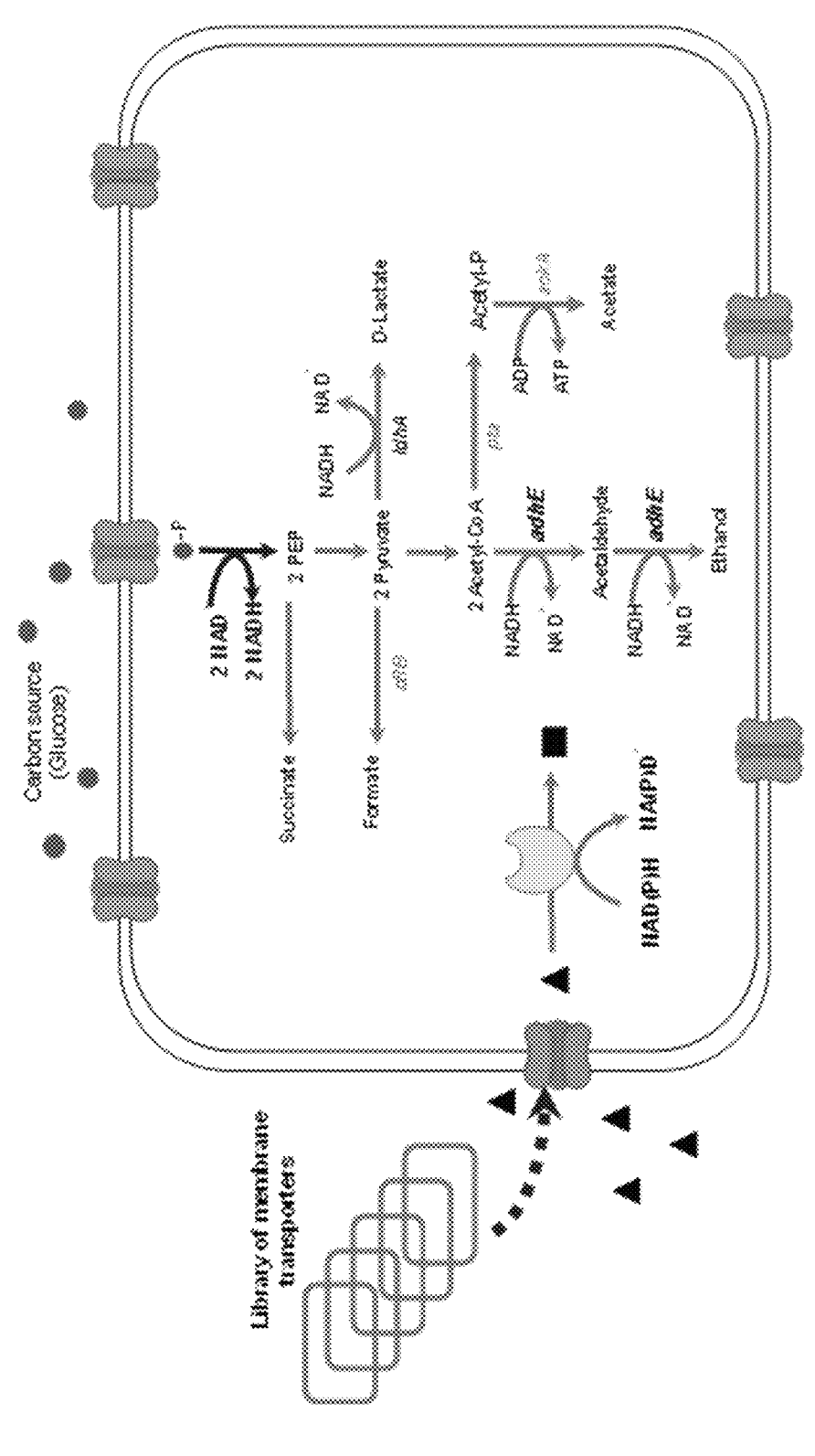
Figure 7:
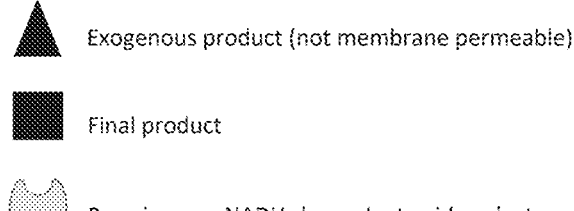

Hanai et al engineered a synthetic pathway for isopropanol production in *Escherichia coli* (Hanai, Atsumi & Liao, 2007) by expressing five genes from a combination of organisms in *Escherichia coli: Escherichia coli* acetyl-CoA acetyltransferase (atoB), *Clostridium acetobutylicum* acetoacetate decarboxylase (adc), *Escherichia coli* acetyl-CoA:acetoacetyl-CoA transferase (atoAD) and CBADH. The pathway is summarized in FIG. 5. The obtained yield from this recombinant strain cultivated anaerobically was 43.5% (mol/mol), exceeding the yields obtained even from native producers.

The inventors hypothesized that the yield could be increased by culturing cells under anaerobic fermentation conditions and substituting the wild type CBADH previously employed by the NAD(H)-dependent variant identified with our selection method. Under anaerobic fermentation conditions, reduced NADH cannot be used to reduce an external electron acceptor such as molecular oxygen, so a large fraction of the NADH generated by glycolysis would be used by the CBADH variant to produce isopropanol, and the yield of isopropanol obtained could approach the theoretical maximum.

EXAMPLE 4—SELECTION STRAIN SPECIFIC FOR NADH-DEPENDENT OXIDOREDUCTASES

As LS1 (ΔadhE-ΔldhA double mutant) was able to grow when transformed with an NADPH-dependent oxidoreductase (wild type CBADH), the inventors generated two triple mutants where, in addition to adhE and ldhA, one transhydrogenase gene was deleted in each. Transhydrogenases catalyse the direct transfer of electrons from NADH to NADP$^+$ and from NADPH to NAD$^+$, in the following reaction: NADH+NADP$^+$=NAD$^+$+NADPH. Without wishing to be bound to any particularly theory, the inventors hypothesized the activity of these transhydrogenases is what makes the system able to restore anaerobic growth when transformed with enzymes that generate NADP+. Two triple mutants, where one transhydrogenase gene was knocked out in addition to adhE and ldhA, were generated, since there are 2 transhydrogenase genes in *E. coli:* sthA (soluble transhydrogenase)
pntA (transmembrane transhydrogenase).

When metabolic complementation was attempted with an NADPH dependent alcohol dehydrogenase (wild type CBADH) with any of the triple mutants, cells were still able to grow anaerobically.

Since in the triple mutants the non-deleted transhydrogenase could still be supporting anaerobic growth under anaerobic fermentation conditions when complemented with an NADPH-dependent oxidoreductase by generating oxidized NAD, the inventors generated a quadruple mutant where adhE, ldhA, sthA and pntA genes were deleted (LS5 strain, FIG. 11).

This strain displays the following features (FIG. 12):

It is unable to grow anaerobically.
When transformed with plasmid containing adhE, anaerobic growth is restored.
When transformed with plasmid containing NADPH-dependent oxidoreductase (pLS6, containing wild type CBADH), anaerobic growth is not restored, independently of whether the media is supplemented with acetone or not.
When transformed with plasmid containing an NADH-dependent variant of CBADH (pLS10_3), anaerobic growth is restored if the media is supplemented with acetone (the substrate of the enzyme).

This shows that the reason the double mutant is able to grow anaerobically when transformed with an enzyme that generates oxidized NADP, is the activity of transhydrogenases that use NADP to generate NAD. The LS5 strain can thus be used as a more strict selection system: to select strictly for enzymes which regenerate oxidized NAD, and not either NAD or NADP, as is the case when using LS1 strain.

The inventors tested the suitability of four *Escherichia coli* mutant strains for use in the selection method, and these strains were:

LS1=AL (ΔadhE ΔldhA): the main strain we use in the selection system, with metabolic defects that make them unable to grow under anaerobic fermentation conditions due to their inability to regenerate oxidized NAD+.
LS2=AL (ΔadhE:Kan ΔldhA): metabolic defects that make them unable to grow under anaerobic fermentation conditions due to their inability to regenerate oxidized NAD+.
LS3=ALS (ΔadhE ΔldhA ΔsthA): triple mutant with sthA transhydrogenase mutated.
LS4=ALP (ΔadhE ΔldhA ΔpntB): triple mutant with pntB transhydrogenase mutated.
LS5=ALPS (ΔadhE ΔldhA ΔpntB ΔsthA): quadruple mutant with both transhydrogenases mutated.

The inventors demonstrated that all four strains tested were suitable for the selection system described (FIGS. 13 and 14). However, the ALPS strain cannot grow under anaerobic fermentation conditions when transformed with a gene encoding enzymes that cause the generation of oxidized NADP+. All three of the other strains can be complemented with an NADP+ regenerating enzyme, although it takes a longer time to observe anaerobic growth. Without wishing to be bound to any particular theory, the inventors conclude that the metabolic complementation observed in AL, ALS and ALP strains with NADP+ dependent enzymes is mediated by transhydrogenases (both sthA and pntB are suitable for it), which use the oxidized NADP+ to generate oxidized NAD+. In the ALPS strain, this is not possible, since both transhydrogenases are knocked out (pLS6 encodes wild type CBADH, which can only use NADPH; pLS10_3 encodes CBADH-variant, which can only use NADH).

The selection system was validated using these strains, and is summarised as follows:

Metabolic complementation was achieved when cells where transformed with the following:

Native *E. coli* adhE=pLS1 (FIG. 14*c*)

budC=pLS3 (acetoin reductase from *Klebsiella pneumoniae*), and acetoin was added to the culture (FIG. 14*d*)

bdhA=pLS2 (acetoin reductase from *Bacillus subtilis*), and acetoin was added to the culture (FIG. 14*d*)

TADH=pLS12 (alcohol dehydrogenase from *Thermus* sp. ATN1), and cyclohexanone was added to the culture (FIG. 14*f*)

TADH, and 3-methylcyclohexanone was added to the culture (FIG. 14*f*)

In all cases, formation of the expected reduced products was confirmed with NMR (FIGS. 14*e* and 14*g*, Table 5).

EXAMPLE 5—GENERATION OF IMINE REDUCTASE VARIANTS

Imine reductases (IREDs) are able to catalyse the reduction of imines and reductive amination of ketones with high enantiospecificity and regiospecificity. No naturally occurring IRED that is able to utilise NADH for catalyzing their reaction is known.

Two previous studies have obtained mutant IREDs that display activity with NADH, by means of screening methods:

1) A variant of IRED from *Streptomyces* GF3587 (IR-Sgf3587), with a K40A substitution (A NADH-accepting imine reductase variant: Immobilization and cofactor regeneration by oxidative deamination, Journal of Biotechnology, vol 230, 20 Jul. 2016, pages 11-18).

2) Several variants of *Myxococcus stipitatus* IRED (MsIRED) (SEQ ID No:34), with the best one containing 5 residue substitutions, reached after several rounds of mutagenesis and screening (Switching the Cofactor Specificity of an Imine Reductase, CHEMCATCHEM, Vol 10, issue 1, pages 183-187).

Figure 4A:
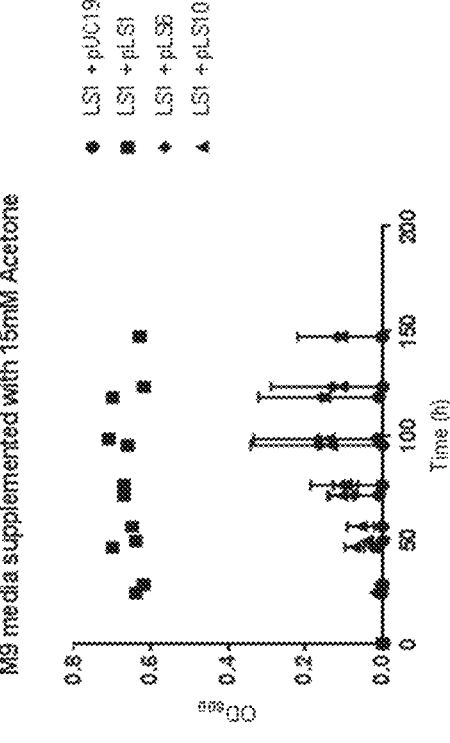
Figure 4A:
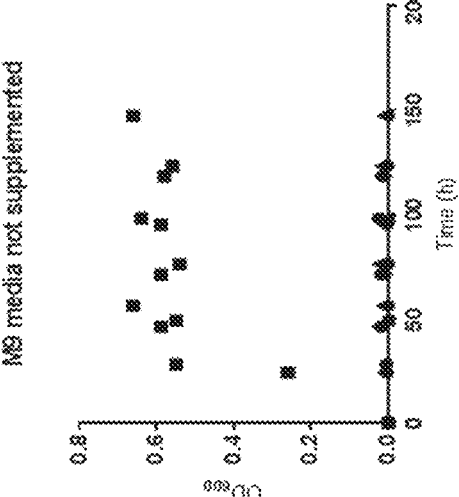
Figure 4B:
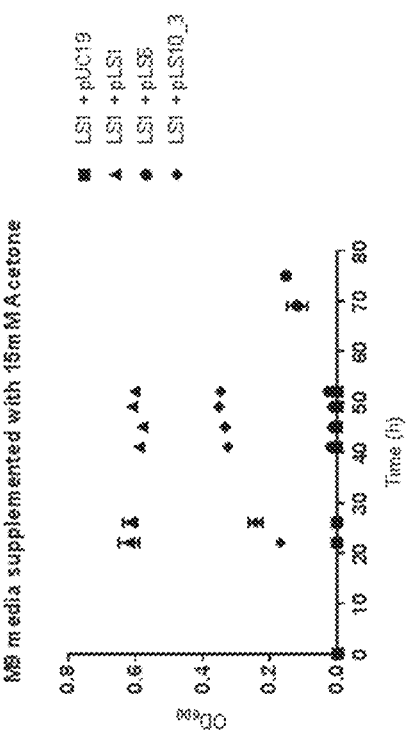
Figure 4B:
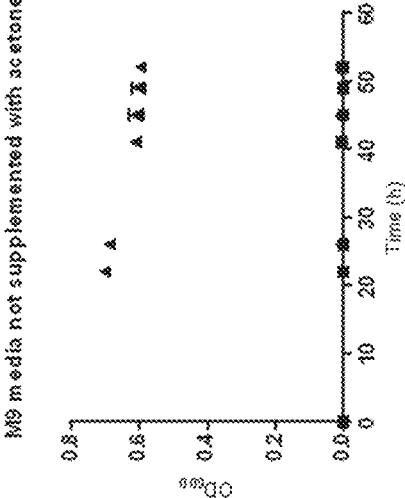
Figure 4C:
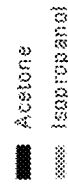
Figure 4C:
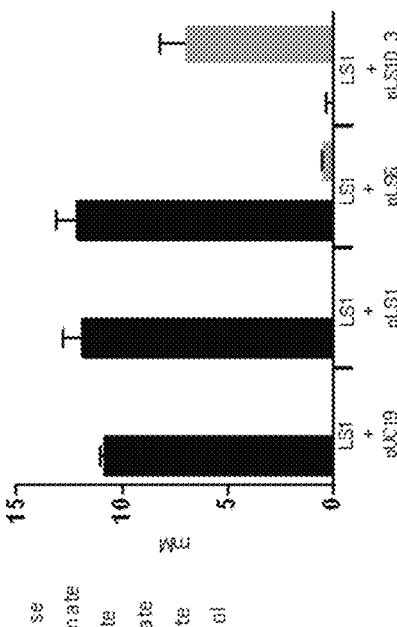
Figure 4C:
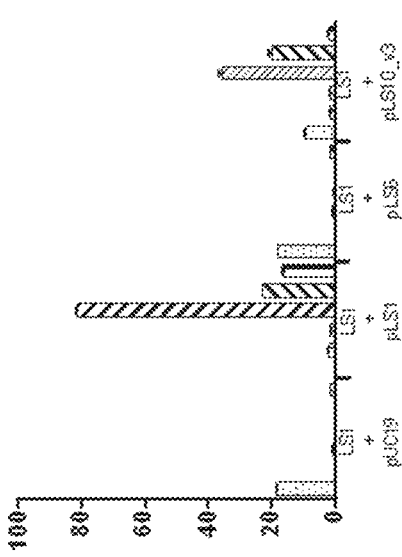
Figure 4D:
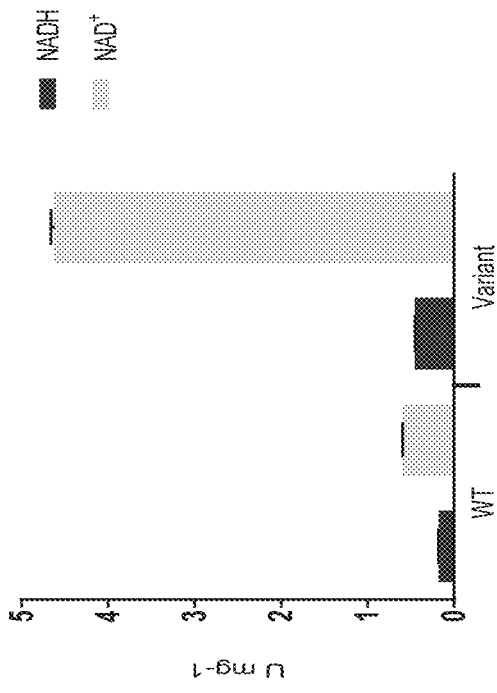
Figure 4D:
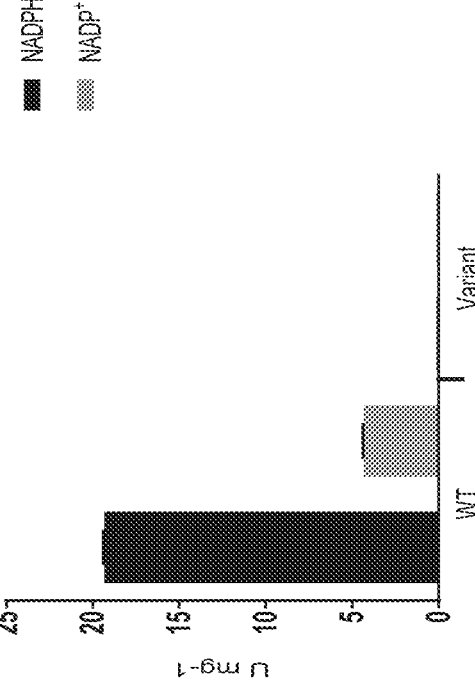

The inventors generated a library of MsIRED by saturation mutagenesis of residues 32, 33, 34 and 37 (FIG. 4*a*). AL cells were transformed with the library and grown anaerobically in media supplemented with 2-methylpyrroline (also known as 2-methyl-1-pyrroline), which contains an imine group. Growth was observed after 55 hours.

Plasmid DNA was isolated from individual colonies and sequenced, revealing all of the selected variants had the same sequence (MsIRED-s=pLS133_1) (SEQ ID No: 35), containing the following residue substitutions with respect to the wild-type: N32E, R33V, T34R and K37R.

This is a different variant than any of the obtained in previous studies and cells transformed with MsIRED-s were able to grow anaerobically in media supplemented with 2-methylpyrroline more efficiently than when transformed with the best variant identified in any previous studies (FIG. 16*b*).

NMR was performed to confirm the presence in the fermentation broth of 2-methylpyrrolidine, the reduced product which contains a secondary amine (Table 5).

Activity assays with MsIRED-s revealed a NADH-dependent reductase activity towards 2-methylpyrroline, whereas no activity was detected with NADPH (FIG. 16*c*, Table 6).

Advantageously, the kinetic parameters of MsIRED-s were better than those of the best previously identified variant, and it displayed lower substrate inhibition (FIG. 16*c*, Table 6).

EXAMPLE 6—SELECTION OF NITROREDUCTASE VARIANTS WITH ALTERED SUBSTRATE SPECIFICITY nsfB nitroreductase from *Enterobacter cloacae* (EntNFSB) (SEQ ID No: 37) is able to catalyze the reduction of several compounds with nitro groups with NADH, including 4-nitrobenzoic acid (4-NBA). The inventors sought to obtain variants with altered substrate specificity, designed to act optimally on 2-nitrobenzoic acid (2-NBA) and 4-nitrobenzyl alcohol.

A crystal structure of EntNFSB bound to 4-NBA is available. Based on it, the inventors generated a library by saturating residues 40, 41, 68 and 124.

AL cells transformed with the library were cultured anaerobically in media supplemented with 2-NBA or 4-nitrobenzyl alcohol. Anaerobic growth was observed in both cases after 6 to 8 days.

Sequencing of plasmid DNA revealed that a single different variant had been selected for 2-NBA (EntNFSB-s1=LS169_1) (SEQ ID No: 38), and a different variant was identified for cells grown with 4-nitrobenzyl alcohol (EntNFSB-s3=LS169_3) (SEQ ID No: 40).

NMR spectra revealed that 2-NBA or 4-nitrobenzyl alcohol had been consumed in the fermentation broth of cultures transformed with the selected variants (Table 5). In both cases, unidentified products were generated. In the case of cells grown in the presence of 2-nitrobenzoic acid, cultures acquired an intense yellow colour.

EXAMPLE 7—SELECTION OF ENTIRE MULTI-ENZYMATIC METABOLIC PATHWAYS

To prove the suitability of the methods of the invention to select functional variants of more complex systems, the inventors generated a library of pathways for isopropanol production based on the combination of genes previously designed by Hanai et al (*Escherichia coli* acetyl-CoA acetyltransferase (atoB) and, acetoacetyl-CoA transferase (atoAD), *Clostridium acetobutylicum* acetoacetate decarboxylase (adc) and CBADH) (FIG. 5*a*). The variants of the library differed in the promoter and RBS of each of the genes of the pathway, yielding a library size of over 6 million variants.

AL cells were transformed with the library and cultured anaerobically in plates of agar M9 with gluconate as the carbon source. After 36 hours, individual colonies were visible. 10 colonies were picked and inoculated in anaerobic liquid M9 with gluconate. After 8 days, growth was observed in 2 of the cultures. Plasmidic DNA was isolated of both cultures and sequenced, resulting in variants MP-S9 and MP-Sio. They were found to have the same sequence. NMR spectra of the fermentation broth revealed isopropanol was being produced. Surprisingly, the inventors also found propionate was being produced, which is a metabolite not natively produced by *E. coli* as a fermentation product. Finally, isopropanol production under aerobic conditions was compared for randomly selected variants, variants selected in plates and variants selected in plates that grew in anaerobic liquid cultures. FIG. 5*b* summarizes the isopropanol production for 10 random variants and 8 selected variants, in addition to variants MP-S9 and MP-Sio. Isopropanol production was significantly higher on average for the selected variants when compared to the random variants.

Additionally, all random and selected variants were sequenced, revealing the selective pressure had acted at two levels. There was a clear trend in selected variants, where a strong preference for a reduced number of combinations of RBS and promoters was observed. On the contrary, no clear trend was observed for random variants. This indicates that specific combinations leading to levels of expression for each enzyme that maximize the production of isopropanol had been selected.

All of the selected variants had a functional copy of all of the genes involved in the pathway. However, some of the random variants had one or more absent or inactive genes. This indicates the selection pressure eliminated defective variants without a completely functional pathway.

EXAMPLE 8—SELECTION WITH MUTANT
*GEOBACILLUS THERMOGLUCOSIDASIUS*

The inventors looked to demonstrate the portability of the selection methods and systems of the invention to other microorganisms. To this end, the inventors extended it to a thermophilic organism, as culturing it anaerobically at high temperatures would enable it to select thermostable variant polypeptides and enzymes. The inventors used a TM0236 strain, which contains two gene deletions: formate lyase (pfl) and lactate dehydrogenase (ldhA). The mutant cells are unable to grow anaerobically, whereas the wild-type cells can grow anaerobically (in both cases at 55° C., which is not a permissive temperature for *E. coli* (FIG. 18). Thus, proving that it is possible to obtain a mutant of this organism such that it becomes unable to grow under anaerobic fermentation conditions because of its inability to regenerate oxidized NAD+, which behaves in a similar way to the mutant strains of *E. coli* the inventors developed for selection.

Discussion

The inventors have developed a novel variant polypeptide or enzyme selection method based on a double mutant *Escherichia coli* strain unable to grow under oxygen-limited or substantially oxygen-free conditions, i.e. anaerobic fermentation conditions. Only upon transformation with an active NAD(H)-dependent oxidoreductase able to reduce a specific substrate present in the culture medium cells are able to regenerate oxidized NAD⁺, and can thus grow under such conditions.

The most immediate application for such a selection system is to use it to select specific variants of NAD(P)(H)-dependent oxidoreductases by transforming cells with a library of variants of the oxidoreductase, and culturing them under anaerobic fermentation conditions in the presence of the oxidized substrate of the enzyme. The inventors have demonstrated the huge potential of the system by using it to select a variant of CBADH which uses NAD(H) as the preferred cofactor instead of NADP(H), being, to their knowledge, the first enzyme with substantial NADH-dependent acetone reductase activity. Surprisingly, neither the predictions presented in previous studies where the structure of the native enzyme was solved, nor those provided by recently developed software aimed at predicting key residues for cofactor specificity in NAD(P)(H)-dependent oxidoreductases, were totally in accordance with the mutations found in the NAD(H)-dependent variant described herein. Even though there have been several attempts in the past to find sequence patterns that determine the cofactor specificity of NAD(P)(H)-dependent oxidoreductases, the findings described herein highlight the lack of general rules that can be widely applicable to invert cofactor preference.

A number of other properties can be selected for in the final variant with the selection system without much variation in the general set-up. For example, one possibility is the selection of variants with novel substrate specificity, which would require a change in the substrate supplemented to the culture medium. Such an approach could be employed, for example, to obtain enzymes with new regiospecificity or stereospecificity. These are of particular interest for the synthesis of compounds useful for their biological activity such as pharmaceuticals or agricultural chemicals, or precursors of these, where often only one specific isomer is useful for the next synthesis step, or only one specific isomer is active and all the other isomers are inactive, or can even cause undesired effects. Alternatively, a similar methodology could be used to obtain variants with enhanced activity or binding towards a substrate metabolized with low efficiency by the native enzyme.

Furthermore, the selection system is amenable to implementation in other organisms, provided that they are dependent upon, or can be modified to be dependent upon, fermentative pathways to grow under anaerobic conditions. This widens even further the enhanced properties that can be selected. For example, by using a thermophilic facultative anaerobe microorganism, such as *Geobacillus thermoglucosidasius* (which, similarly to *Escherichia coli*, also performs mixed-acid fermentation in anaerobic fermentation conditions), enzyme variants with increased thermal stability could be selected by culturing cells at higher temperatures. This approach could yield thermostable counterparts of enzymes of mesophilic organisms.

More sophisticated variations of the basic selection system can be used to enlarge further the application scope of the method by transforming LS1 strain cells with different combinations of a gene encoding an exogenous NAD(H)-dependent oxidoreductase and another genetically encoded function, typically a gene encoding another type of protein. For example, if a substrate which could be readily reduced by the oxidoreductase but was unable to permeate the cell membrane under normal conditions was supplied, a membrane transporter (comprising one or more proteins) could be coupled to the activity of the oxidoreductase. Only with a transporter able to introduce the substrate within the cell, NAD⁺ regeneration could be achieved, thus allowing the selection of transporters able to act on certain substrates. Alternatively, a two-enzyme system can be devised, where the medium would not be supplemented with the direct substrate of the NAD(H)-dependent oxidoreductase, but instead with a precursor needing a one-step transformation in order to become a substrate for the NAD(H)-dependent oxidoreductase. In such a system, cells would be transformed with the NAD(H)-dependent oxidoreductase and variants of the enzyme which could potentially catalyze the conversion of the precursor into the substrate. Furthermore, these additional genetically-encoding functions could potentially be combined.

While already applicable to a class of enzymes as wide as NAD(H)-dependent oxidoreductases, the flexibility and portability of the selection system based on metabolic complementation further increase its scope. Furthermore, with only slight modifications to the global scheme, it can be tweaked to select for enhancement in different properties of the gene of interest. The inventors expect it to become a valuable tool which will help identify enzymes with novel properties which can be used to develop new synthetic pathways or be integrated into already existing ones to optimize them. The inventors have applied it to a variety of oxidoreductases, including alcohol dehydrogenases, imine reductases and nitroreductases. Furthermore, the inventors have used it to select for different properties, including cofactor specificity/preference, improvement of kinetic parameters and substrate specificity/preference.

The inventors applied the selection method to select for a different type of biomolecules other than NAD(H)-dependent oxidoreductases, namely promoter and ribosome binding site (RBS) sequences. They have demonstrated that the selection method is suitable to select an optimal combination of several of these regulatory elements leading to maximized production of a given product thanks to the combined action of a set of several enzymes, including enzymes that are not NAD(H)-dependent oxidoreductases, and not even oxidoreductases.

REFERENCES

Baba, T., Ara, T., Hasegawa, M., Takai, Y., Okumura, Y., Baba, M., Datsenko, K. A., Tomita, M., Wanner, B. L. & Mori, H. (2006) Construction of *Escherichia coli* K-12 in-frame, single-gene knockout mutants: the Keio collection. Molecular Systems Biology. 2 2006.0008.

Berrios-Rivera, S. J., Bennett, G. N. & San, K. Y. (2002) The effect of increasing NADH availability on the redistribution of metabolic fluxes in *Escherichia coli* chemostat cultures. Metabolic Engineering. 4 (3), 230-237.

Cahn, J. K., Werlang, C. A., Baumschlager, A., Brinkmann-Chen, S., Mayo, S. L. & Arnold, F. H. (2017) A General Tool for Engineering the NAD/NADP Cofactor Preference of Oxidoreductases. ACS Synthetic Biology. 6 (2), 326-333.

Cherepanov, P. P. & Wackernagel, W. (1995) Gene disruption in *Escherichia coli*: TcR and KmR cassettes with the option of Flp-catalyzed excision of the antibiotic-resistance determinant. Gene. 158 (1), 9-14.

Geertz-Hansen, H. M., Blom, N., Feist, A. M., Brunak, S. & Petersen, T. N. (2014) Cofactory: sequence-based prediction of cofactor specificity of Rossmann folds. Proteins. 82 (9), 1819-1828.

Hamilton, C. M., Aldea, M., Washburn, B. K., Babitzke, P. & Kushner, S. R. (1989) New method for generating deletions and gene replacements in *Escherichia coli*. Journal of Bacteriology. 171 (9), 4617-4622.

Hanai, T., Atsumi, S. & Liao, J. C. (2007) Engineered synthetic pathway for isopropanol production in *Escherichia coli*. Applied and Environmental Microbiology. 73 (24), 7814-7818.

Hollrigl, V., Hollmann, F., Kleeb, A. C., Buehler, K. & Schmid, A. (2008) TADH, the thermostable alcohol dehydrogenase from *Thermus* sp. ATN1: a versatile new biocatalyst for organic synthesis. Applied Microbiology and Biotechnology. 81 (2), 263-273.

Korkhin, Y., Kalb(Gilboa), A. J., Peretz, M., Bogin, O., Burstein, Y. & Frolow, F. (1998) NADP-dependent bacterial alcohol dehydrogenases: crystal structure, cofactor-binding and cofactor specificity of the ADHs of *Clostridium beijerinckii* and *Thermoanaerobacter brockii*. Journal of Molecular Biology. 278 (5), 967-981.

Maddock, D. J., Patrick, W. M. & Gerth, M. L. (2015) Substitutions at the cofactor phosphate-binding site of a clostridial alcohol dehydrogenase lead to unexpected changes in substrate specificity. Protein Engineering, Design & Selection: PEDS. 28 (8), 251-258.

Reed, J. L., Vo, T. D., Schilling, C. H. & Palsson, B. O. (2003) An expanded genome-scale model of *Escherichia coli* K-12 (iJR904 GSM/GPR). Genome Biology. 4 (9), R54-2003-4-9-r54. Epub 2003 Aug. 28.

The invention claimed is:

1. A method of identifying a variant polypeptide of interest, or its encoding polynucleotide, the method comprising:

(i) generating a plurality of polynucleotides encoding a plurality of variant polypeptides comprising the variant polypeptide of interest;

(ii) expressing the plurality of variant polypeptides in an obligate or facultative anaerobe that is incapable of, or displays a reduction in, the oxidation of NADH and/or NADPH under anaerobic fermentation conditions;

(iii) culturing, in growth media, the obligate or facultative anaerobe under anaerobic fermentation conditions, wherein the anaerobic fermentation conditions comprise the absence of an external electron acceptor, in the presence of a substrate, wherein the polypeptide of interest enables the obligate or facultative anaerobe to oxidise, or to increase oxidation of, NADH and/or NADPH in the presence of the substrate;

(iv) selecting an obligate or facultative anaerobe that grows or displays a growth advantage in the growth media; and (v) identifying the variant polypeptide of interest expressed, or its encoding polynucleotide, in the obligate or facultative anaerobe of step (iv);

wherein the substrate is exogenously added to the growth media.

2. The method according to claim 1, wherein the variant polypeptide comprises at least one amino acid substitution, deletion or insertion compared to its wild-type counterpart, or comprises a synthetically designed polypeptide.

3. The method according to claim 1, wherein the variant polypeptide is expressed in step (ii) by the introduction of a vector comprising a polynucleotide encoding the variant polypeptide into the anaerobe.

4. The method according to claim 1, wherein the obligate or facultative anaerobe is a bacterium, yeast or fungus, optionally wherein the obligate or facultative anaerobe is *Escherichia coli*.

5. The method according to claim 1, wherein the obligate or facultative anaerobe is rendered incapable of, or displays a reduction in, the oxidation of NADH and/or NADPH by having at least one gene, or product thereof, associated with an $NAD^+$ and/or $NADP^+$ regeneration metabolic pathway, which is non-functional and/or inhibited, optionally wherein the at least one gene has been deleted, disrupted or mutated, optionally wherein the at least one gene encodes lactate dehydrogenase, alcohol dehydrogenase, soluble transhydrogenase and/or transmembrane transhydrogenase, optionally wherein the facultative anaerobe is *Escherichia coli* and the at least one gene encodes lactate dehydrogenase (ldhA), alcohol dehydrogenase (adhE), soluble transhydrogenase (sthA) and/or transmembrane transhydrogenase (pntA and/or pntB).

6. The method according to claim 1, wherein the obligate or facultative anaerobe is a thermophilic organism, and the obligate or facultative anaerobe is cultured in step (iii) at a temperature greater than 37° C., 40° C., 50° C., 60° C. or at least 70° C. and the variant polypeptide of interest is one which is able to provide for oxidation, or an increase in oxidation, of NADH and/or NADPH at such temperatures.

7. The method according to claim 1, wherein an obligate or facultative anaerobe that is not expressing the variant polypeptide of interest will not grow, or grow at a reduced rate, when compared to an obligate or facultative anaerobe expressing the variant polypeptide of interest, when culturing under the conditions of step (iii), enabling the selection of the obligate or facultative anaerobe expressing the variant polypeptide of interest in step (iv).

8. The method according to claim 1, wherein the identification of the variant polypeptide of interest, or it encoding polynucleotide, in step (v) comprises:

i. extracting the protein and/or DNA from the obligate or facultative anaerobe; and ii. determining the variant polypeptide sequence, or the polynucleotide sequence encoding the variant polypeptide sequence.

9. The method according to claim 1, wherein the variant polypeptide is selected from the group consisting of: an enzyme, a membrane transporter, a transcription factor and a chaperone.

10. The method according to claim 1, wherein the variant polypeptide is an enzyme, optionally wherein the enzyme displays an altered specificity selected from a group consisting of: stereospecificity, thermostability, chemostability, pressure stability, substrate specificity, catalytic efficiency, oxidative stability regiospecificity, cofactor preference and/or specificity, and binding affinity for substrate and/or cofactor, optionally wherein the enzyme is an NAD(P)H-dependent oxidoreductase.

11. The method according to claim 1, wherein the variant polypeptide is a membrane transporter, optionally wherein the membrane transporter is an active transporter, a passive transporter, or a membrane channel.

\* \* \* \* \*